(12) United States Patent
Skeeles et al.

(10) Patent No.: US 6,406,843 B1
(45) Date of Patent: Jun. 18, 2002

(54) POULTRY VIRUS ISOLATES AND METHOD

(75) Inventors: John K. Skeeles, Fayetteville; Lisa A. Newberry, Lowell, both of AR (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/876,849

(22) Filed: Jun. 5, 2001

Related U.S. Application Data

(60) Provisional application No. 60/076,136, filed on Feb. 27, 1998.

(51) Int. Cl.$^7$ .................. A61K 39/00; A61K 39/12; C12Q 1/70; C12N 7/00
(52) U.S. Cl. ............... 435/5; 424/184.1; 424/204.1; 435/235.1

(58) Field of Search ............... 435/5, 235.1; 424/184.1, 424/204.1

*Primary Examiner*—Hankyel T. Park
(74) *Attorney, Agent, or Firm*—Head, Johnson & Kachigian

(57) ABSTRACT

Infectious bursal disease viruses were isolated from broiler chickens experiencing proventriculitis in, for example, Oklahoma, Texas, West Virginia, and California. Chicken virus isolates Texas RB 3, Texas RB 4, HBS, F57-7, W/L 39, GAR 1, and the like have been isolated. These viruses are some of the major causes of this condition and can be utilized as or in a vaccine to prevent the disease condition. The viruses are a significant finding in the search for a causative agent for proventriculitis in broiler chickens and as such may be utilized in the development of a vaccine or vaccines. The viruses can be attenuated to be used as a modified live vaccine or utilized in an inactivated form in a killed vaccine.

5 Claims, 26 Drawing Sheets

FIG. 23

SERUM ANTIBODY

[Bar chart showing Antibody G.M.T. (0–4000) vs Days Post-Infection (4, 6, 8, 11) with three groups: Var E/DEL, Var E/1084, USDA/STC]

Legend: Var E/DEL | Var E/1084 | USDA/STC

POULTRY VIRUS ISOLATES AND METHOD

CROSS REFERENCE TO RELATED APPLICATION

This application is a continuation-in-part of U.S. provisional application Serial No. 60/076,136, filed Feb. 27, 1998.

The present invention is directed to chicken virus isolates or strains (Texas RB 3, Texas RB 4, HBS, F57-7, W/L 39, GAR 1) believed to be a new strain or strains of infectious bursal disease virus (IBDV) which infects the proventriculus, a vaccine made from these isolates, a method of treatment, vaccination scheme, and the like.

In accordance with the present invention, numerous experiments were conducted to determine the role of infectious bursal disease (IBD) virus in the induction of lesions associated with proventriculitis syndrome in chickens. Parameters examined included age of the chicken at IBD virus exposure, concentration of IBD virus at exposure the strain of IBD virus, dietary influence in the presence of IBD virus, mixed IBD virus infection, autoimmune mediated IBD reactions associated with lesion production, viral induced apoptotic tissue injury and isolation and characterization of the causative agent.

The experiments were carried out in SPF white leghorns, with the experimental birds being examined for the presence of gross and microscopic lesion at 4 and 11 days post challenge. Tissue homogenates were analyzed for the presence of IBDV at 4 and 11 days post challenge with Antigen Capture ELISA (AC-ELISA). Determinations of neutralizing antibody levels and IgG antibody responses were monitored as well as depletion of serum complement following IBDV infection. Physical parameters were also considered utilizing body weights and organ to body weight ratios to determine IBDV effects following experimental challenge.

Physical parameters indicated that the primary viral response is predominantly in the bursa of Fabricius, but changes were also noted in the proventriculus. Physical changes in the proventriculus occurred primarily during the acute stage of the IBD virus infection.

Gross and microscopic lesions in the proventriculus were exacerbated by the presence of copper sulfate supplementation in the feed. There were also very evident negative effects on the weight gain of SPF white leghorn chickens given copper sulfate feed supplementation.

Infectious bursal disease virus strains show different affinities for producing lesions in the proventriculus following challenge. Standard challenge IBD virus USDA/STC stain produced the most consistent lesions in the proventriculus often accompanied by hemorrhage. This correlates well with antibody enhanced pathology as observed with antigen-antibody complex activation of serum complement. Evidence of yet another mechanism of IBDV induced pathology, was demonstrated through the use of TUNEL apoptosis staining of infected tissues. The degree of apoptotic involvement was also reflected in the pathogenicity of the IBD virus strain used for challenge.

Infectious bursal disease viral inclusions were demonstrated by thin section electron microscopy in the proventriculus at 4 days post challenge. Viral inclusions resemble previously documented inclusions produced in the bursa following IBD infection.

In accordance with the present invention, infectious bursal disease viruses were isolated from broiler chickens experiencing proventriculitis in, for example, Oklahoma, Texas, West Virginia, and California.

IBDV Antigen Capture (AC) Elisa tested positive for Texas RB 3, Texas RB 4, HBS, F57-7, W/L 39, and GAR 1. Virus isolation in SPF embryonated eggs was completed and 3rd and final passage for the isolates. SPF chickens were inoculated with egg harvest for the isolates. Tissues from inoculated birds and histopathology confirmed lesions. AC-ELISA of tissue and serological confirmation of the isolates was performed.

Proventriculitis is a major problem to the broiler industry. These viruses may be one of the major causes of this condition and if this proves to be true, could be utilized as or in a vaccine to prevent the disease condition. The viruses are believed to be a significant finding in the search for a causative agent for proventriculitis in broiler chickens and as such may be utilized in the development of a vaccine or vaccines. The viruses can be attenuated to be used as a modified live vaccine or utilized in an inactivated form in a killed vaccine.

TABLE OF CONTENTS

INTRODUCTION
BRIEF DESCRIPTION OF THE DRAWINGS
I. SECTION 1
  DETERMINATION OF THE ROLE OF INFECTIOUS BURSAL DISEASE VIRUS STRAIN VARIANT 1084-E IN THE INDUCTION OF PROVENTRICULITIS IN SPF CHICKENS: AGE RELATED EFFECTS
II. SECTION 2
  DETERMINATION OF THE ROLE OF INFECTIOUS BURSAL DISEASE VIRUS STRAINS USDA/STC AND VARIANT 1084-E ON THE INDUCTION OF LESIONS ASSOCIATED WITH PROVENTRICULITIS: INFLUENCE OF VIRUS CONCENTRATION AND TIME
III. SECTION 3
  THE INTERACTION OF INFECTIOUS BURSAL DISEASE VIRUS, REO VIRUS, AND COPPER SULFATE IN THE PRODUCTION OF LESIONS ASSOCIATED WITH PROVENTRICULITIS IN SPF WHITE LEGHORN CHICKENS
IV. SECTION 4
  INFECTIOUS BURSAL DISEASE VIRUS INDUCED APOPTOSIS ASSOCIATED WITH PRODUCTION OF LESIONS IN THE PROVENTRICULUS AND BURSA
V. SECTION 5
  MEASUREMENT OF HEMOLYTIC COMPLEMENT LEVELS AND VIRUS NEUTRALIZING ANTIBODY TITERS 4, 6, 8 AND 11 DAYS POST CHALLENGE WITH INFECTIOUS BURSAL DISEASE VIRUS STRAINS USDA/STC, VARIANT E/DEL, AND VARIANT E/1084
VI. SECTION 6
  THE INTERACTION OF INFECTIOUS BURSAL DISEASE VIRUS (USDA/STC) AND COPPER SULFATE IN THE PRODUCTION OF LESIONS ASSOCIATED WITH PROVENTRICULITIS IN BROILER CHICKENS
VII. SECTION 7
  ISOLATION AND CHARACTERIZATION OF INFECTIOUS BURSAL DISEASE VIRUS FROM BROILER CHICKENS EXHIBITING SYMPTOMS OF PROVENTRICULITIS
VIII. FURTHER DISCUSSION
IX. APPENDIX CLAIMS ABSTRACT OF THE DISCLOSURE

INTRODUCTION

The primary impetus for this invention came as a result of a request for help from a number of commercial poultry processors. Proventriculitis has been described in broiler chickens from a number of geographical locations. This syndrome is characterized by the enlargement of the proventriculus, with feed impaction, and structural weakness. Affected birds can be either normal or underweight at processing, with either a high or normal feed conversion efficiency. Problems generally manifest at the processing plant with breakage of the proventriculus during mechanical evisceration, resulting in an increased number of washouts, slowed or stopped processing lines, excessive trims, and higher than normal levels of condemnation. This proventriculitis syndrome has been linked to a number of environmental, nutritional, genetic, and infectious causes.

Preliminary studies indicate that infectious bursal disease virus is capable of producing lesions in the proventricular mucosa. While proventriculitis induced by IBDV alone does not exactly mimic what is observed in field situations, it is contented that IBDV plays the role of a facilitator, and thus presents an opportunity for other viral, bacterial, fungal or chemical pathogens to exert an effect.

Some objects of this invention are to: (1) attempt to establish infectious bursal disease virus as a causative agent in the induction of lesions associated with proventriculitis, (2) determine the pathogenic mechanism by which IBDV exerts an effect on the proventriculus, and (3) to isolate and characterize IBDV virus from field cases of proventriculitis.

Infectious Bursal Disease Virus

Infectious bursal disease (IBD) is an acute viral infection which predominantly affects domestic chickens. This viral disease has also been described in commercial turkeys (22, 60, 81, 82, 119), and represents an occasional problem in ducks (81). Infectious bursal disease virus infection and replication occurs primarily in lymphoid tissues throughout the body. This results in induction of significant pathological lesions within the follicles of the bursa of Fabricius, which contains the highest concentration of lymphoid cells. When infection occurs at an early age (<3 weeks), the disease syndrome may be further complicated by an accompanying immunosuppression (33, 76, 95).

In 1962, Cosgrove (20) first described this disease syndrome and an associated nephritis in a chicken flock in Gumboro, Delaware. Early studies gave conflicting information concerning this disease. It was later determined that the nephritis syndrome described was actually a variant strain of infectious bronchitis virus and another, as yet, unknown infectious agent (12). Studies of tissues harvested from infected birds revealed the presence of virus particles that were structurally different from infectious bronchitis virus. The name Gumboro disease was adopted to describe this new infectious disease syndrome (10,95).

Hitchner (50) proposed the final name of infectious bursal disease virus to identify the etiological agent responsible for inducing pathognomonic lesions of the cloacal bursa. It was finally characterized as a member of the Birnaviridae family, which reflects that it has a genome that consists of two segments of dsRNA (10,26,76).

Infectious bursal disease virus (IBDV) infection represents a disease of significant economic importance within the poultry industry. Economic impact of IBDV infection is manifested by the mortality it induces during the initial acute infection, and secondly from the induction of an immunosuppressive syndrome in chicks infected immediately after hatching. The virus is considered ubiquitous in nature, with a worldwide distribution in all major poultry producing areas with the exception of a few isolated islands in the south Pacific (76,95,119).

Vaccination procedures for this virus are practiced extensively by commercial producers and are such that all chickens become seropositive to IBDV during their growout (35). Successful vaccination programs are evident in that clinical cases of IBDV are extremely rare. However, IBDV infections do still occur, and usually become apparent only after the introduction of a secondary pathogen. Modifications of the IBDV infection can occur in the presence of maternal antibodies (135) or as a result of variant IBDV strains that induce immunosuppression with no obvious clinical disease (95,119).

Two serotypes of IBDV are currently recognized, they are designated as serotype 1 and serotype 2 (81). The serotype 1 IBDV group can be further divided into two subtypes, the so called "Classic" and "Variant" (76) . There is additional evidence of IBDV isolates that represent a viral group that is transitional between classic and variant (6,7,128). Serotype 1 IBDV classic viruses were the first to be described in chickens, and as such, there is a great deal of information available concerning their characteristics. Variant IBDV strains of serotype 1 represent a new faction of this viral disease syndrome. While variant strains of serotype 1 IBDV maintain structural similarities and replication strategies, they are capable of breaking through maternal antibody generated against classical subtypes (110, 112). The appearance of variants within the viral population appears to be a reflection of the intensity of the vaccination program, with most variants representing a viral subpopulation selected by the use of live IBDV vaccines. Documented variant strains found within serotype 1 IBDV show distinct sequence differences in the VP2 gene from the classic viruses, indicating that mutations of the viral genome also influence the emergence of variant IBDV strains (128).

Serotype 2 IBDV antibodies are found in both chickens and turkeys, suggesting that this IBDV serotype also has a widespread geographical distribution. This particular subtype is noted in particular for their inability to induce detectable clinical symptoms. The so-called apathogenesis of IBDV serotype 2 has been attributed to the virus lacking a selective tropism for the bursa of Fabricius (22,99). Recent studies have also linked this apathogenesis to the inability of serotype 2 IBDV to utilize macrophages for distribution of virus particles throughout the host. This observation was made utilizing in-vitro cell culture in which serotype 2 virus infected cells underwent a rapid lytic cycle (138). Presence of antibodies to serotype 2 IBDV does not confer protection against serotype 1 IBDV, although it has been determined that both serotypes share a high degree of genetic homology (43,59,60).

Etiology

IBDV is a classified as a member of the Birnaviridae family, which has only one genus Birnavirus. The recognized prototype virus in this classification is infectious pancreatic necrosis virus (IPNV) of fish (trout). This virus family also includes Tellina virus (bivalve mollusks, oysters) (26), Drosophila X (fruit fly) (13), and Eel virus (fresh/saltwater eels). Cross virus neutralization tests indicate that all the aquatic viruses within this family are related to each other, but are different from the avian and insect isolates (26).

Infectious bursal disease virus particles range in size from 55–60 nm, possess an external single shell, are non enveloped, and exhibit icosahedral symmetry (26,39,48,68, 101,104,119). The capsid consists of 32 capsomeres arranged in a skewed (dextro) 5:3:2 symmetry (47,101). The G+C content is 55.3%, with a purine to pyrimidine ratio of approximately 1. IBDV is resistant to inactivation by ether, chloroform, pH levels between 2.0 and 12.0, and has a $T_m$ of 95.5° C., (12).

The buoyant density of complete particles was determined by the use of cesium chloride gradients and ranges from 1.31 to 1.34 g/ml (47). Viral particles on the lower density range contain significantly lower levels of dsRNA or are completely empty (85). Lower density particles exhibit identical morphology but lack the proteins of the proper size and concentration to initiate an effective infection. Incomplete particles, are unable to initiate infection, and constitute approximately 10% of any given Birnavirus preparation (7,47,85,89).

Physiochemical Composition

The IBDV genome of serotype 1 consists of two segments of dsRNA (12, 88) of approximately equal size, segment A has a molecular weight of $3.4 \times 10^6$ and segment B has a molecular weight of $2.8 \times 10^6$ (10, 12, 26, 47, 86, 95, 104, 119). Serotype 2 IBDV exhibit a difference in the size of both segment A and B which are smaller by approximately 70 bp and 20 bp respectively (10, 60), although there appears to be no difference in function (11, 98). Five viral proteins have been identified for IBDV; they are as follows with their approximate molecularweights: VP1(90,000), VP2 (44,000), VP3 (35,000), VP4 (28,000), and VP5 (17,000) (25, 119). Segment A codes for a polyprotein within a single open reading frame (ORF) in the following order N-VP2-VP5-VP4-VP3-C (4, 63, 83, 117). Segment B codes for a single protein VP1 (83, 87, 103).

VP2 and VP3 are the major structural proteins (99, 130) and collectively constitute 91% of the total viral protein. VP1 and VP4 are considered minor proteins (enzymes) and VP5 of unknown function collectively represent the remaining 9% of viral protein. Viral protein one (VP1) codes for a viral RNA polymerase, which is a required element for replication of dsRNA. Since all IBDV's encode their own viral polymerase, transcription and replication are initiated immediately after the virus penetrates the host cell without need for uncoating or any type of degradation of the nucleocapsid (131). Infectious bursal disease virus utilizes the strand displacement model of replication, with VP1 also functioning as a viral replicase (130). Viral protein four (VP4) codes for a viral protease which processes the large segment A polyprotein precursor into mature viral proteins (62,63,83,98). VP5 has no known function at this time (119).

Viral protein two (VP2) represents the major host protective immunogen (61) and functions in virus adsorption to the host cell (68). Variability in the VP2 amino acid sequence is found predominantly within the antigenic binding epitope. Significant changes in this genomic region are often associated with emergence of variant IBDV strains (3, 4, 11, 14, 31, 69, 98).

Neutralizing antibody from the host animal is generated against the antigenic structure within the VP2 protein (30). Development of neutralizing antibodies in the host animal against viral VP2 is highly conformational dependent (11). Experimental studies utilizing renatured VP2 protein demonstrated the crucial importance of maintaining the native state of the VP2 antigen binding epitope. The renatured VP2 was capable of binding neutralizing antibodies, however, antibodies generated against this protein were not neutralizing (98).

Viral protein three (VP3) contains two conformational independent non-overlapping binding epitopes (61, 127); one of these epitopes is conserved across serotypes and one is distinct for each serotype (87, 99). Antibodies specific to VP3 are the first to appear in detectable levels in chickens following infection (61).

Viral protein one (VP1) forms a dsRNA protein complex, by covalently binding knoblike proteinaceous structures to the ends of the two genomic segments, forming a circularized ring structure. Viral protein one (VP1) exhibits the characteristics of an RNA dependent RNA polymerase and functions also as an assembly protein. Genome linked proteins are common in Birnaviruses (87, 103, 131), and their presence Indicates that replication of nucleic acid is by strand displacement (semi-conservative) mechanism (13, 131) The physiological function of VP1 protein is still unknown, although it has indications of involvement in RNA replication as well as in virus assembly (83, 87).

Clinical Disease

Chickens infected with IBDV exhibit trembling and ruffled feathers with additional signs of depression and anorexia. These symptoms are accompanied by a profuse uratecontaining diarrhea with some indication of bile stasis. The diarrhea syndrome is further complicated by the birds refusal to eat or drink, with most infected birds exhibiting evidence of dehydration. During acute IBDV infection there is an initial elevation of body temperature, which falls below normal shortly before death. Blood calcium levels are lowered (20) and there is evidence of the presence of additional blood clotting deficiencies (122,124).

Clinical IBDV is most commonly recognized in susceptible 3 to 6 week-old chickens. Although an early age resistance to infection, regardless of maternal antibody has been proposed (29, 50, 100, 141). Infectious bursal disease virus infection, within the first week of hatch leads to severe defects of humoral immune response (49). Mortality from IBDV infection was shown to be associated with a severe depletion of complement (123, 124), and clotting abnormalities without changes in complement (124).

Virus persistence was measured in a number of studies which considered the amount, and the route of virus inoculation, as well as the age of the bird when the virus challenge was given. Virus could be visualized, using the electron microscope, within fours hours PI in the cecum, and within 5 hours in the duodenum and jejunum. It was determined that IBDV could be reisolated from infected organs within 24 hours post infection (PI), regardless of the age of the bird, the dose given, or the route in which it was administered. Virus could not be recovered beyond day 11, with birds challenged at 1, 7, and 14 days of age. Birds challenged with IBDV at 21 days of age tested positive for only 8 days (79). In general, older birds at challenge experience shorter periods of viremia, but have a more rapid and higher intensity immune response (141). Bayyari et al. described extended periods of viremia associated with increased levels of defective IBDV viral particles following attenuation of IBDV in cell culture (7).

Laboratory Host Systems

Infectious bursal disease virus can be propagated in specific pathogen free (SPF) embryonated eggs on the chorioallantoic membrane (CAM) or by the yolk sac (YS) route at day 9 of embryonation. Chorioallantoic membrane inoculation is considered to be the most sensitive method of virus isolation and propagation. Embryos that become infected with IBDV show petechial hemorrhages on the head, trunk, and feet, as well as edema within the abdominal cavity. Internally, the livers of affected embryos may demonstrate necrosis, but more commonly are pale and take on a parboiled or cooked texture. The spleen is usually normal in size with the exception of variant IBDV where there is significant enlargement of the spleen, in both cases the spleen is generally pale and may occasionally demonstrate necrosis. Embryonic bursae are extremely small with occasional hemorrhage. Mortality, if it occurs, is usually between 3 to 5 days PI, and, as a general rule, is absent in the presence of variant IBDV strains. The highest concentrations of the IBDV virus are found in the CAM, body and viscera of the infected embryo (109).

Cell culture has become an increasingly economical and efficient tool for measuring virus effects outside (in-vitro) the host animal. A number of years ago it was determined that IBDV could be adapted to grow in cell culture. Infectious bursal disease virus propagation in primary cells derived from SPF chickens and/or embryos results in the highest yield of virus particles (70). Growth of IBDV, both classic and variant strains, has been accomplished in the following primary cells: chicken bursal lymphoid (CBL), chicken embryo kidney(CEK) and chicken embryo fibroblast (CEF)(18, 46, 75, 82, 96, 126). Viral proteins of most IBDV are present at detectable levels by 90 minutes post inoculation (PI) in CEF cells. Virus replication then enters a latent stage at approximately 4 hours (56), with mature virus particles evident as early as 6 hours PI (85), and mature virus particle release between 10–16 hours PI (59, 75, 77, 90, 94). Virus replication in CBL cells closely parallels that of CEF cells, however, IBDV infection of CEK cells is of extended duration (59). Cytopathic effects induced by IBDV infection are visible by 16 hours PI (75, 94) and virus titers generally peak at 48 hours PI (18). In addition, it has been determined that IBDV infection activates complement in cultured lymphoid cells (71), and that IBDV progeny virus release is followed within 2–8 hours by an increase in the synthesis of interferon (34).

Several mammalian cell lines RK-13, VERO, BGM-70, and MA-104 will also support IBDV growth (34,42,56,75, 104). Virus particle yields are lower, and the replication cycle is prolonged when compared to IBDV propagation in chick primary cells (56,75). Repeated passage in these cell lines leads to loss of pathogenicity and represent a means by which highly pathogenic IBDV can be attenuated for utilization as vaccines (6,40,42,143).

Cell culture propagation of IBDV under conditions where there is a high concentration of virus particles (MOI) and limited cellular substrate will result in the production of incomplete virus particles. Upon further passage in cell culture virus stocks containing these defective interfering (DI) particles show reduced virus yields and reduced pathogenicity (6,7,84). The mechanism that triggers some IBDV viruses to produce DI particles and other IBDV not to, is not clear at this point in time (6,89).

Cytopathic effects (CPE) of IBDV infection in cell culture are described as plaque formation. Extensive passage in cell culture can induce IBDV to form plaques of various sizes. It has been determined that IBDV virus stocks which produce large plaque CPE are more virulent than those that produce small plaque CPE (23,73,113).

Cell culture propagation of IBDV is not without controversy. A number of researchers have reported conflicting results from cell culture derived IBDV stocks, especially when they are introduced back into the chicken. These differences have raised some concern as to whether in-vitro observations of IBDV infection correspond in any way to what happens in-vivo, although the use of in-vitro methods continues to be a widely accepted method of analysis for IBDV infection (54).

Virus Detection

The presence of IBDV within infected tissues and/or the presence of antibodies following infection can be determined with a number of different laboratory tests. The agar gel precipitin test (AGPT) can be used to detect IBDV group specific antibody. The test can be both quantitative and qualitative, but is of extremely low sensitivity, and therefore misses detection of low virus concentrations and is only useful during the first few days of IBDV infection (58,109).

Virus neutralization assays are highly specific for the identification and characterization of IBDV isolates. The test is performed utilizing primary CEF cell monolayers. Infectious bursal disease virus of a known serotype is reacted at a constant concentration with varying amounts of immune serum. The antigen-antibody mixture is then inoculated onto cell monolayers and incubated. Following incubation the cells are fixed and stained. Endpoints are determined visually and neutralization index titers are expressed as the reciprocal of the highest dilution of antiserum that prevents IBDV from inducing cytopathic effect in cell culture monolayers. Infectious bursal disease viruses can be pathotyped using cross neutralization assays, and also quantitated (7,32, 109).

Fluorescently labeled antibodies are now readily available, and offer a unique, yet diverse diagnostic tool. Immunofluorescent staining of enzyme treated formalin fixed tissues using IBDV polyclonal antiserum was capable of detecting IBDV (58,65), and also non-specific presence of IgG complexes in the glomeruli of IBDV infected chickens (74). Utilization of two fluorogenic labels was also demonstrated as a means of quantitation of IBDV replication in cell culture, as a reflection of live/dead cell ratios (5).

The Enzyme Linked Immunosorbent Assay (ELISA) is by far the most widely used diagnostic test in the modern poultry industry, and is also capable of determining the presence of antibodies to many other pathogens. The popularity of commercial ELISA kits results from the ease of performance, accommodation of a large number of samples, high sensitivity, and economical price. Commercial ELISA kits for IBDV quantitate the presence of virus specific antibodies only (109). Variations of the standard ELISA are utilized to determine the presence of virus in IBDV infected tissues, but remain predominantly as a research tool. The Antigen Capture-ELISA developed by Snyder et al. (128) utilizes monoclonal antibodies specific to the surface markers of IBDV to capture virus from tissue homogenates. Field virus populations of IBDV were screened and determined to be relatively homogenous falling into three major antigen types. Antigenic types identified could be segregated into distinct geographical regions of the United States (128). This technology has since been modified to use polyclonal antiserum to capture virus from infected tissues. Early indications are that polyclonal serum may actually bind more virus than the monoclonal antibody, due to the presence of antibodies to multiple antigenic sites (41).

The development of a kinetic based ELISA was utilized to determine the rate of antibody decay. Results from these assays indicated that progeny from parents vaccinated 4 times or more had higher rates of antibody decay than those being vaccinated only twice (129).

Molecular biology procedures have also been refined for the diagnosis, characterization, and identification of classic and variant IBDV. Detection of IBDV in tissue was accomplished utilizing a biotin labeled cDNA derived from segment A at the VP2/VP4 junction. Infected tissues demonstrated specific staining, however, the intensity of the stain did not correlate with virus titer determined by other means (45,57). Randomly derived cDNA probes demonstrated similar results (24). Dot blot hybridization was utilized to detect IBDV in tissue with a probe derived from the cloned sequence of VP1. IBDV could be detected by this method from day 1 to day 24, with the test also demonstrating a wide specificity encompassing both serotypes (58).

The polymerase chain reaction (PCR) has been modified so that it can be utilized for the direct amplification of IBDV from infected tissues (55,142). Because infected samples must first be copied into cDNA by reverse transcriptase, and then amplified with PCR, this procedure is called RT-PCR. A secondary analysis is performed in which restriction enzymes are used to cut the amplified product resulting in the formation of a banding pattern that will identify it as to IBDV serotype classic or variant (55).

Immunity

Infectious bursal disease virus represents a true paradox, in that it replicates in immune cells and destroys them, yet is capable of stimulating an extremely high immune response (36,52). Because of this immunogenic ability, IBDV infection can be effectively controlled with use of one of any number of vaccination programs. Most IBDV vaccination programs for commercial chickens utilize a combination of a live virus vaccine and inactivated oil emulsion vaccine containing serotype 1 IBDV. Commercial vaccines are available in a number of formulations and concentrations (35,93). The vaccine type employed by the producer will reflect which IBDV is currently causing disease on their premises. Vaccination regimens also vary as to route of administration, timing of administration, number of repetitions, and dose given. Infectious bursal disease virus vaccinations are given to the breeder flock to boost maternal antibody levels that are transferred to the progeny.

Maternal antibody levels are capable of protecting the chick for the first few weeks, but are generally insufficient to protect for the entire growout (29,135). In addition, maternally derived antibody is not uniformly distributed to the progeny, so it is evident that production flocks will contain both susceptible and protected birds at any given time (135).

Earliest vaccinations for IBDV are administered in-ovo at day 18 of embryonation. Virus neutralization (VN) antibody titers in chicks that received the vaccine in-ovo resulted in a resistance to challenge from virulent IBDV up to 10 weeks of age (116). Licensed vaccines are now available for mechanical administration into the yolk sac at 18 days of embryonation (2,38). In general, hatchery vaccination is somewhat questionable because of interference from high levels of maternal antibodies (135). In the hatchery, IBDV vaccination can also be given by microaerosol spray, or subcutaneous injection. Field vaccination for IBDV is customarily delivered in the drinking water.

Infectious bursal disease virus live vaccines are usually derived from attenuated IBDV field virus strains. Attenuation is accomplished by the repeated passage of the virus through cell culture and/or embryonated eggs (126). Live vaccines also spread laterally from bird to bird and carry with them the potential to revert to virulence and, as such, pose a threat to the very birds they were designed to protect (35). There is no evidence at present to indicate that IBDV infection is spread vertically.

Infectious bursal disease virus vaccines are classified by the degree of pathology they induce in the bursa as being mild, intermediate, or invasive. Invasive vaccines induce a high degree of bursal damage which is accompanied by immunosuppression, but produce high antibody titers. Live invasive IBDV vaccines are usually administered in the presence of low levels of maternal antibodies in production birds or following priming with a killed oil emulsion vaccine in breeders (35,76).

Genetically engineered vaccines for IBDV have been described in which various pieces, mainly VP2, are expressed in a number of different vectors. Field testing indicates that most of these products stimulate antibody production, and since they contain only pieces of the IBDV genome, do not pose a threat to virulence. However, antibody produced using these constructs, at best, offer only limited protection and are not economically feasible for widespread application (62,80).

Immunosuppression

Immunosuppression represents a physiological state in which an individual exhibits temporary or permanent dysfunction of the immune response, resulting from some type of damage to the immune system. Whether temporary or permanent immunosuppression ultimately leads to an increased susceptibility to other disease pathogens. Two basic categories of immunosuppression are considered; one that is antigen specific, and the other is a generalized unresponsiveness of the immune system (119,120).

Antigen specific immunosuppression results in the loss of a specific type, or types, of cell following exposure to the pathogen and can occur directly or indirectly. Direct interference by the pathogen occurs when replication takes place in a specific immune cell or in a cell that in some way plays a role in innate immunity (49). Indirect effects occur when the pathogen interferes with the regulatory cells of the immune system. Both direct and indirect immunosuppression invoke negative consequences for the complete development of antigen specific antibodies. Generalized immunosuppression is most often associated with genetic and/or physiological deficiencies in which the immune cells are absent or the body fails to produce cells or substances necessary to sustain an immune response (49,72.120,121).

Immunosuppression following IBDV infection is characterized by a severe lymphoid cell depletion in the bursa. There is some evidence of additional cellular depletion in the thymus and hematopoietic cell loss in the bone marrow. Lesions induced by IBDV reflect that the virus prefers to replicate in IgM bearing lymphocytes, but can, and will utilize other lymphocytes as well as macrophages throughout the body. Loss of most of the functional B-cells results in the inability to produce antibodies to IBDV or, for that matter, any other pathogen that comes along afterward. Infectious bursal disease virus infection, therefore, has the potential to invoke both direct and indirect effects on the immune system. This, in turn, results in reduced response to vaccines, increased early mortality, and a significantly higher incidence of secondary opportunistic pathogens (105, 106).

Immunosuppression induced by IBDV infection is experimentally assessed by the ability or inability of the bird to mount an immune response to IBDV as well as other types of antigens following infection or vaccination. It has been repeatedly demonstrated that vaccination or infection with IBDV at an early age will result in the suppression of the humoral immune response to a number of different antigens (1, 19, 33, 35, 53, 68, 72, 100, 111, 119, 120, 121). In addition, other studies have determined that there is a reduction in natural killer cell activity (115, 117), and reduced immune response to other classes of antigens (102, 118). Challenge with IBDV which is administered to immunologically mature chickens may produce only partial immunosuppression or no immunosuppression at all (28).

Bursectomized birds are still capable of producing an immune response, but because a majority of the immune cells are no longer present, the response is extremely weak. In addition, bursectomized birds do not manifest the physical symptoms of clinical IBDV. The proposed mechanism is that there are insufficient target cells to attain viremia levels to induce lesions. The ability to produce low levels of antibody indicate that immunity in birds to infectious agents can develop, in part, from other lymphoid organs including the spleen, and thymus (36, 95).

Classic and variant serotype 1 IBDV induce different types and intensities of immunosuppression. In-vitro lymphoblast transformation assays demonstrated that the variant IBDV exerted more of an effect on the lymphoid cells, whereas the classic IBDV targeted the humoral immune response (102). Utilization of certain vaccines can also induce immunosuppression, and reflect the need to utilize IBDV vaccines judiciously (35).

Pathogenicity

Primary pathologic lesions associated with IBDV infection or vaccination of susceptible chickens are found predominantly within the bursa of Fabricius (BF). Rapid onset of lesions within the BF reflect the high concentration of target B-lymphocytes present (120). This is accompanied by the lesser involvement of other lymphoid organs, such as spleen, thymus, cecal tonsils and Peyers patches (64,118). Pathology observed for classic IBDV infection varies from that described for variant IBDV infection. Classic IBDV pathology is well characterized and will be discussed thoroughly in this section with reference to differences demonstrated by variant IBDV (21,107). To summarize, variant IBDV pathology exhibits similar lesions to the classic virus which are less severe, and can be described as highly cytolytic with rapid bursal atrophy and a minimal inflammatory response. One of the proposed mechanisms for this difference in pathology is that variant IBDV, as well as serotype 2 IBDV, induce cytopathology through the process of apoptosis (135,136).

Pathology within the chicken lymphoid system is presumed to result directly from IBDV infection of suitable target cells. Primary target cells have been identified as IgM bearing B lymphocytes, but other cells have also been implicated; they include macrophages. non-B lymphocytes, endothelial cells and reticuloendothelial cells (15,16,48,84, 91).

The BF represents a unique organ structure found exclusively in avian species. The bursa is contained within a blind pouch that is located dorsal to the cloaca. This blind pouch is connected by a short duct to the cloaca through which it receives contact with environmental antigens. Exposure to these antigens appears to be a non-specific mechanism at the control of peristaltic movement through the bursal duct due to currents created by transport of waste through the cloaca (105). The BF is divided into distinct follicular regions that can be further divided into a outer dense cortical zone filled with lymphocytes, which surrounds a loosely packed medullary zone of reticuloepithelial cells (97,106). The primary function of the BF is the development, maturation and transformation of the B-lymphocyte, and as a result the bursa strongly influences the humoral immune response of the chicken as well as other avian species (36,67).

There is a direct correlation between the degree of pathological lesions and symptoms induced by IBDV challenge and the number of susceptible cells available for infection (44,51, 66,134). This is perhaps best demonstrated by infection of birds with IBDV following removal of the bursa. Bursectomized birds have little or no antibody production, but show mild lymphocytic necrosis in the spleen and thymus. Presence of the bursa of Fabricius is not necessary to establish infection with IBDV, but it appears to be required for manifestation of the clinical infection (96).

Bursal lesions appear as early as one day following infection and are generally characterized by extensive necrosis of lymphocytes in the cortex of the bursal follicle. Phagocytosis of the necrotic lymphoid cells by the reticular cells then progresses to a severe reticuloepithelial hyperplasia with accompanied inflammation. This is followed by infiltration of heterophils, and accumulation of pyknotic debris within the follicles. As the follicles fill with cellular necrotic debris, the intrafollicular area becomes edematous (105,106). Plasma cells and pyronionphilic blast cells develop in the areas of reticuloepithelial hyperplasia and subsequently become necrotic. Initial atrophy of the bursa is followed by the rapid proliferation of the cortico medullary epithelium and the formation of mucus secreting gland (118). Following IBDV infection, the total bursal tissue surface area can be reduced in excess of 70% with little or no lymphocyte repopulation before age onset involution at approximately 12 weeks of age (108). Secondary lymphoid organs are scattered throughout the avian body. Collectively, these lymphoid tissues have more B-lymphocytes than the bursa, however, they lack the high concentration and as such reactions following IBDV infection go relatively unnoticed (27).

Surveys of tissues from IBDV infected birds utilizing the electron microscope detected morphological changes in the bursa as early as 48 hours. Epithelial microvilli of the bursa were initially reduced in number and size. As the infection progressed, there was gradual involution of the bursal follicles, followed by the development of surface erosions from the loss of epithelial cells (92).

Bursae from IBDV vaccinated birds show marked lymphocyte depletion and infiltration of mononuclear cells similar to what is described for virus challenge (28). However, controlled exposure to live virus vaccination results in overall reduction of the amount of tissue damage. Histological changes were most pronounced in groups of birds vaccinated at 28 days of age. Lesions were characterized by the loss of demarcation between the cortex and medulla, and a significant increase in the number of cells packed into follicles with additional infiltration of mononuclear cells. Depletion of cells from the medulla of the bursa was most severe by 5–7 days post vaccination (35).

Infectious bursal disease virus could be recovered from the intestine from 4–10 days PI for birds challenged at 1, 7, and 14 days. Older challenged birds (5 weeks +) highest intestinal levels were day 3–8 PI. Complement depletion was determined to be significantly lower only in the older birds (5 week +)(29). IBDV antigen can be detected in macrophages and lymphoid cells of the cecum as early as 4 hours PI (84). Other lymphoid organs are adversely affected by the presence of IBDV virus, with pathology attributed to virus specific replication in target cells.

Following IBDV infection the spleen often demonstrates reticuloendothelial cell hyperplasia in the lymphocyte beds that surround the adenoid sheath arteries, with marked splenic fibrinoid degeneration (17, 44, 114). The thymus exhibits a reduction in the cortical mass (19) while in the cecal tonsil there were loss of follicles and a decrease in the number of lymphocytes (17, 44, 114). Kidneys of infected birds demonstrate formation of homogenous casts with infiltration of heterophils and the presence of immunoglobulins (74). Post mortem examination of infected birds often demonstrates infiltration of heterophils and edema in livers associated with hepatic coagulative necrosis. Levels of interferon production increase in the kidney, lungs, thymus, spleen, and bursa following IBDV infection. Attenuated strains of IBDV similar to those utilized for vaccination only induced an increase in interferon levels in the bursa (34).

Other physical manifestations of IBDV infection do not involve the lymphoid system. Secondary pathology induced by IBDV infection is characterized by edema, congestion, hemorrhage, necrosis and heterophilic infiltration in the skeletal muscles of the chest and thigh. In addition, similar lesions have been described (74,95,96), in the intestine (114) (120) and mucosa of the proventriculus (116). Hemorrhage formation, in conjunction with IBDV infection, has also been associated with a disseminated intravascular coagulation defect (122) and the destruction of thrombocytes (138). It can be postulated that IBDV would interfere with immune reactions dependent on multiple immune structures including both the bursa and the thymus (102).

Ivanyi et al. hypothesized that immune complexes may play a role in the pathogenesis of IBDV infections, which could account for the secondary pathologic changes observed (53). Combinations of antigen, antibody and complement represent complexes that contribute to IBDV infection pathology by their physical and pharmacological properties. The lesions of acute immune complex disease typically develop in the vasculature and renal glomeruli resulting in arteritis and glomerulonephritis. Fluorescent antibody staining of infected tissue indicated the presence of gamma globulins in renal glomeruli following infection with IBDV. The presence of these immune complexes within the tissue indicate that they may influence pathogenesis associated with IBDV infection in chickens (74).

Simultaneous multiplication of IBDV and production of antibodies in the bursa may produce immune complexes with cellular damage occurring following the activation of complement, with additional involvement of increased interferon levels. Complement mediated destruction of bursal cells would result in a type of non-inflammatory lymphocyte depletion. Skeeles et al. demonstrated that complement levels increase with age, and associated the increase with an increased severity of lesions induced in older birds following infection with IBDV. It has also been demonstrated that during acute IBDV infection there is a depletion of complement in infected birds on days 3 and 5 PI, with complement levels returning to normal by day 8. Administration of hyperimmune serum during IBDV infection did not appear to increase disease severity (123,124,125).

Apoptosis has also been proposed as one of the mechanisms by which a number of viruses induce pathology. Recent studies have indicated that IBDV also utilizes this mechanism (136,137). Apoptosis is a genetically ordered sequence of events following a very specific cellular signaling stimulus in which irreparably damaged cells are disposed of, with minimal damage to surrounding cells or tissue (133).

Apoptosis should not be confused with necrosis, as each represents a totally different set of events albeit with some overlap. Cellular necrosis results from physical injury and is not in any way genetically controlled. Whereas apoptosis is a genetically predetermined deliberate cellular response to specific developmental and environmental stimuli. Injury events that produce necrosis can trigger apoptosis in response to the presence of cellular debris and inflammation. Likewise, it may be possible that induction of apoptosis could indirectly produce necrosis in some instances where cellular degeneration results from a disease process. Necrosis is typified by the destruction of cytoplasmic organelles and loss of the integrity of the plasma membrane. Apoptosis is associated with the boiling of the cytoplasm, condensation of chromatin, fractures of nuclear DNA and can be distinguished from necrosis by lack of an inflammatory response (139).

Where viruses are concerned, the inhibition of apoptosis has resulted in persistent infections, latency, or enhanced virus production. On the other hand, promotion of apoptosis has been demonstrated to facilitate virus spread and release (133,136,137,139).

Proventriculitis Syndrome

Enlargement of the proventriculus has been recognized as a problem in broiler chickens in Northwest Arkansas, as well as in other high intensity poultry producing areas throughout the United States for a number of years. The problem manifests itself at the greatest cost in the processing plant, but may also be associated with poor feed conversion.

Weakened proventriculi that are engorged with feed and digesta are subject to breakage at the point of mechanical evisceration. The contents of the proventriculus contaminate the chicken carcass, resulting in increased levels of washouts, downgrades, and condemnations.

Proventriculitis syndrome has been linked to a number of possible causes. Early considerations involved a longer fasting period before processing. However, increased fasts did not facilitate the emptying of the proventriculus. The search for a plausible explanation of this condition resulted in the determination of a number of factors that adversely affect the function, and structure of the avian proventriculus. A number of dietary components have been associated with enlarged proventriculi. Among them are: biogenic amines, lack of dietary fiber, high levels of mold toxins (37), and copper sulfate supplementation (140). In addition, a number of infectious agents have been identified as exerting an effect on the proventriculus. The pathological infectious agents identified as potential causes of proventriculitis are as follows: reovirus, Marek's virus, avian influenza, adenovirus (37) and velogenic NewCastle (vNDV) virus. However, there is no evidence, at present, that links any of the preceding factors with the syndrome currently being described.

Bayyari et al. demonstrated that proventriculitis syndrome could be reproduced utilizing an undefined homogenate of affected proventriculi collected from field birds at processing (8). The syndrome could also be reproduced utilizing a filtrate of the same homogenate, and the condition could be exacerbated by the addition of copper sulfate in the feed. Induction of the proventricular syndrome with the filtrate indicated the possibility that the causative agent involved was some type of viral agent. Additional clues indicated that the virus could, possibly be infectious bursal disease virus, as challenged birds seroconverted to IBDV (8, 9).

Further evidence that linked IBDV to this syndrome was found following IBDV challenge after vaccination against IBDV. Unvaccinated challenged control birds exhibited lesions associated with proventriculitis. The following studies were undertaken to elucidate the role of IBDV in the induction of a viral proventriculitis syndrome in chickens. In addition, a number of host and environmental factors will be investigated for the influence they exert on the incidence and severity of this syndrome.

In accordance with the present invention, variant E/1084 infectious bursal disease virus (IBDV) challenge given to specific pathogen free (SPF) chicks at 7, 14, 21, and 28 days post hatch was capable of producing microscopic lesions in the proventriculus, but was only detected in the proventriculus of birds challenged at 28 days post hatch using the AC-ELISA. Birds challenged with Variant E/1084 IBDV on 7, 14 and 21 days post hatch had lower antibody titers at 11 days post challenge than those challenged at 28 days post hatch. Antibody response to Variant E/1084 IBDV on all challenge dates was higher than antibody response to USDA/STC IBDV given at 28 days post hatch. Bursa:body weight (B:BW) ratios were significantly different for birds challenge with Variant E/1084 IBDV on days 7 and 28 post hatch at 4 days post challenge. There was evidence of early onset of bursal atrophy for these two challenge groups. On day 11 post challenge all IBDV infected groups demonstrated significant atrophy of the bursa regardless of age at challenge or challenge virus given. Proventriculus:body weight (P:BW) ratios were significantly different at 4 and 11 days post challenge in birds that received Variant E/1084 IBDV on day 7 post hatch and on day 11 post challenge in birds that received challenge on day 21 post hatch. Internal gross lesions involving the papillae were most evident in birds challenged on days 7, 14, and 28 post hatch with Variant E/1084 IBDV, and also in birds challenged on day 28 post hatch with USDA/STC IBDV.

Specific pathogen free (SPF) white leghorn chickens were challenged at 32 days post hatch with 3 different concentrations of USDA/STC IBDV and 3 different concentrations of Variant E/1084 IBDV. Birds were examined at 2, 3, 4, and 11 days post challenge for the presence of virus and lesions in the proventriculus and bursa. AC-ELISA analysis indicated the presence of infectious bursal disease virus (IBDV) was a factor of both the concentration of virus inoculum given and time post exposure. AC-ELISA analysis of the bursa reflected that the percentage of birds testing positive was a factor of time post virus exposure. Serological analysis indicated that all birds challenged with either strain of IBDV were seropositive at 11 days post challenge, and total antibody titer did not reflect the varied amounts of virus inoculum given. Microscopic lesions in the proventriculus were more pronounced in the groups receiving USDA/STC and occurred as an acute lesion and as a chronic lesion, however, there was no indication of a virus concentration effect. Microscopic lesions in the bursa were present in all IBDV challenge groups at all sampling times.

Thin section electron micrographs revealed the presence of virus like particles within the proventriculus of SPF white leghorn chickens at four days post challenge with IBDV. SPF white leghorn chickens exhibit lesions in the bursa and proventriculus following IBDV challenge. Lesion assessment, both grossly and microscopically, indicates that the USDA/STC IBDV is capable of producing the most severe effect on the proventriculus. Pathology from infectious bursal disease virus infection is exacerbated by the presence of copper sulfate supplementation in the feed. The presence of REO S-1133 virus indicated interference in the immune response or IBDV replication, as well as the number of tissue homogenates testing positive for IBDV at 4 days post challenge. Mortality was significantly increased for birds challenged with USDA/STC IBDV in the presence of copper sulfate and/or REO S-1133 virus. Birds which received dietary copper sulfate supplementation had reduced body weights at 4 days post challenge and at 11 days post challenge.

The presence of apoptotic cells in the proventriculus and bursa at 4 days post challenge with USDA/STC IBDV and Variant E/1084 IBDV was determined using a modified TUNEL fluorescent staining procedure. Specific green fluorescence was found in highest quantity in the bursa, no differences in the intensity of staining could be determined for each IBDV strain. Fluorescence was focused predominantly in the medulla and cortex of infected bursae. Proventricular fluorescent staining was found predominantly in the villi and submucosa. Fluorescent intensity of proventricular sections appeared highest in tissue sections from SPF leghorn chickens challenged with USDA/STC IBDV.

Hemolytic complement levels were decreased at 4 days post challenge in all IBDV challenge groups. Highest level of depletion was in the SPF white leghorn chickens challenged with USDA/STC IBDV. Complement levels were recovered by 6 days post challenge which corresponded with measurable levels of neutralizing antibodies against USDA/STC IBDV. IBD virus was detectable by AC-ELISA at this time also, indicating that all the components needed for the stimulation of complement mediated pathology are present and as such remain as one possible mechanism for IBDV induced tissue damage. Virus neutralizing antibodies appeared first in the SPF white leghorn chickens challenged with Variant E/DEL at 6 days post challenge. All IBDV challenged groups had measurable IgG titers at day 8, but there was a subsequent decrease in titer at day 11.

Broiler chickens challenged with USDA/STC IBDV at 35 days post challenge exhibited gross lesions in the bursa and proventriculus at 4 days post challenge in the presence and absence of copper sulfate. Antigen capture ELISA (AC-ELISA) analysis of tissue homogenates indicates that the USDA/STC IBDV was present at 4 days post challenge and was not influenced by the presence of dietary copper sulfate. Broiler chickens did produce an immune response to IBDV following challenge.

To date submissions for AC-ELISA screening of broiler flocks affected with proventriculitis have encompassed at least 46 facilities from 6 different states. Broiler chicken tissue submissions come from flocks ranging in age from 14 to 35 days post hatch. Virus immunoprecipitation following AC-ELISA screening has resulted in the isolation of at least 5 infectious bursal disease viruses of proventricular origin. Virus isolations are primarily from broiler flocks ranging in age from 22–29 days post hatch.

Inoculation of proventricular origin IBDV isolates into 28 day post hatch SPF white leghorn chickens, revealed the production of lesions associated with infectious bursal disease virus infection. At 11 days post challenge all SPF white leghorn chickens demonstrate IgG antibody titers to IBDV following screening of serum with a commercial IBDV ELISA kit.

RT/PCR-RFLP analysis of new proventricular IBDV isolates indicate that the viruses have a unique restriction enzyme pattern within a 700 bp fragment of the VP2 genomic region. The new isolates appear to share characteristics of both the Delaware variant and a more recent California IBDV isolate from the bursa.

BRIEF DESCRIPTION OF THE DRAWINGS

FIG. 23 is a diagram showing serum antibody levels from SPF white leghorn chickens challenged at 28 days post hatch with Variant E/DEL, Variant E/1084, and USDA/STC IBDV at 4, 6, 8 and 11 days post challenge.

FIG. 24 is a diagram showing hemolytic complement levels in SPF white leghorn chickens challenged at 28 days post hatch with Variant E/DEL, Variant E/1084, and USDA/STC IBDV at 4, 6, 8, and 11 days post challenge.

FIG. 31 is a diagram showing serum antibody response of SPF white leghorn chickens challenged at 28 days post hatch with USDA/STC IBDV and proventricular origin field IBDV isolates.

SECTION 1

Figure 1:
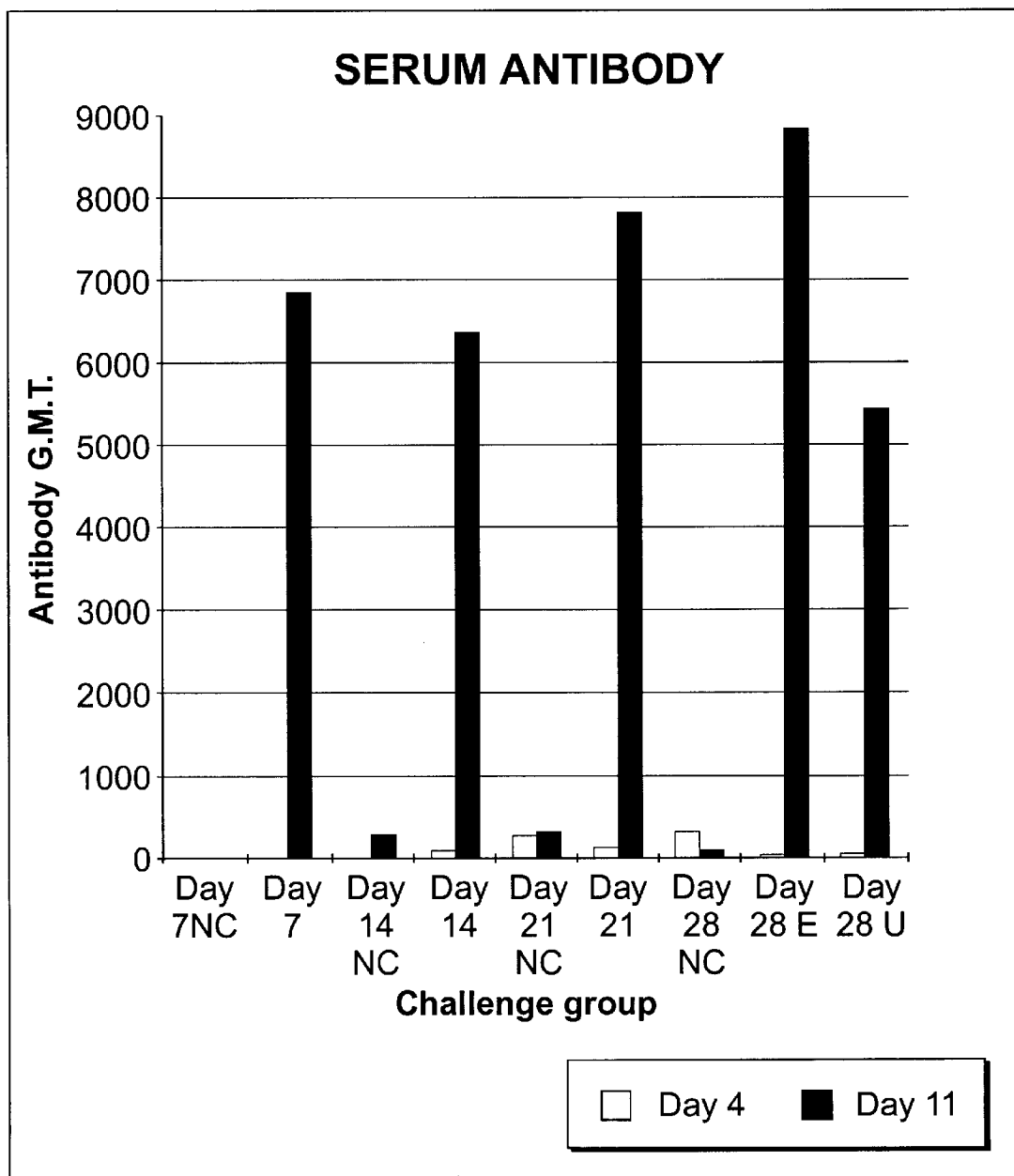
FIG. 1 is a diagram showing geometric meant titers (GMT) of SPF white leghorn chickens at 4 and 11 days post challenge with Variant E/1084 IBDV given at 7, 14, 21 and 28 days post hatch, and with USDA/STC IBDV given at 28 days post hatch only. Negative Control (NC), Variant E/1084 IBDV (E), USDA/STC IBDV (U).

DETERMINATION OF THE ROLE OF INFECTIOUS BURSAL DISEASE VIRUS STRAIN VARIANT E/1084 IN THE INDUCTION OF PROVENTRICULITIS IN SPF CHICKENS: AGE RELATED EFFECTS

SUMMARY

Variant E/1084 infectious bursal disease virus (IBDV) challenge given to specific pathogen free (SPF) chicks at 7, 14, 21, and 28 days post hatch was capable of producing microscopic lesions in the proventriculus, but was only detected in the proventriculus of birds challenged at 28 days post hatch using the AC-ELISA. Birds challenged with Variant E/1084 IBDV on 7,14 and 21 days post hatch had lower antibody titers at 11 days post challenge than those challenged at 28 days post hatch. Antibody response to Variant E/1084 IBDV on all challenge dates was higher than antibody response to USDA/STC IBDV given at 28 days post hatch. Bursa:body weight (B:BW) ratios were significantly different for birds challenge with Variant E/1084 IBDV on days 7 and 28 post hatch at 4 days post challenge. There was evidence of early onset of bursal atrophy for these two challenge groups. On day 11 post challenge all IBDV infected groups demonstrated significant atrophy of the bursa regardless of age at challenge or challenge virus given. Proventriculus:body weight (P:BW) ratios were significantly different at 4 and 11 days post challenge in birds that received Variant E/1084 IBDV on day 7 post hatch and on day 11 post challenge in birds that received challenge on day 21 post hatch. Internal gross lesions involving the papillae were most evident in birds challenged on days 7, 14, and 28 post hatch with Variant E/1084 IBDV, and also in birds challenged on day 28 post hatch with USDA/STC IBDV.

INTRODUCTION

Proventiculitis syndrome is a problem described in broiler field production birds in which the proventriculus is swollen and engorged with feed. The problem is described most often in conjunction with birds being processed at an early age (approximately 28–35 days). The syndrome is present in older birds at processing but appears to be of a much lower incidence. Withdrawal of feed prior to processing does not facilitate the emptying of the proventriculus, or alleviate the problem. At processing the enlarged proventriculus tears and the contents contaminate the carcass, requiring further washing, excessive trims, or high condemnation. It had been determined earlier that IBDV/STC was capable of inducing lesions consistent with those described for proventriculitis syndrome. It was also evident that the intensity of lesions produced following IBDV challenge was increased as the age of the birds increased (data not shown). The purpose of this experiment was to determine if Variant E/1084 IBDV was also capable of inducing the same type of lesion observed with the USDA/STC classic IBDV, and whether or not the presence and intensity of that lesion was increased as age of the birds increased.

MATERIALS AND METHODS

One hundred and fifty SPF chickens derived from fertile SPF eggs (HYVAC Inc., Adel, Iowa) were hatched at the University of Arkansas Poultry Health Laboratory Isolation Facility. Chicks were placed in negative pressure isolation units on day of hatch. Each isolator contained 20 birds, with the exception of the negative control group which contained 50 birds in order to accommodate all posting dates with age matched non-infected controls. All birds received water and the standard University of Arkansas diet formulation as specified by age ad libitum. Lighting was maintained continuously for brooding purposes throughout the entire study utilizing a 250 watt light bulb in each isolator as well as diffuse fluorescent lighting in the animal suite.

IBDV VIRUS CHALLENGE INOCULUM PREPARATION

Variant E/1084 challenge virus (Select Laboratories, Gainsville, Ga.) was prepared from stock virus (1084-E). The challenge virus aliquot was removed from the ultralow freezer (−70° C.), placed in a laminar flow hood, and thawed at room temperature. The outside of the vial was wiped with 70% ethanol to remove any surface contamination. The virus was then diluted 1:1000 in sterile deionized water. The Variant E/1084 challenge stock titer was $10^{5.6}$ TCID$_{50}$/ml . Virus challenge inoculum titer was $10^{2.6}$TCID$_{50}$/ml.

USDA/STC IBDV challenge inoculum was prepared from lot #92-1 (NVSL, Ames, Iowa) as follows: The virus was removed from the ultralow freezer (−70° C.), and thawed at room temperature in a laminar flow hood. The outside of the virus containing glass ampule was wiped with 70% ETOH, to remove any surface contamination. The ampule of virus was snapped open by wrapping the neck with a paper towel and breaking along the prescored line. The virus was then diluted 1:10 by mixing 1.5 ml of USDA/STC IBDV virus into 13.5 ml of Dulbecco's Phosphate Buffered Saline (D-PBS) (Appendix). The USDA/STC IBDV challenge virus stock titer was $10^{4.1}$ EID$_{50}$/ml. Virus challenge inoculum titer was $10^{3.1}$ EID$_{50}$/ml.

SPF BIRD CHALLENGE

Viral challenges with Variant E/1084 IBDV were staggered by age and administered to individual isolators containing 20 SPF white leghorn chickens. Challenges were administered on the following days 7, 14, 21, and 28 post hatch (PH) with the prepared inoculum as described previously. Challenge was administered to each individual bird bilaterally to the eye (30μl per eye) using an Eppendorf micropipettor (Brinkmann Inc., Westbury, N.Y.) and a sterile pipette tip (Costar Corp., Cambridge, Mass.). In addition, on day 28 PH one isolator of 20 birds was challenged with USDA/STC IBDV virus inoculum as described previously. Challenge was administered to each individual bird bilaterally to the eye (30μl per eye) using an Eppendorf micropipettor (Brinkmann Inc., Westbury, N.Y.) and a sterile pipette tip (Costar Corp., Cambridge, Mass.)

SAMPLE COLLECTION

On days 4 and 11 post challenge 10 birds were necropsied from each virus challenge group as well as an additional 10 birds from the negative control. Each bird was weighed, bled, and euthanized with $CO_2$ gas. All bursae and proventriculi were scored for the presence of gross lesions during necropsy. The bursa, spleen, and proventriculus were individually weighed and weights recorded. Tissues from each of the first five birds were cut in half, with one half being placed into 10% buffered formalin, and the other half being placed into a sterile sampling bag (Fisher Scientific, Pittsburgh, Pa.). All tissues were pooled by organ and experimental treatment group into the buffered formalin and into the sampling bags. Tissues from the remaining five birds were placed only in the sterile sampling bags. Tissues in sterile sampling bags were frozen at −20° C. for later analysis utilizing Antigen Capture ELISA (AC-ELISA), as described by Snyder et al (11).

ANTIGEN CAPTURE ELISA

AC-ELISA Plate Preparation:

Monoclonal antibody B-29 (University of Maryland, College Park, Md., Intervet Inc., Millsboro, Del.) was diluted 1:10 in ice cold sterile distilled water. The solution was then acidified by the addition of 0.4 N sulfuric acid. The acidified monoclonal solution was incubated in an ice bath for one hour at −20° C. Following incubation the acidified monoclonal antibody was diluted in 200 ml of coating buffer bringing the final dilution of monoclonal antibody to 1:10,000. ELISA optimized 96 well microtiter plates Corning #25805-96 (Corning Glass Works, Corning N.Y. 14831) were coated with 100 μl per well of a 1:10,000 dilution of monoclonal antibody B-29 (University of Maryland, College Park, Md.; Intervet, Inc., Millsboro Del.) ascitic fluid in coating buffer (Appendix). Plates were covered with individual plate sealers (Dynatech, Chantilly Va.), and incubated for 2 hours at 37° C. and then overnight at 4° C. Coated plates were washed three times with washing buffer (Appendix), with residual fluid being tapped out. Plates were allowed to air dry at room temperature and were then covered with individual plate sealers and stored at −20° C. until needed.

AC-ELISA Sample Preparation:

Infectious bursal disease virus suspect tissues were homogenized in AC-ELISA dilution buffer (Appendix) at a ratio of 1:5 or approximately 20% tissue weight to volume. Homogenization was accomplished by use of a rubber mallet, followed by the addition of the dilution buffer. One hundred fifty μl of each bursal homogenate and 300 μl of each proventricular homogenate were placed in duplicate in a 96 well round bottom plate. The concentration of the bursa tissue was adjusted by addition of 150 μl of AC-ELISA dilution buffer. There was no additional dilution to the proventriculus tissue homogenates.

AC-ELISA Analysis of Tissue Homogenates:

Monoclonal antibody coated plates were removed from −20° C. storage and allowed to come to room temperature (approximately 30 minutes). Monoclonal coated plates then received 75 μl of dilution buffer to each well. Twenty-five μl of suspect IBDV bursal tissue homogenates and 75 μl of suspect IBDV proventriculus tissue homogenates were then transferred to the AC-ELISA plate using a costar 12 well adjustable micro pipettor (Costar Corp., Cambridge, Mass.). The final concentration of bursal homogenate on the AC-ELISA plates was 1:40 and the final concentration of the proventriculus tissue homogenates was 1:10. AC-ELISA plates were incubated at 37° C. for 2 hours. Tissue samples were removed by inverting the plate, and directing the contents into a container of disinfectant. Plates were washed 3 times with washing buffer. The secondary antibody chicken anti-IBDV (SPAFAS, Storrs, Conn.) was diluted 1:150 in dilution buffer. Each well on the AC-ELISA plate received 100 μl of the secondary antibody. The AC-ELISA plate was incubated at 37° C. for 1 hour. Secondary antibody was removed and the AC-ELISA plate was washed three times with washing buffer. AC-ELISA conjugate was prepared with #14-24-06 Peroxidase labeled Affinity Purified Goat anti Chicken IgG (Kirkegaard and Perry Laboratories, Inc., Gaithersburg, Md.) to a final concentration of 0.1 μg/ml or approximately 1:200 in dilution buffer. Each well on the AC-ELISA plate received 100 μl of conjugate. AC-ELISA plates were incubated at 37° C. for 1 hour. The conjugate was removed as described earlier and plates were washed 3 times with washing buffer. The substrate was prepared by using a #50-62-00 ABTS Peroxidase Substrate System (2.2-azino-di[3-ethyl-benzthiazoline sulfonate(6)]) (Kirkegaard and Perry Laboratories, Inc., Gaithersburg, Md.). The substrate was prepared by mixing equal volumes of the 2 liquid components; ABTS and $H_2O_2$. Substrate volume added was 100 μl per well to the entire plate. The reaction was allowed to develop until there was sufficient color difference detectable by eye between the negative and positive controls. The reaction was arrested by adding 10 μl of 1% sodium dodecyl sulfate (Sigma Inc., St. Louis, Mo.). Plates were read on an EL312e Microplate Biokinetics Reader (Biotek Instruments, Winooski, Vt.) utilizing the Flock Profile™ (Kirkegaard and Perry Laboratories, Inc., Gaithersburg, Md.) software at an absorbance of 405–450. Means were calculated for the paired samples within each group and the homogenates were determined to be positive or negative based on the mean absorbances as compared to the negative and positive controls on each plate.

BLOOD SAMPLE COLLECTION AND PROCESSING

Blood samples were collected individually using 4.5 ml Sarstedt monovette™ syringes (Sarstedt, Inc., Arlington, Tex.) containing clot activating beads and 22 gauge 1½ inch needles (Becton Dickinson and Company, Rutherford, N.J. 07070). Serum was separated from the clot by centrifugation at 1000 rpm for 10 minutes using an IEC tabletop centrifuge. Serum was collected and placed in a 96 well round bottom plate (Corning Glass Works, Corning, N.Y.) format and also into Nalgene™ cryovials (Nalge Company, Rochester, N.Y.) and frozen at −20° C. until they were analyzed using the commercial KPL Infectious Bursal Disease Virus ELISA kit and the Flock Profile™ software (Kirkegaard and Perry Laboratories, Inc, Gaithersburg Md.).

HISTOPATHOLOGY

Tissues were placed in 10% buffered formalin at necropsy. Twenty-four hours later tissues were removed and manually trimmed to a thickness of ⅛ inch and placed in tissue cassettes. Tissues were dehydrated through graded alcohols, and cleared in two changes of toluene. Tissues were then infiltrated with paraffin over a 16-hour period using an autoprocessor. Following paraffin infiltration, tissues were positioned in paraffin blocks and trimmed to expose a uniform tissue face. Prepared tissue blocks were stored at −20° C. until ready to be sectioned. Sections were cut at a thickness of 5$\mu$m and floated on a water bath containing 5% gelatin before they were placed on standard 1×3 inch slides. Tissue sections were then stained using the standard method of Harris (41), for hematoxylin and eosin.

Tissues were examined microscopically for the presence of histopathological lesions induced by IBDV infection. Lesions in the proventriculus exhibited pleomorphism, lymphoid depletion and heterophil infiltration. Lesions in the bursa were predominantly lymphoid depletion with accompanied follicle degeneration Tissues were given a numerical index score based on the presence or absence of lesions as well as the intensity of the lesions. The scores ranged from a low of "0" which indicates no lesions or pathology observed to a high of "4" which indicates extensive tissue damage.

STATISTICS

All data was entered into Microsoft™ Excel (Microsoft Corp., Redmond Wash.), and were analyzed using SAS (SAS Institute Inc., Cary, N.C.) (124). Statistical significance was determined at the P<0.05 level using General Linear Models Procedure and least squared means for body weight, bursa:body weight ratios, spleen:body weight ratios, and proventriculus:body weight ratios. In addition, statistical differences were determined for means of the numerical index scores for gross lesions in the bursa and proventriculus.

RESULTS

AC-ELISA screens of tissue pools indicated that Variant E/1084 IBDV could be detected in the proventriculus (Table 1) on day 4 post challenge, only in the groups that were challenged on days 14 and 28 post hatch. Birds challenged with USDA/STC at day 28 post hatch were also positive for IBDV at 4 days post challenge in the proventriculus. AC-ELISA screens of bursal tissue pools indicated that Variant E/1084 was present in the bursa (Table 2) on day 4 post challenge, in all groups with the exception of those challenged on day 28. The bursae of birds challenged with USDA/STC were also positive for IBDV at 4 days post challenge in the bursa. On day 11 post challenge all birds tested negative for IBDV in both the proventriculus and the bursa.

Serological analysis utilizing the commercial IBDV ELISA test (FIG. 1.) indicate that all birds were negative for the presence of IBDV IgG at 4 days post challenge. However, at 11 days post challenge all IBDV challenged groups had seroconverted to IBDV. Birds challenged with Variant E/1084 IBDV on day 7 and day 14 have a lower antibody titer than birds challenged at day 21 and day 28. The antibody titer difference between the younger and older birds is not significantly different. It should also be noted that the antibody response to USDA/STC IBDV challenge given at day 28 is lower than all antibody titers of the Variant E/1084 IBDV challenge groups regardless of age at challenge.

The presence of histopathological lesions in the proventriculus from SPF chickens challenged with Variant E/1084 IBDV at 7, 14, 21 and 28 days post hatch are presented in Table 3. Data is presented as a ratio of the number of tissues that exhibit lesions of IBDV infection over the number of tissues screened. At 4 days post challenge 100% of the birds challenged with Variant E/1084 IBDV on days 14, 21, and 28 were positive for IBDV lesions. Birds challenged with Variant E/1084 IBDV at day 7 post hatch had lesions present in 85% of the birds screened at 4 days post challenge. Birds challenged with USDA/STC IBDV at day 28 post hatch had lesions in 80% of the tissues screened at 4 days post challenge. At 11 days post challenge birds who received Variant E/1084 IBDV on days 7, 14, and 28 had no lesions in the proventriculus. Birds challenged on day 21 with Variant E/1084 IBDV and on day 28 with USDA/STC IBDV had a 20% and 40% incidence of proventricular lesions respectively at 11 days post challenge. There was a 40% incidence of proventricular lesions in the negative control birds at 11 days post challenge. This may be an indication that the virus had spread from the challenged birds to the controls, however, there was no indication of the virus being present by AC-ELISA (Table 1.).

The presence of microscopic bursal lesions in birds challenged with Variant E/1084 IBDV on 7, 14, 21 and 28 days post hatch are presented in Table 4. All groups, regardless of age at challenge with Variant E/1084 IBDV, demonstrated 100% incidence of lesions in the bursa on day 4 and day 11 post challenge. SPF white leghorn chickens challenged with USDA/STC at 28 days post hatch also demonstrated 100% incidence of lesions in the bursa on day 4 and day 11 post challenge. Please note again that the negative control group from day 28 indicate the presence of lesions in 40% of the birds sampled. However, there was no evidence of IBDV virus when tissues were screened by the AC-ELISA test (Table 2).

Bursa to body weight ratios are a standard measure for IBDV infection. Table 5 shows the mean bursa:body weight ratios of SPF white leghorn chickens sampled at day 4 and day 11 following challenge on days 7, 14, 21 and 28 post hatch. Values that are placed in shaded boxes are significantly different at the $P<0.05$ confidence interval. On day 4 post challenge bursa:body weight ratios were significantly lower in the two groups challenged on day 7 and 28 with Variant E/1084 IBDV. On day 11 post challenge all groups regardless of age at challenge or the challenge inoculum are significantly smaller than the negative control.

The proventriculus: body weight ratios were also calculated for all challenge groups on 4 and 11 days post challenge and are presented in Table 6. Numerical values which are significantly different at $P<0.05$ confidence level are indicated by the shaded boxes. The experimental group challenged at 7 days post hatch exhibits significant enlargement of the proventriculus on day 4 and day 11 post challenge. SPF white leghorn chickens challenged at 21 days post hatch demonstrate a significant difference only at day 11 post challenge. All other challenge groups were not significantly different from the negative control.

Spleen: body weight ratios were also considered because variant IBDV viruses consistently produce a splenomegaly during infection. All challenge groups regardless of age at challenge, demonstrated splenomegaly with spleen:body weight ratios that were significantly higher than the negative control (Table 7). SPF white leghorn chickens challenged on days 7, 14 and 21 post hatch with Variant E/1084 IBDV also demonstrate spleen: body weight ratios that are significantly higher on day 11 post challenge than the negative control. Birds challenged with Variant E/1084 IBDV and USDA/STC at 28 days post hatch are not significantly different from the negative control on day 11 post challenge.

Gross lesion scores were determined for the proventriculus during necropsy. External (serosal) parameters evaluated were gland prominence, length of the isthmus, and hypertrophy. Internal (mucosal) parameters evaluated were impaction, papillae, and hemorrhage. All of the parameters scored with the exception of the papillae were not significantly different (data not shown). Papillae scores from day 4 and day 11 post challenge with Variant E/1084 IBDV on days 7, 14, 21 and 28 post hatch are presented in Table 8. Mean papillae scores were only significantly different on day 4 post challenge for the groups challenged on days 7, 14, and 28 post hatch with Variant E/1084 IBDV and also for the group challenged with USDA/STC IBDV at 28 days post hatch.

DISCUSSION

Variant E/1084 IBDV was determined to be present by AC-ELISA on day 4 post challenge in the bursa of all challenge ages with the exception of day 28 post hatch. In contrast, Variant E/1084 IBDV could only be found in the proventriculus on day 4 post challenge and only in birds that were challenged at day 28 post hatch. This indicates that in the younger SPF white leghorn chickens the IBDV infection was focused predominantly in the bursa. Other lymphoid areas in the chicken are not well defined at day of hatch and as birds get older the peripheral lymphoid areas become better established, thus providing the IBD virus other lymphoid targets in which to replicate. The classic USDA/STC IBDV virus challenge given at day 28 post hatch is detected in both the bursa and the proventriculus. This may indicate that the classic virus particles are more plentiful and can therefore establish a more extensive viremia. Another consideration is that tissues that test negative by AC-ELISA may reflect that these tissues were pooled and as such tissues with low levels or no levels of virus could effectively dilute tissues with high concentrations of virus to below test detectable levels.

Serological measurements indicated that all birds were still essentially seronegative 4 days post challenge and all challenged birds were seropositve by 11 days post challenge. Geometric mean titers reflect a lower antibody response to Variant E/1084 IBDV in the younger birds. This syndrome is well documented by a number of different authors, in which infection with IBDV shortly after hatch can lead to immunosuppression (1,29,34,37,536,9). However, regardless of the age of challenge, all titers to Variant E/1084 IBDV were higher than the antibody response to USDA/STC given at 28 days post hatch. The lower immune response to USDA/STC could reflect the increased levels of damage induced in the bursa by this strain as compared to the damage from Variant E/1084 IBDV infection (37, 69).

Microscopic lesions were induced in the proventriculus by both Variant E/1084 IBDV and USDA/STC IBDV on day 4 post challenge but were less severe on day 11 post challenge. Therefore, it appears that proventricular damage from IBDV infection occurs predominantly during the acute stage of the virus infection. Microscopic lesions of the bursa were found both on day 4 and day 11 in all challenged groups and were as expected for typical IBDV infection (30, 37).

Ratios which consider the bursa, proventriculus, and spleen weights in comparison to the body weight of each individual bird represent excellent indicators of the acute and chronic stage of the IBDV infection. The bursa to body weight ratio is considered a standard measure of the infection, but in this case, gave some indications that age may play a role in the intensity of the IBDV infection. Birds challenged on day 7 and day 28 post hatch with Variant E/1084 IBDV show evidence of bursal atrophy as early as four days post challenge. Whereas, birds challenged on day 14 and 21 are not significantly different from the control values obtained at 4 days post challenge, and the response is remarkably similar to what is seen with birds challenged at 28 days post hatch with USDA/STC IBDV. The possibility exists that birds challenged at two and three weeks of age have the ability to modulate the IBDV virus infection, or that this represents the period of time when lymphocyte maturation and function are at their peak performance. Modulation of the IBDV infection could also be facilitated by the presence of antibodies, but antibody titers are below detectable levels at this point.

Proventriculus to body weight ratios were significantly larger at day 4 and day 11 post challenge only in birds challenged with Variant E/1084 IBDV at day 7 post hatch. This ratio was also significantly larger in birds challenged on day 21 post hatch at day 11 post challenge. This does not correspond to the AC-ELISA results which indicate that the Variant E/1084 IBDV was present in the proventriculus only in the day 28 challenged birds. This again may be a reflection of the dilution caused by pooling of tissues. It also could reflect that proventricular enlargement is such a transient change and that it occurs so quickly that the samples were taken to late. In addition, it is important to consider that microscopic lesions are present in the proventriculus which indicate that some damage has occurred. This strongly suggests that the virus was at one time present within the tissue, but apparently at the time the sample was taken, the level of infection was below detection capabilities of the AC-ELISA test.

The spleen to body weight ratios were good indicators of the day 4 and day 11 challenge effects of the Variant E/1084 IBDV and USDA/STC IBDV viruses. Chickens challenged at day 28 post hatch with the Variant E/1084 IBDV or USDA/STC IBDV did not have spleens that were significantly larger than the negative control at 11 days post challenge. The most likely explanation for this is that at this point in the experiment the negative controls were infected, as demonstrated by the presence of lesions in 40% of the birds screened by histopathology, and since their spleens were enlarged the difference at 11 days post challenge is not detectable.

Papillae scores indicate that IBDV challenge does cause changes in the tissue of the proventriculus, and can be differentiated both grossly and microscopically. However, chickens challenged on day 21 post hatch show adverse effects only during the acute stage of the virus infection. Interestingly, lesions are present in the tissue without the detection of virus within the tissue, demonstrating that even low levels of IBDV can cause damage.

SECTION 2

DETERMINATION OF THE ROLE OF INFECTIOUS BASAL
DISEASE VIRUS STRAINS USDA/STC AND VARIANT
E/1084 ON THE INDUCTION OF LESIONS ASSOCIATED
WITH PROVENTRICULITIS: INFLUENCE OF VIRUS
CONCENTRATION AND TIME

SUMMARY

Specific pathogen free (SPF) white leghorn chickens were challenged at 32 days post hatch with 3 different concentrations of USDA/STC IBDV and 3 different concentrations of Variant E/1084 IBDV. Birds were examined at 2, 3, 4, and 11 days post challenge for the presence of virus and lesions in the proventriculus and bursa. AC-ELISA analysis indicated the presence of infectious bursal disease virus (IBDV) was a factor of both the concentration of virus inoculum given and time post exposure. AC-ELISA analysis of the bursa reflected that the percentage of birds testing positive was a factor of time post virus exposure. Serological analysis indicated that all birds challenged with either strain of IBDV were seropositive at 11 days post challenge, and total antibody titer did not reflect the varied amounts of virus inoculum given. Microscopic lesions in the proventriculus were more pronounced in the groups receiving USDA/STC and occurred as an acute lesion and as a chronic lesion, however, there was no indication of a virus concentration effect. Microscopic lesions in the bursa were present in all IBDV challenge groups at all sampling times.

INTRODUCTION

Proventriculitis syndrome is a problem within the broiler industry that results in the enlargement and an associated weakening of the walls of the glandular stomach. Affected proventriculi fail to empty following feed withdrawal prior to processing and at processing the proventriculus tears contaminating the chicken carcass with digesta and feed. The end result is an increase in the number of washouts, downgrades and condemnations.

Previous experiments at the University of Arkansas have indicated that infectious bursal disease virus (IBDV) plays a role in the induction of proventriculitis syndrome. The purpose of this experimental procedure was to determine if the amount and strain of IBD virus influences the incidence or the severity of the proventriculitis syndrome. In addition, an IBDV infection time course will be examined to determine critical periods with respect to the process of infection and the induction of lesions in the proventriculus.

MATERIALS AND METHODS

Two hundred fifty specific pathogen free (SPF) white leghorn chicks were hatched at the University of Arkansas Poultry Health Laboratory Isolation Facility. Chicks were derived from fertile SPF eggs obtained from HYVAC Inc., Adel, Iowa. Thirty-five chicks were placed in each of 7 negative pressure isolation cages on day of hatch. All birds received the standard University of Arkansas diet formulation as specified by age and breed and along with water was provided ad libitum. Lighting was maintained continuously for brooding purposes throughout the entire study utilizing a 250 watt incandescent light bulb. Birds were maintained under isolation until they reached the age of 32 days post hatch.

IBDV CHALLENGE INOCULUM PREPARATION

USDA/STC IBDV lot #92-1 was obtained from the National Veterinary Services Laboratory (NVSL) in Ames, Iowa. The virus was maintained at the University of Arkansas Poultry Health Laboratory Isolation Facility at −70° C. until needed. Two ampules of virus were removed from the ultralow freezer and thawed at room temperature in a laminar flow hood. The outside of the virus ampule was wiped with 70% ETOH, to remove any surface contamination. The ampule of virus was snapped open by wrapping the neck with a paper towel and breaking along the prescored line. The contents of the two separate IBDV ampules were combined and mixed thoroughly to make the IBDV stock. Two virus inoculums were prepared from the IBDV stock. The first virus inoculum preparation was undilute, and 1.5 ml of USDA/STC IBDV were transferred to a sterile 15 ml conical tube. The second IBDV preparation was as per NVSL instructions in which 1.5 ml of lot # 92-1 USDA/STC IBDV were diluted in 13.5 ml of Dulbecco's Phosphate Buffered Saline (D-PBS). The third USDA/STC IBDV virus challenge was achieved by utilizing the second IBDV preparation and administering less volume per bird. The titer of the USDA/STC IBDV virus was previously determined to be $10^{4.1}$ $EID_{50}$/ml.

The Variant E/1084 strain IBDV challenge virus (Select Laboratories, Gainsville, Ga.) was prepared from stock virus. The challenge virus aliquot was removed from the ultralow freezer (−70° C.), placed in a laminar flow hood, and thawed at room temperature. The outside of the cryovial tube was wiped with 70% ETOH prior to opening to remove any surface contamination. The virus was then diluted 1:100 and 1:1000 in sterile deionized water. The titer of the IBDV Variant E/1084 challenge stock virus was $10^{5.6}$ $TCID_{50}$/ml. Virus challenge inoculum titers were as follows: 1:100 1084-E=$10^{3.6}$ $TCID_{50}$/ml and for the 1:1000 1084-E=$10^{2.6}$ $TCID_{50}$/ml.

SPF BIRD CHALLENGE

All SPF white leghorn chickens were maintained under isolation until they reached 32 days post hatch. Three isolation cages of birds were challenged with one of three different amounts of each IBDV virus strain. Infectious bursal disease virus challenges were administered bilaterally to each eye using an Eppendorf pipettor (Brinkmann, Inc., Westbury, N.Y.) and a sterile pipette tip (Costar Corp., Cambridge, Mass.). Virus inoculum volumes were adjusted to reduce or increase the number of virus particles given to each bird as outlined as in Table 9. Viral inoculums were diluted and administered in different volumes in order to standardize the amount of virus given per bird. Volumes administered and dilutions prepared were based solely on the predetermined infectivity titers provided with each challenge virus. Comparison of the two IBDV strains should be relegated to paired groups that are identified by a letter designation in the final column of Table 9.

SAMPLE COLLECTION

On days 2, 3, 4 and 11 post challenge 8 SPF white leghorn chickens were necropsied from each virus strain challenge group and also from the negative control. Each bird was weighed, bled, and euthanized by $CO_2$ asphyxiation. All birds were necropsied at which time the bursae and proventriculi were scored for the presence of gross lesions. The bursa, spleen and proventriculus were weighed individually and results recorded. Individual tissues from each bird were cut in half, with one half being placed into 10% buffered formalin, and the other half being placed into an individual sterile sampling bag (Fisher Scientific, Pittsburgh. Pa.). Tissues in sterile sampling bags were frozen at −20° C. for later analysis utilizing IBDV Antigen Capture ELISA (AC-ELISA) as described by Snyder et al (138).

ANTIGEN CAPTURE ELISA PROCEDURE

AC-ELISA test plates were prepared as described earlier in Section 1. Tissues were homogenized in AC-ELISA dilution buffer at a ratio of 1:5 tissue weight to volume. Homogenates were analyzed in duplicate against monoclonal B-29 (University of Maryland, College Park, Md.; Intervet, Inc., Millsboro Del.) AC-ELISA plates as described earlier in Section 1. Plates were read and means were calculated for the paired samples within each group and the homogenates were determined to be positive or negative based on the mean absorbance values as compared to the negative and positive controls on each plate.

BLOOD SAMPLE COLLECTION AND PROCESSING

Blood samples were collected individually using 4.5 ml Sarstedt monovette™ syringes (Sarstedt, Inc., Arlington, Tex.) that contain clot activating beads and 22 gauge 1 ½ inch needles (Becton Dickinson and Company, Rutherford, N.J. ). Serum was separated from the clot by centrifugation at 1000 rpm for 10 minutes using an IEC tabletop centrifuge and placed in both a 96 well round bottom plate (Corning Glass Works, Corning N.Y.) and into Nalgene™ cryovials (Nalge Company, Rochester, N.Y.). All serum samples were frozen at −20° C. until they were analyzed using the commercial KPL Infectious Bursal Disease Virus ELISA Kit and the Flock Profile™ software (Kirkegaard and Perry Laboratories, Inc., Gaithersburg, Md.).

HISTOPATHOLOGY

Tissues were placed in buffered formalin at necropsy, and processed twenty-four hours later by the method described in Section 1 (55). Tissues were examined for the presence of histopathological lesions induced by IBDV infection. Lesions in the lamina propria of the proventriculus were predominantly pleomorphism of the lymphoid cells in the mucosa along with lymphocyte depletion. Lesions in the bursa were predominantly lymphoid depletion with accompanied follicle degeneration.

Tissues were given a numerical index score based on the presence or absence as well as the intensity of the lesions present. The score ranged from a low of "0" which indicates no lesions or pathology observed to a high of "4" which indicates extensive tissue damage.

STATISTICS

All data was entered into Microsoft™ Excel (Microsoft Corp., Redmond, Wash.) and was analyzed using SAS (124) (SAS Institute Inc., Cary N.C.) Statistical significance was determined at the $P<0.05$ level using General Linear Models Procedure and least squared means for body weight, bursa: body weight ratios, spleen: body weight ratios, and proventriculus: body weight ratios. In addition, statistical differences were determined for means of the numerical index scores for gross lesions in the bursa and proventriculus.

RESULTS

AC-ELISA analysis of individual proventricular tissue homogenates harvested at 2, 3, 4, and 11 days post challenge with USDA/STC IBDV revealed that IBDV detection was variable and dependent on the day post challenge in which samples were obtained. SPF white leghorn chickens challenged with USDA/STC IBDV 0.5× concentration were 12.5% positive at 2 days, 75% positive at 3 days, and 33% positive at 4 days post challenge (Table 10). SPF white leghorn chickens challenged with USDA/STC IBDV 1× concentration were 50% positive at 2 days, 88% positive at 3 days, and 80% positive at 4 days post challenge (Table 10). SPF white leghorn chickens challenged with USDA/STC IBDV 1× concentration were negative at 2 and 4 days, and 100% positive at 3 days post challenge (Table 10). All SPF white leghorn chickens challenged with USDA/STC IBDV tested negative by AC-ELISA for proventricular tissue homogenates harvested at 11 days post challenge regardless of the concentration of IBDV virus given (Table 10).

Individual proventricular homogenates from SPF white leghorn chickens challenged with Variant E IBDV were analyzed by AC-ELISA at 2, 3, 4 and 11 days post challenge at three different viral challenge concentrations. Levels of IBDV detection varied with the concentration given and the day on which samples were obtained. SPF white leghorn chickens challenged with Variant E IBDV 1× concentration were 88% positive at 2 days, 63% positive at 3 days, and 38% positive at 4 days post challenge (Table 10). SPF white leghorn chickens challenged with Variant E IBDV 2× concentration were 25% positive at 2 days, 38% positive at 3 days, and 13% positive at 4 days post challenge (Table 10). SPF white leghorn chickens challenged with Variant E IBDV 20× concentration were 88% positive at 2 and 3 days, and negative at 4 days post challenge (Table10). All SPF white leghorn chickens challenged with Variant E IBDV tested negative by AC-ELISA for proventricular tissue homogenates at 11 days post challenge regardless of the level of IBDV challenge given (Table 10).

Individual bursal tissue homogenates from SPF white leghorn chickens challenged with USDA/STC IBDV were analyzed with AC-ELISA at 2, 3, 4, and 11 days post challenge at three different concentrations (Table 11). SPF white leghorn chickens challenged with USDA/STC IBDV 0.5× concentration were 100% positive at 2 days, 86% positive at 3 days, and 100% positive at 4 days post challenge. SPF white leghorn chickens challenged with USDA/STC IBDV 1× concentration were 100% positive at 2, 3 and 4 days post challenge. SPF white leghorn chickens challenged with USDA/STC IBDV 10× concentration were 38% positive at 2 days, and 100% positive at 3 and 4 days post challenge. All SPF white leghorn chickens challenged with USDA/STC IBDV tested negative by AC-ELISA for bursal homogenates collected at 11 days post challenge regardless of IBDV concentration given.

Individual bursal tissue homogenates from SPF white leghorn chickens challenged with Variant E IBDV were analyzed with AC-ELISA at 2, 3, 4 and 11 days post challenge at three different virus concentrations (Table 11). SPF white leghorn chickens challenged with Variant E IBDV 1× concentration were 100% positive at 2 and 3 days, and 13% positive at 4 days post challenge. SPF white leghorn chickens challenged with Variant E IBDV 2× concentration were 13% positive at 2 days, 50% positive at 3 days, and 88% positive at 4 days post challenge. SPF white leghorn chickens challenged with Variant E IBDV 20× were 75% positive at 2 days, 88% positive at 3 days, and 100% positive at 4 days post challenge. All SPF white leghorn chickens challenged with Variant E IBDV tested negative for bursal homogenates collected at 11 days post challenge regardless of the IBDV concentration given.

Figure 2:
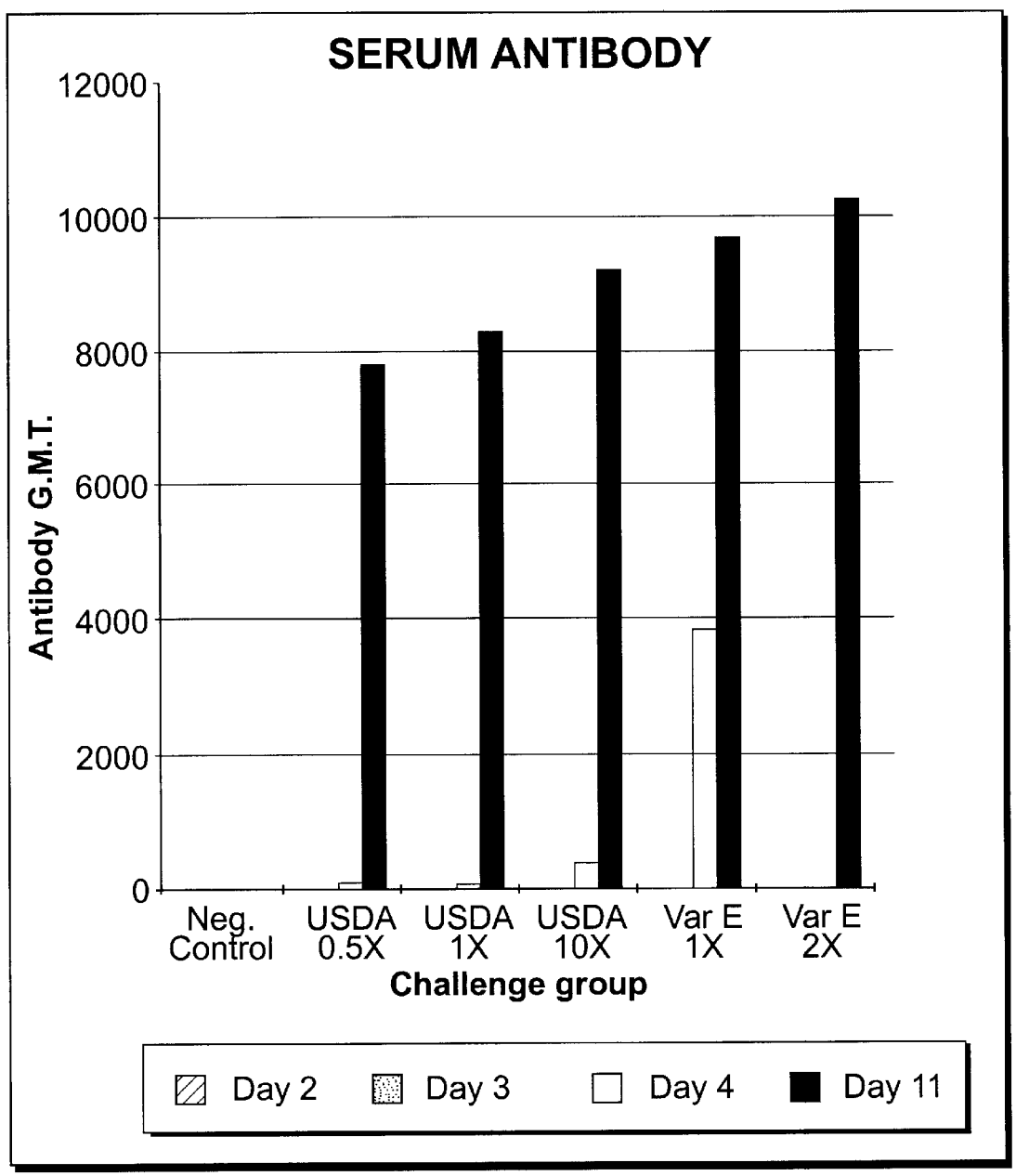
FIG. 2 shows the serological response in white leghorn chickens challenged at 32 days post hatch with USDA/STC IBDV and Variant E/1084 IBDV at 2, 3, and 11 days post challenge.

Serological analysis of all IBDV challenge groups are found in FIG. 2. Antibody titers were negative on days 2, 3, and 4 post challenge with all SPF white leghorn chickens challenged with USDA/STC IBDV. However, all SPF white leghorn chickens challenged with USDA/STC IBDV were seropositive at 11 days post challenge. Antibody titers to USDA/STC IBDV increased slightly with respect to the original concentration of virus given at challenge but were not significantly different. Antibody titers were negative on day 2 post challenge with all SPF white leghorn chickens challenged with Variant E/1084 IBDV. On day 3 post challenge, there is a small increase in titer with birds that received the 1× Variant E/1084 IBDV challenge concentration. On day 4 post challenge, there is a significant increase in the antibody titer with birds challenged with the 1× Variant E/1084 IBDV. All SPF white leghorn chickens challenged with Variant E/1084, IBDV were seropositive at 11 days post challenge, with no significant differences in final immune titer between challenge groups.

Microscopic lesions in the proventriculus were found at 2, 3, and 4 days post challenge with both the USDA/STC IBDV, and Variant E/1084 IBDV (Table 12). The incidence level of lesions varied with the challenge concentration given and the time at which the sample was taken. Incidence levels of proventricular lesions following challenge with USDA/STC IBDV at 2 days post challenge were 80%, 20%, and 20% with respect to the increasing virus inoculum. Incidence levels of proventricular lesions at 3 days post challenge of 100% for all challenge groups. Incidence levels of proventricular lesions were 100%, 40%, and 40% with respect to increasing USDA/STC IBDV inoculum. All SPF white leghorn chickens at 11 days post challenge with USDA/STC IBDV regardless of the concentration given were negative for the presence of micros copic lesions in the proventriculus (Table 12).

Microscopic lesions present in the proventriculus of SPF white leghorn chickens challenged with Variant E IBDV at 2 days post challenge were present at incidence levels of 60%, 0%, and 20% with respect to increasing viral inoculum. SPF white leghorn chickens at 3 days post challenge with Variant E IBDV demonstrated proventricular lesion levels of 50%, 20%, and 100%, with respect to increasing viral inoculum. At 4 days post challenge, proventricular lesion levels following challenge with Variant E/1084 IBDV were 40%, 80%, and 60% with respect to increasing virus inoculum. By day 11 post challenge with Variant E/1084 IBDV all challenged groups regardless of the virus inoculum given showed no evidence of lesions in the proventriculus (Table 12).

Microscopic lesions in the bursa at 2 days post challenge with USDA/STC IBDV were 80%, 40%, and 20% with respect to increasing virus inoculum. SPF white leghorn chickens at 3, 4, and 11 days post challenge with USDA/STC IBDV indicate that all challenge groups demonstrated 100% incidence of lesions in the bursa (Table 13).

Microscopic lesions in the bursa at 2 days post challenge with Variant E/1084 IBDV were 100%, 40%, and 40% with respect to increasing virus inoculum. At 3 days post challenge with Variant E/1084 IBDV, bursal lesions were found in 100% of the birds in the 1× and 20× challenge groups, whereas the 2× challenge group had an incidence of only 40%. At 4 and 11 days post challenge 100% of the SPF white leghorn chickens challenged with Variant E/1084 IBDV demonstrated lesions in the bursa regardless of the virus inoculum given (Table 13).

Proventiculus to body weight ratios (P:BW) were only significantly different for birds challenged with the USDA/STC IBDV virus at 2 days post challenge with the 0.5× and 10× virus inoculums, and for all USDA/STC IBDV challenge groups at 11 days post challenge. At 2 days post challenge, statistical differences were significantly smaller, and at day 11 post challenge differences were significantly larger than the negative control. There were no differences noted for the SPF white leghorn chickens challenged with Variant E/1084 IBDV at any challenge level or at any day post challenge (Table 14).

Bursa to body weight ratios (B:BW) demonstrated a significant reduction in size at 4 days post challenge for SPF white leghorn chickens challenged with Variant E/1084 IBDV given at the 1× and 20× concentration. All challenge groups, regardless of virus inoculum or IBDV strain type, were significantly smaller at 11 days post challenge (Table 15).

Spleen to body weight ratios (S:BW) were significantly different at 2 days post challenge with the Variant E/1084 IBDV challenge given at 1× concentration. All challenge groups were significantly larger at 3 and 4 days post challenge regardless of virus inoculum or strain of IBDV given. On day 11 post challenge no significant differences were noted for any of the IBDV challenge groups with respect to strain or amount of inoculum given (Table 16).

DISCUSSION

AC-ELISA demonstrated that challenge with different levels of USDA/STC IBDV influences the presence of virus and the intensity of lesions in the proventriculus at different time intervals post challenge. However, this appears to be a function of the acute infection only as all challenge groups test negative by day 11 post challenge. SPF white leghorn chickens that received the lower concentration of USDA/STC IBDV inoculum had a gradual increase in the number of birds that test positive on each successive day, whereas SPF white leghorn chickens that received the 10× USDA/STC IBDV tested positive in the proventriculus only on day 3 post challenge. This may be related to a phenomenon previously described by a number of authors in which high virus dosage interferes with the normal replication of the virus (7, 19). Similar analysis of bursal homogenates from the same SPF white leghorn chickens indicated that groups which received the lower challenge inoculums show a gradual increase in the number of positive samples. SPF white leghorn chickens that received the 10× challenge show low levels of virus at 2 days post challenge and progress to 100% level at day 3 and 4 post challenge.

Microscopic lesions in the proventriculi were of higher incidence SPF white leghorn chickens that received the 1× concentration of USDA/STC IBDV at 2 days post challenge. However, tissue samples screened on days 3 and 4 post challenge indicated no influence from the amount of virus inoculum given. This effect is also seen in the incidence of bursal lesions in SPF white leghorn chickens that received the 1× concentration of USDA/STC at 2 days post challenge; the effect disappears on day 3 and day 4 post challenge.

AC-ELISA analysis of proventricular homogenates at 2, 3, 4, and 11 days post challenge with Variant E/1084 IBDV indicates both a time and concentration effect. SPF white leghorn chickens that received the 1× concentration of Variant E/1084 IBDV have an incidence level of 88% at 2 days post challenge and then show a gradual decline in the number of positive samples. SPF white leghorn chickens challenged with the 2× Variant E/1084 show a slight increase in the number of positives from day 2 to day 3, but by day 4 the incidence was lower. Interestingly, these birds demonstrate fewer positive tissue homogenates than the 1× challenge group, even though receiving twice as much virus. SPF white leghorn chickens challenged with the 20× concentration of Variant E/1084 IBDV were initially equivalent with the 1× dosage at 2 days post challenge, but virus presence does not decline until day 4 post challenge. Analysis of bursal homogenates taken from the same birds followed along similar trends as far as virus challenge concentration were concerned. The 1× challenge group appears to be declining in the number of tissue positives while the 2× and 20× groups appear to be increasing.

Microscopic lesions of the proventriculus following challenge with Variant E/1084 IBDV did not correlate well with any of the challenge groups when compared to AC-ELISA results. At 2 days post challenge the relationship between virus concentration and the level of lesions present appears to be inverse in that the lowest challenge concentration has the highest incidence of lesions present in the proventriculus. No discernible pattern was determined for the different virus concentration groups on day 3 post challenge with Variant E/1084 IBDV. Microscopic lesions of the bursa following challenge with Variant E/1084 IBDV do not appear to be a function of virus concentration, however, the lesion incidence level increased over time with all challenge groups.

Significant differences in the proventriculus to body weight ratios were only noted in groups which received USDA/STC IBDV. The effect appears to have two separate manifestations, because during the acute infection, proventriculi are significantly smaller than the negative control but during the chronic infection, the proventriculus enlarges.

Bursa to body weight ratios indicate that atrophy begins as early as day 4 for one group of SPF white leghorn chickens challenged with Variant E/1084 IBDV. However, there appears to be no effect based on challenge concentration or IBDV strain utilized.

Spleen to body weight ratios indicate that splenomegally is present in all groups on days 3 and 4 post challenge. Again the 1× concentration Variant E/1084 IBDV shows an effect by 2 days post challenge. This challenge group is highly suspicious in that it consistently does things earlier than the other challenge groups. It is suspected that this group may have already been incubating the virus when the actual challenge was given.

Serological measurements on days 2, 3, 4, and 11 indicate that all SPF white leghorn challenge groups seroconverted by day 11 post challenge. The chickens challenged with Variant E/1084 IBDV show a slight response on day 3 post challenge, and in the case of the 1× challenge group a most noticeable spike in antibody titer at day 4 post challenge. This is a clear indication that these birds were possibly incubating the IBDV virus earlier than when challenged. Attempts were made to try to determine if these chickens were incubating another serotype as well as Variant IBDV. Incorporation of specific monoclonals to differentiate standard from variant viruses using the AC-ELISA gave mixed results, in that some of the tissues harvested tested as standard IBDV and others tested as Variant IBDV, while still others tested completely negative (data not shown).

In the assessment of virus effects on the proventriculus based on different IBDV strains, it would appear that the USDA/STC IBDV strain exerts more of an effect on the proventriculus than Variant E/1084 IBDV. The effects seen do not appear to be in any way linked to the concentration of virus present but is more a factor of time elapsed post exposure. Each IBD virus strain could also be demonstrating different host cell preferences based on their passage histories in cell culture and eggs. Also, it should be noted that two observations were noticed with the USDA/STC IBDV; during the acute phase there is a significant reduction in the size of the proventriculus, and in the chronic phase there is a significant enlargement of the proventriculus.

SECTION 3

THE INTERACTION OF INFECTIOUS BURSAL DISEASE VIRUS, REO VIRUS, AND COPPER SULFATE IN THE PRODUCTION OF LESIONS ASSOCIATED WITH PROVENTRICULITIS IN SPF WHITE LEGHORN CHICKENS

SUMMARY

Thin section electron micrographs revealed the presence of virus like particles within the proventriculus of SPF white leghorn chickens at four days post challenge with IBDV. SPF white leghorn chickens exhibit lesions in the bursa and proventriculus following IBDV challenge. Lesion assessment, both grossly and microscopically, indicates that the USDA/STC IBDV is capable of producing the most severe effect on the proventriculus. Pathology from infectious bursal disease virus infection is exacerbated by the presence of copper sulfate supplementation in the feed. The presence of REO S-1133 virus indicated interference in the immune response or IBDV replication, as well as the number of tissue homogenates testing positive for IBDV at 4 days post challenge. Mortality was significantly increased for birds challenged with USDA/STC IBDV in the presence of copper sulfate and/or REO S-1133 virus. Birds which received dietary copper sulfate supplementation had reduced body weights at 4 days post challenge and at 11 days post challenge.

INTRODUCTION

Proventriculitis syndrome has been described in broiler chickens from a number of geographical regions. This syndrome is characterized by an enlargement of the proventriculus, accompanied by feed impaction, and structural weakness of the organ. Affected birds can be either normal or underweight at processing, with either a high or normal feed conversion efficiency. Problems can occur at the processing plant with breakage of the proventriculus during mechanical evisceration and contamination of the carcass with digesta and feed. This results in an increased number of washouts, slowed or stopped processing lines, excessive trims, and higher than normal levels of condemnation. This proventriculitis syndrome has been linked to a number of environmental, nutritional, genetic, and infectious causes (38).

Recent studies completed at the University of Arkansas indicate that acute infectious W bursal disease virus (IBDV) infection that occurs between days 21–35 can produce lesions in the proventricular mucosa. The proventriculitis induced by IBDV alone does not exactly mimic what is observed in field situations, but studies indicate that IBDV may play the role of a facilitator, and thus presents an opportunity for other agents present in the chicken house environment (and in the chicken) to exert an effect, and as such predisposes affected birds to the possibility of secondary infections.

This study was undertaken to determine the effect on the proventriculus of two different IBD (USDA/STC) (Variant E/1084) virus challenges, in the presence of respiratory enteric orphan (REO) virus strain S-1133, when administered at 28 days post hatch. In addition, the mixed virus challenge was further complicated by the presence or absence of a common feed additive, copper sulfate given at the rate of 1 lb/ton.

MATERIALS AND METHODS

Four hundred SPF white leghorn chickens derived from fertile SPF eggs (HYVAC inc. Adel, Iowa) were hatched at the University of Arkansas Poultry Health Laboratory Isolation Facility. Thirty chicks were placed in each negative pressure isolation cage on day of hatch. All birds received water and the standard University of Arkansas diet formulation as specified by age and breed ad libitum. Chicks given the 1 lb/ton copper sulfate dietary supplement received it beginning on day 1 and throughout the entire study. Lighting was en maintained continuously for brooding purposes throughout the entire study utilizing a 250 watt incandescent light bulb in each isolator.

IBDV VIRUS CHALLENGE INOCULUM PREPARATION

The Variant E/1084 Strain IBDV challenge virus (Select Laboratorin, Gainsville, Ga.) was prepared from stock virus. The challenge virus aliquot was removed from the w ultralow freezer (−70° C.), placed in a laminar flow hood, and thawed at room temperature. The outside of the vial was wiped with 70% ethanol to remove any surface contamination. The virus was then diluted 1:1000 in sterile deionized water. The Variant E/1084 challenge stock virus titer was $10^{5.6}$ $TCID_{50}$/ml. Virus challenge inoculum titer was $10^{2.6}$ $TCID_{50}$/ml.

USDA/STC IBDV challenge inoculum was prepared from lot #92-1 (NVSL, Ames IA) as follows: The virus was removed from the ultralow freezer (−70° C.), and thawed at room temperature in a laminar flow hood. The outside of the virus containing glass ampule was wiped with 70% ETOH, to remove any surface contamination. The ampule of virus was snapped open by wrapping the neck with a paper towel and breaking along the prescored line. The virus was then diluted 1:10 by mixing 1.5 ml of USDA/STC IBDV virus into 13.5 ml of Dulbecco's Phosphate Buffered Saline (D-PBS) (Appendix). The USDA/STC IBDV challenge stock virus titer was $10^{4.1}$ $EID_{50}$/ml. USDA/STC IBDV virus challenge inoculum titer was $10^{3.1}$ $EID_{50}$/ml.

REO virus strain S-1133 was prepared from a viral stock maintained at the Poultry Health Laboratory Isolation Facility. The cryovial containing a yolk suspension of the 8th egg passage of REO virus S-1133 was removed from the ultralow freezer storage (−70° C.) and allowed to thaw at room temperature in a laminar flow hood. The outside of the vial was wiped with 70% ethanol to remove any surface contamination. The cryovial was then opened and 0.1 ml of the virus containing yolk suspension was diluted to 1:1000 in 99.9 ml of sterile D-PBS. The REO virus strain S-1133 stock virus titer was $10^{6.8}$ $EID_{50}$/ml. REO virus challenge inoculum titer was $10^{4.8}$ $EID_{50}$/ml.

SPF BIRD CHALLENGE

SPF white leghorn chickens were challenged on day 28 post hatch (PH) with Variant E/1084 IBDV, USDA/STC IBDV, and/or REO virus S1133 with prepared inoculums as described previously. Infectious bursal disease virus challenge was administered to each individual bird bilaterally to the eye (30 μl per eye) using an Eppendorf micropipettor (Brinkmann Inc., Westbury, N.Y.) and a sterile pipette tip (Costar Corp., Cambridge, Mass.). REO virus S-1133 challenge inoculum was given at a rate of 0.1 ml per individual bird and was administered orally using an Eppendorf micropipettor (Brinkmann Inc., Westbury, N.Y.) and a sterile pipette tip (Costar Corp., Cambridge, Mass.). Experimental groups and challenge inoculums are given in Table 17.

SAMPLE COLLECTION

On days 4 and 11 post challenge 10 birds were necropsied from each virus challenge group and an additional 10 birds from the negative control. Each bird was weighed, bled, and euthanized by $CO_2$ asphyxiation. All birds were necropsied at which time the bursa, and proventriculus were scored for the presence of gross lesions. The bursa, spleen, and proventriculus were individually weighed and results recorded. Tissues from each of the birds were cut in half, with one half being placed into 10% buffered formalin, and the other half being placed into a sterile sampling bag (Fisher Scientific, Pittsburgh, Pa.). Tissues in sterile sampling bags were frozen at −20° C. for later analysis utilizing IBDV Antigen Capture ELISA(AC-ELISA), as described by Snyder et al (138).

In addition, proventriculus samples were collected for electron microscopic evaluation for the presence of USDA/STC IBDV and Variant E/1084 IBDV at 4 days post challenge. Tissue samples from the papillae region of the proventriculus were collected at necropsy and manually trimmed to approximately 2 $mm^2$. Tissue specimens were fixed in a modified Karnovsky's fixative (74) containing 2% paraformaldehyde and 2.5% glutaraldehyde in 0.05 M cacodylate buffer, pH 7.2. Tissues were then post-fixed in 1% osmium tetroxide in 0.05 M cacodylate buffer, pH 7.2. Tissues were stained overnight in 0.5% aqueous uranyl acetate, dehydrated through a graded ethanol series, and embedded in Spurr's medium (143).

Thin sections were cut with a glass knife, captured on a 300 mesh copper grid and stained with 2% aqueous uranyl acetate followed by lead citrate. Grids were examined for the presence of IBDV using a JEOL 100 CX electron microscope.

ANTIGEN CAPTURE ELISA PROCEDURE

AC-ELISA test plates were prepared as described earlier in Section 1. Tissues were homogenized in AC-ELISA dilution buffer at a ratio of 1:5 tissue weight to volume. Homogenates were analyzed in duplicate against monoclonal B-29 (University of Maryland, College Park, Md.; Intervet Inc., Millsboro Del.) AC-ELISA plates as described earlier in Section 1. Plates were read and means were calculated for the paired samples within each group and the homogenates were determined to be positive or negative based on the mean absorbance values as compared to the negative and positive controls on each plate.

BLOOD SAMPLE COLLECTION AND PROCESSING

Blood samples were collected individually using 4.5 ml Sarstedt monovette™ syringes (Sarstedt, Inc., Arlington, Tex.) containing clot activating beads and 22 gauge, 1½ inch needles (Becton Dickinson and Company, Rutherford, N.J.). Serum was separated from the clot by centrifugation at 1000 rpm for 10 minutes using an IEC tabletop centrifuge. Serum was collected and placed in both a 96 well round bottom plate (Corning Glass Works, Corning N.Y.) and into Nalgene™ cryovials (Nalge Company, Rochester, N.Y.). All serum samples were frozen at −20° C. until they were analyzed using the commercial KPL Infectious Bursal Disease Virus ELISA Kit and the Flock Profile™ software (Kirkegaard and Perry Laboratories, Inc., Gaithersburg, Md.).

HISTOPATHOLOGY

Tissues were placed in buffered formalin at necropsy, and processed twenty-four hours later by the method described in Section 1 (55). Tissues were examined for the presence of histopathological lesions induced by IBDV infection. Tissues were given a numerical index score based on the presence or absence as well as the intensity of the lesions present. The score ranged from a low of "0" which indicates no lesions or pathology observed to a high of "4" which indicates extensive tissue damage.

FEED ANALYSIS

Feed samples were pulled at the end of the study and sent for analysis to establish that the two diets varied only in the different levels of copper sulfate present. Feed samples were analyzed at the Center of Excellence for Poultry Science, Central Analytical Laboratory. The diet without copper sulfate supplementation contained 22.3% protein, 89.0% dry matter, 5.6% ash, and 17.44 ppm copper. The diet with copper sulfate supplementation contained 22.6% protein, 89.5% dry matter, 5.6% ash, and 95.87 ppm copper.

STATISTICS

All data was entered into Microsoft™ Excel (Microsoft Corp., Redmond, Wash.). and were analyzed using SAS (10) (SAS Institute Inc., Cary, N.C.). Statistical significance was determined at the $P<0.05$ level using General Linear Models Procedure and least squared means for body weight, bursa: body weight ratios, spleen: body weight ratios, and proventriculus: body weight ratios. In addition, statistical differences were determined for means of the numerical index scores for gross lesions in the bursa and proventriculus.

RESULTS

Figure 3:
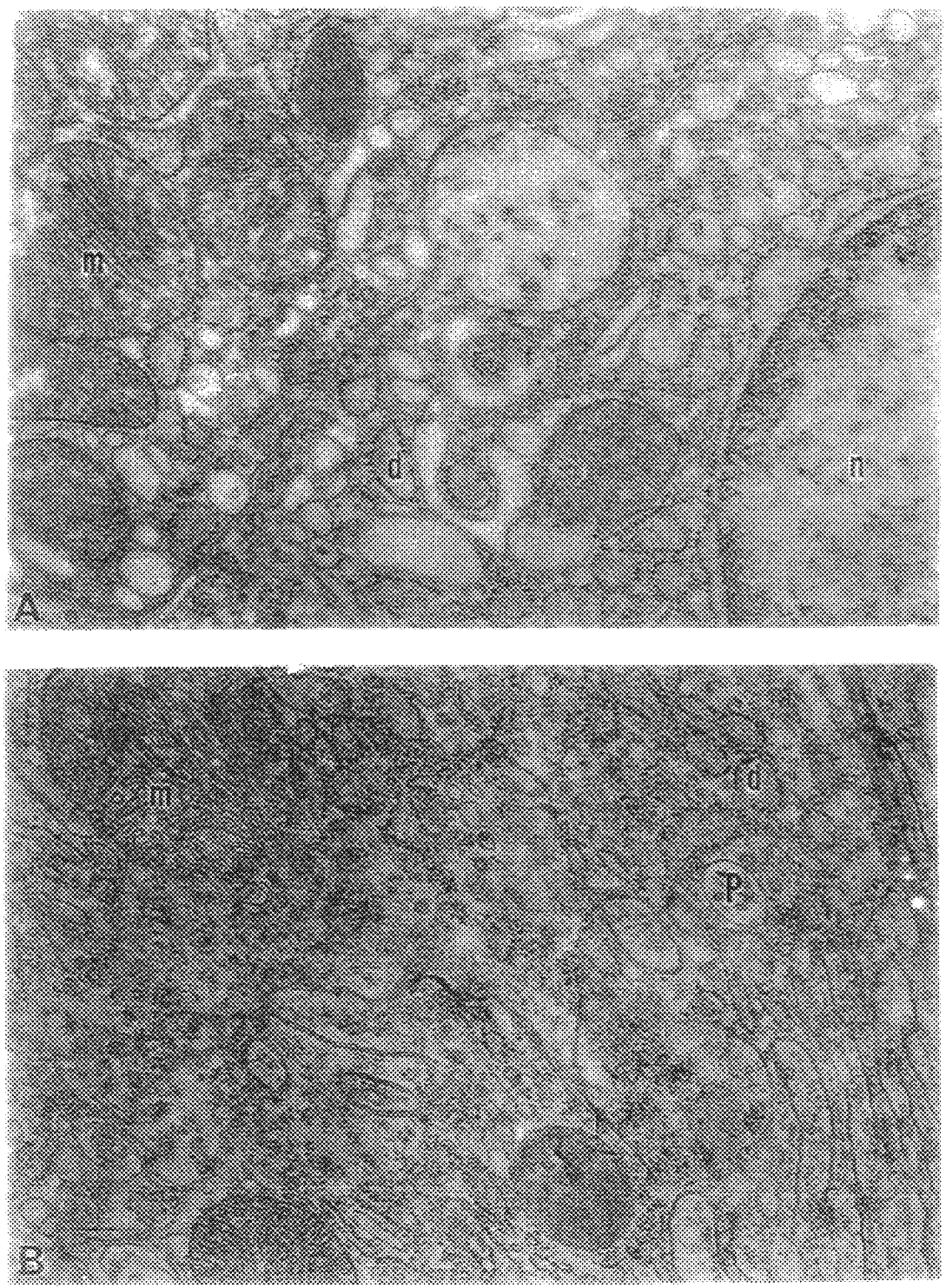
FIG. 3 shows proventricular sections from SPF white leghorn chickens at 32 days post hatch from negative control (A) and negative control+copper sulfate (B) experimental groups, with normal cellular structure. Mag. 30,000×. Note the presence of multiple vesicular bodies (P), dilated rough endoplasmic reticulum (d), mitochondria (m) and golgi bodies (g).
Figure 4:
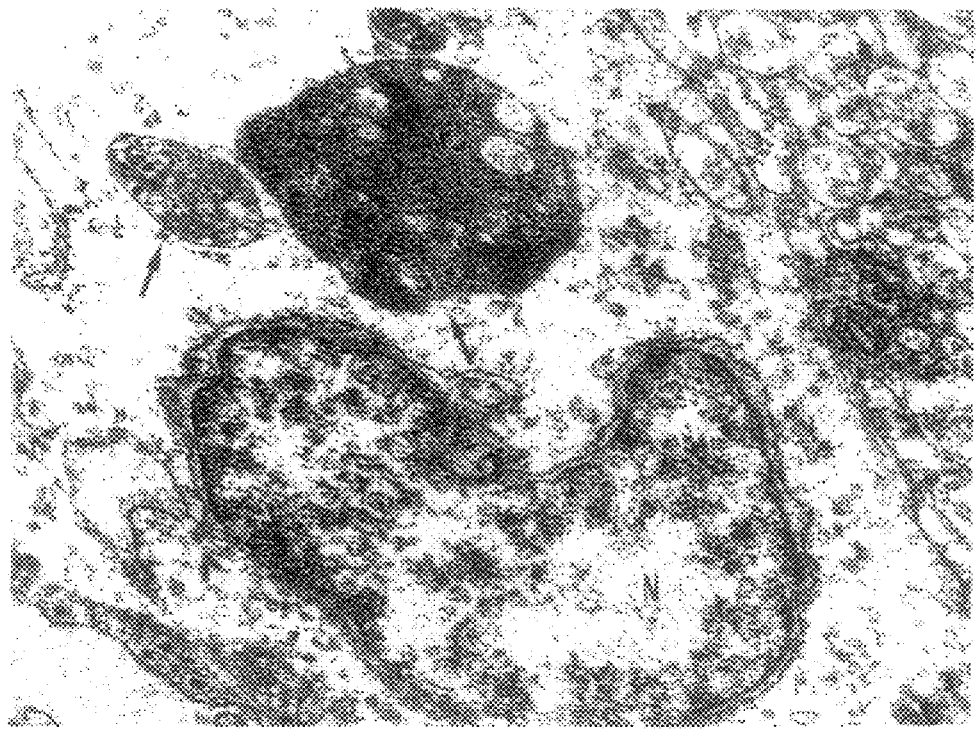
FIG. 4 shows 2 inclusion bodies containing virus-like particles associated with electron dense matrix and membranous vesicles in the cytoplasm of a proventricular cell 4 days post challenge with USDA/STC IBDV+copper sulfate in SPF white leghorn chickens. (N)=Nucleus. Mag. 26,000×.
Figure 5:
FIG. 5 shows a membrane bound inclusion body containing an aggregate of viruslike articles (v), adjacent to the cell nucleus within the submucosa of the proventriculus at 4 days post challenge with USDA/STC IBDV+copper sulfate in SPF white leghorn chickens. Mag. 80,000×. (N)=Nucleus, (d)=dilated rough endoplasmic reticulum, (r)=Ribosome. Compare the size of ribosome to the size of virus-like particles.
Figure 6:
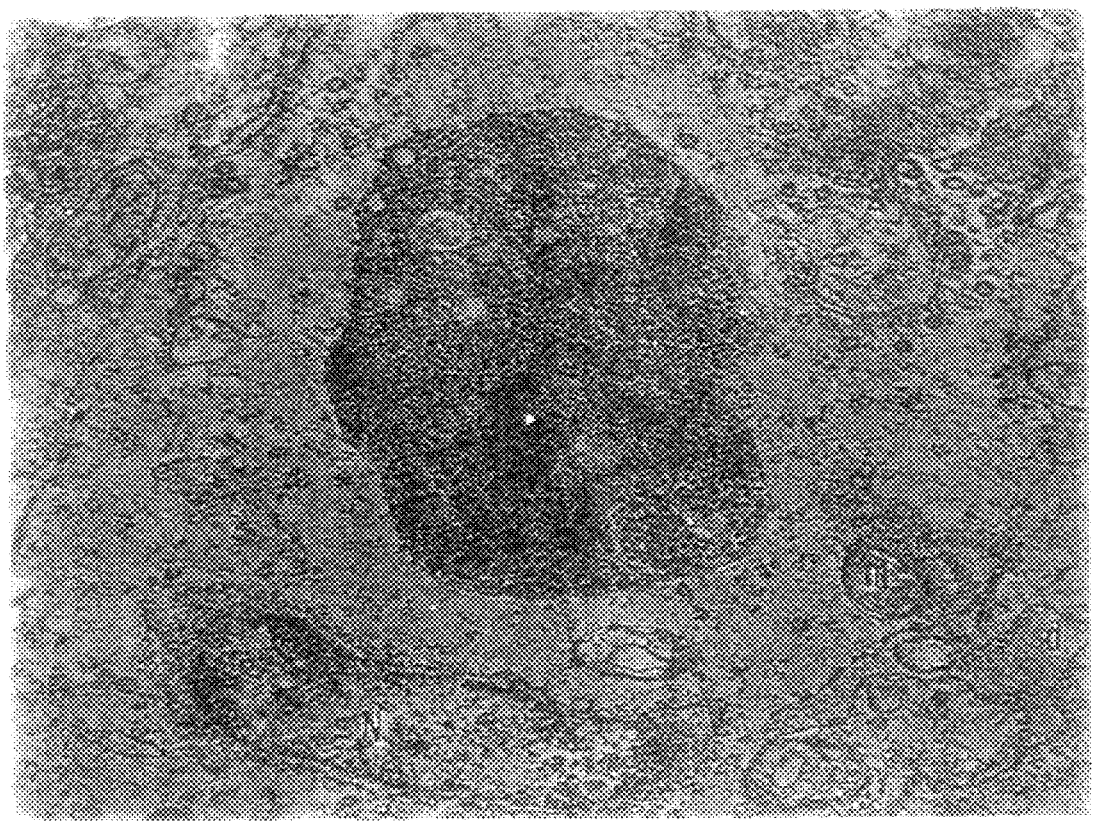
FIG. 6 shows a large membrane bound inclusion body containing densely packed virus-like particles and membranous vesicles adjacent to the nucleus (N) of cell within the submucosa of the proventriculus at 4 days post challenge with USDA/STC IBDV+copper sulfate in SPF white leghorn chickens. Virus-like particles are considerably larger than ribosomal granules. Mitochondria (m), golgi bodies (g) and dilated rough endoplasmic reticulum (d). Mag. 32,000×.
Figure 7:
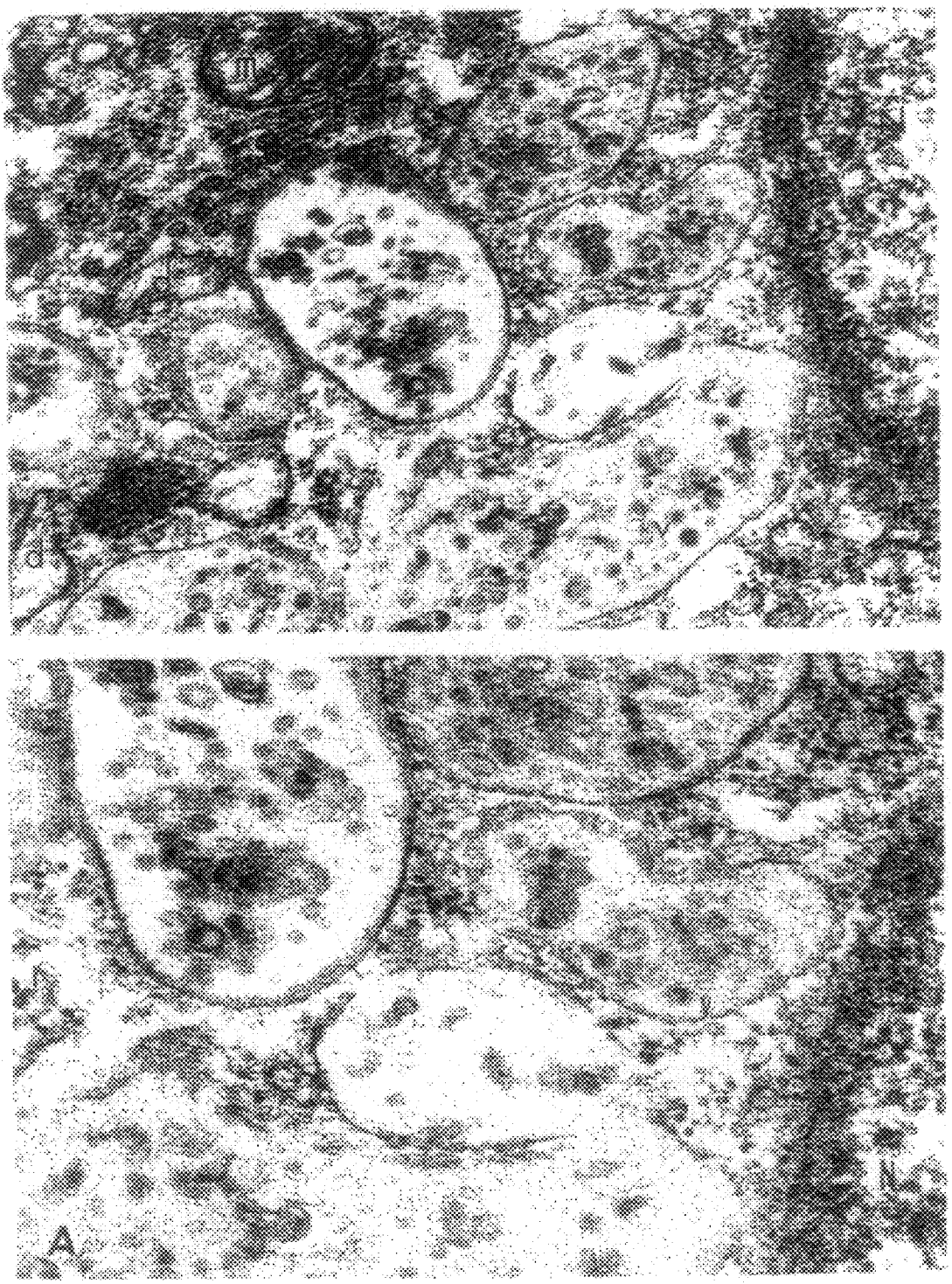
FIG. 7 shows numerous membrane bound inclusion bodies containing virus-like particles (VLP's) and vesicles occurring closely together in the cytoplasm near the nucleus (N) of a cell in the submucosa of the proventriculus at 4 days post challenge with USDA/STC IBDV+copper sulfate in SPF white leghorn chickens. For size comparison see ribosome (r) compare to virus like particles (v).
Figure 8:
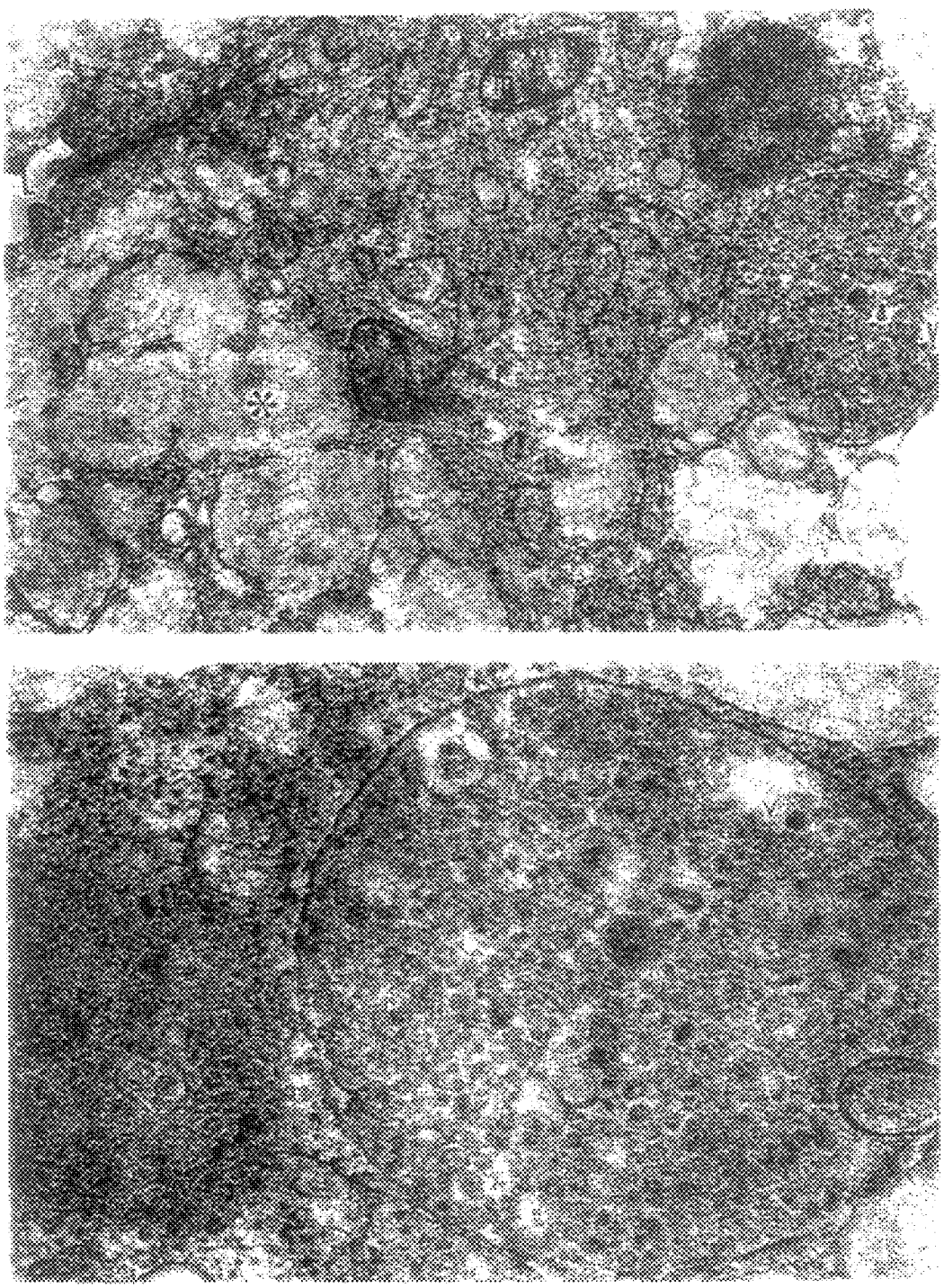
FIG. 8 shows large membrane bound and a non-membrane bound inclusion bodies containing virus-like particles in the cytoplasm of a cell in the submucosa of the proventriculus at 4 days post challenge with USDA/STC IBDV+copper sulfate in SPF white leghorn chickens. Note characteristic mucus containing bodies occurring also in the cytoplasm.

Tissue sections studied with the electron microscope revealed the presence of virus like particles (VLP's), of approximately the same size (60 nm) and shape as described for IBD virus (FIGS. 4–8). These particles were observed in the cytoplasm of the mucosal epithelium surrounding the proventricular papillae. The particles were found individually or in surrounded by a cytoplasmic membrane, appearing as virus containing inclusion bodies. The inclusion bodies also contained fibrillar and electron lucent material, and membranous vesicles of various sizes, which are similar to those interpreted as phagocytic vacuoles or lysosomes. Structure similar to those virus containing inclusion bodies but without the virus like particles were also present in the negative control tissues (FIG. 3). Virus containing inclusion bodies were found predominantly in SPF white leghorn chickens challenged with USDA/STC IBDV+copper sulfate.

AC-ELISA analysis of bursal and proventricular tissue homogenates from SPF white leghorn chickens challenged with Variant E/1084 IBDV tested positive only on day 4 post challenge. The presence of REO virus and/or copper sulfate did not significantly reduce the number of bursal tissues that tested positive. However, the combination of Variant E/1084, REO virus S-1133, and copper sulfate did reduce the number of virus infected proventriculi (Table 18).

AC-ELISA analysis of bursal and proventricular tissue homogenates from SPF white leghorn chickens challenged with USDA/STC IBDV tested positive only on day 4 post challenge (Table 19). Experimental treatments with USDA/STC IBDV+REO virus S-1133 or USDA/STC IBDV+copper sulfate showed a reduction in the number of bursal samples which tested positive. However, the combination of USDA/STC IBDV, REO virus S-1133, and copper sulfate showed no significant reduction in the number of samples which tested positive. The number of positive test samples from the proventriculus in IBDV challenged groups appears to only be adversely affected by the presence of copper sulfate (Table 19).

Figure 9:
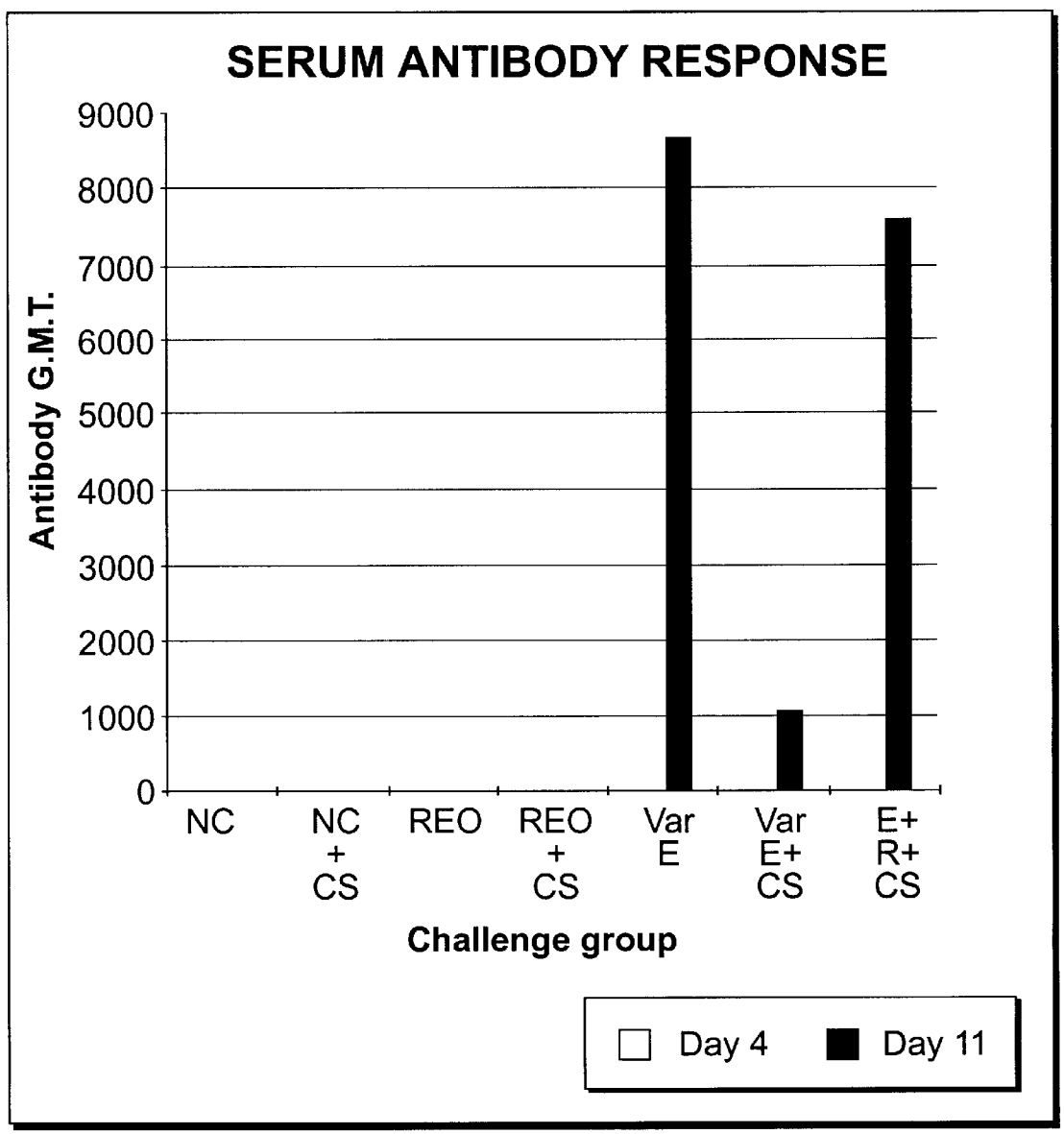
FIG. 9 is a diagram showing serum antibody titers in SPF white leghorn chickens at 4 and 11 days post challenge with Variant E/1084 IBDV in the presence or absence of REO virus and/or copper sulfate.

Serological testing utilizing the KPL infectious bursal disease virus ELISA kit, of serum samples obtained on day 4 post challenge with Variant E/1084 IBDV indicate that all experimental SPF white leghorn chickens had no measurable levels of serum antibody to IBDV (FIG. 9). On day 11 post challenge with Variant E/1084 IBDV the highest antibody response was to the virus alone. Antibody titers to the Variant E/1084+REO+copper sulfate were not significantly different from the virus alone. However, the antibody response to Variant E/1084 IBDV+copper sulfate was significantly suppressed (FIG. 9).

Figure 10:
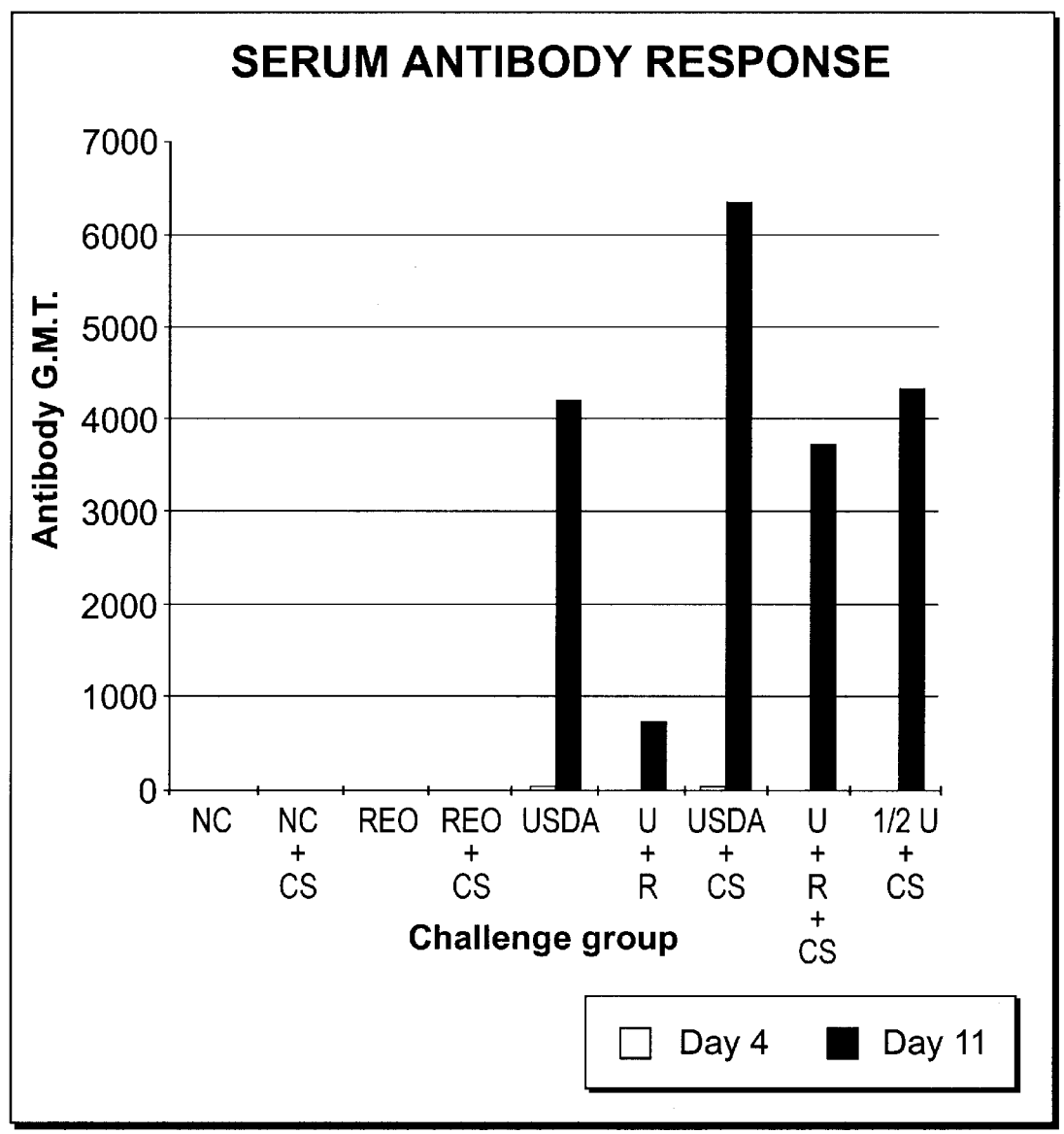
FIG. 10 is a diagram showing serum antibody titers in SPF white leghorn chickens at 4 and 11 days post-challenge with USDA/STC IBDV in the presence or absence of REO virus and/or copper sulfate.

Serological testing of serum samples obtained on day 4 post challenge with USDA/STC IBDV indicates that all experimental SPF white leghorn chickens had no measurable levels of serum antibody to IBDV (FIG. 10). On day 11 post challenge with USDA/STC IBDV, the highest antibody response was USDA/STC IBDV+copper sulfate. The USDA/STC IBDV alone, USDA/STC IBDV+REO+copper sulfate, and the ½× USDA/STC IBDV+copper sulfate had antibody titers that were significantly lower than the USDA/STC IBDV+copper sulfate. The lowest antibody response was with birds that received USDA/STC IBDV+REO (FIG. 10). Gross lesion scores were only significantly different on day 4 post challenge with both strains of IBDV (Table 20). Challenge with Variant E/1084 IBDV resulted in an increase in the gross lesions involving the papillae only and was most pronounced in the challenge group that received Variant E/1084 IBDV+copper sulfate. It should be noted that the addition of REO virus S-1133 in the presence of dietary copper sulfate and Variant E/1084 IBDV resulted in the reduction of the number of lesions present. While the gross lesion incidence in this group was still significantly higher than the negative control, it was approximately 50% less than the value of Variant E/1084 alone and 25% less than value of Variant E/1084 IBDV+copper sulfate (Table 20).

Figure 11:
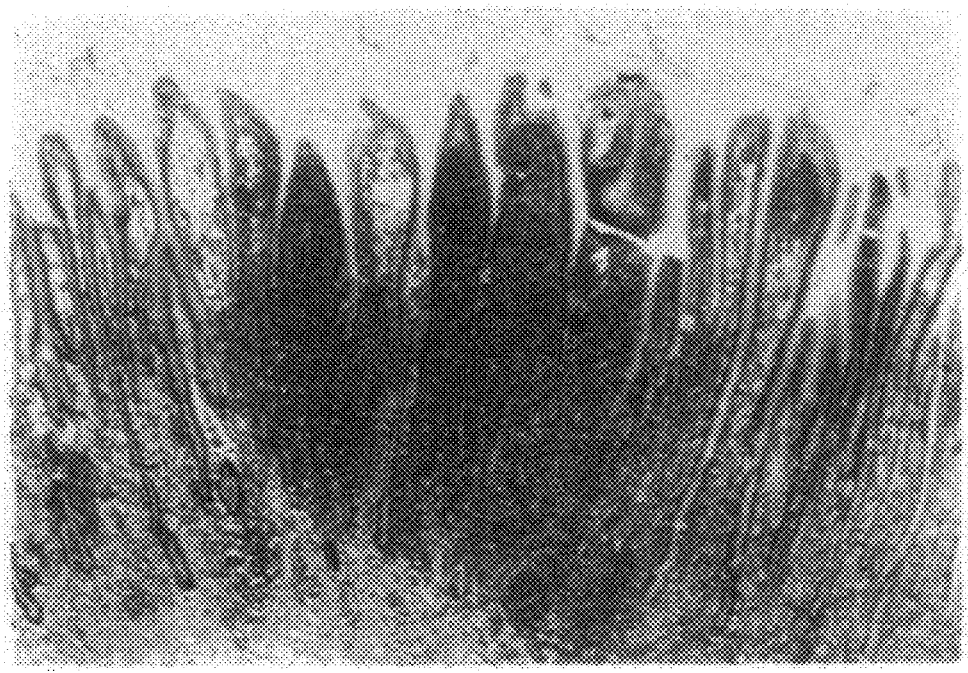
FIG. 11 shows hemorrhage within the mucosa of proventriculus of SPF white leghorn chickens at 28 days post hatch 4 days post challenge with USDA/STC IBDV.

Gross lesions in the proventriculus of SPF white leghorn at 4 days post challenge with USDA/STC IBDV were more extensive than those with Variant E/1084 IBDV (Tables 20 and 21). Hemorrhage values are significantly increased in the presence of USDA/STC IBDV+copper sulfate, and with USDA/STC IBDV+REO. However, the combination of USDA/STC IBDV+REO+copper sulfate is not significantly different from the negative control values (Table 21). Hemorrhage associated with IBDV infection was contained within the mucosa of the proventriculus and were visible grossly as well (FIG. 11).

Papillae gross scores for birds challenged with Variant E/1084 in the presence or absence of copper sulfate and REO virus were significantly different from the negative control (Table 20). Papillae gross scores were significantly different from the negative control in all USDA/STC IBDV challenge groups with the exception of the USDA/STC IBDV+copper sulfate. Papillae scores were highest for the challenge group which received USDA/STC IBDV+REO, similar for the challenge groups that received the USDA/STC IBDV only and the USDA/STC IBDV+REO+copper sulfate and lower in the ½× USDA/STC IBDV+copper sulfate (Table 21).

Gross lesions in the gizzard were assessed as to the degree of organ rigidity at necropsy. Numerical value assignments were assessed according to the softness of the tissue, and a higher score value reflects a tissue that is soft and pliable. Lower value scores reflect a tissue that is extremely rigid. Gizzard rigidity in birds challenged with Variant E/1084 in the presence or absence of copper sulfate and/or REO virus was not significantly different from the negative control values at 4 days post challenge (Table 20). Gizzard rigidity was highest in the USDA/STC IBDV challenge group. Gizzards from the groups which received USDA/STC IBDV+copper sulfate and USDA/STC IBDV+REO S-1133 were also significantly harder than the negative control values (Table 21).

Figure 12:
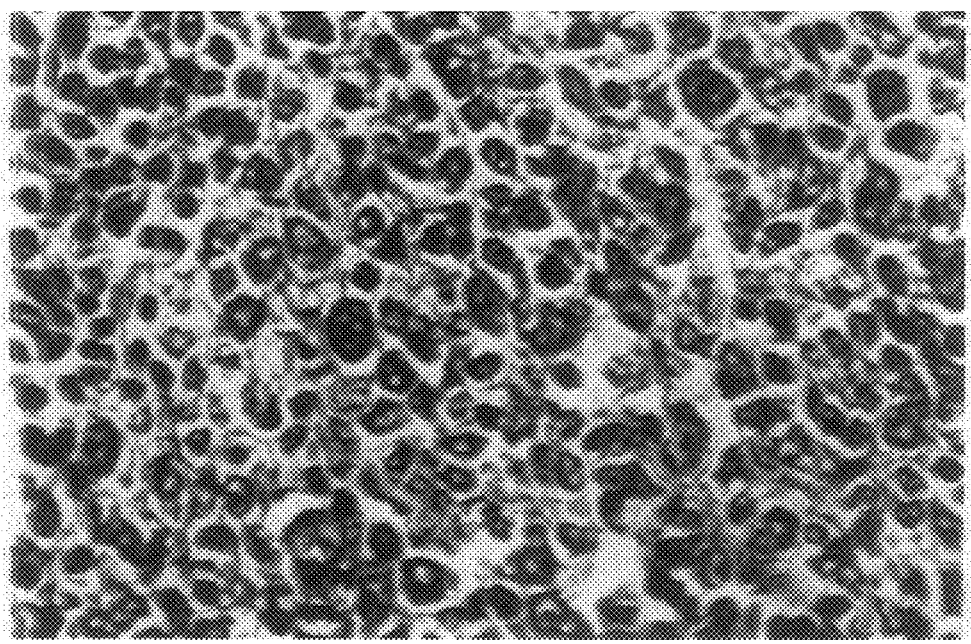
FIG. 12 shows pleomorphic cells within the proventriculus of SPF white leghorn chickens challenged at 28 days post hatch with USDA/STC IBDV only.
Figure 13:
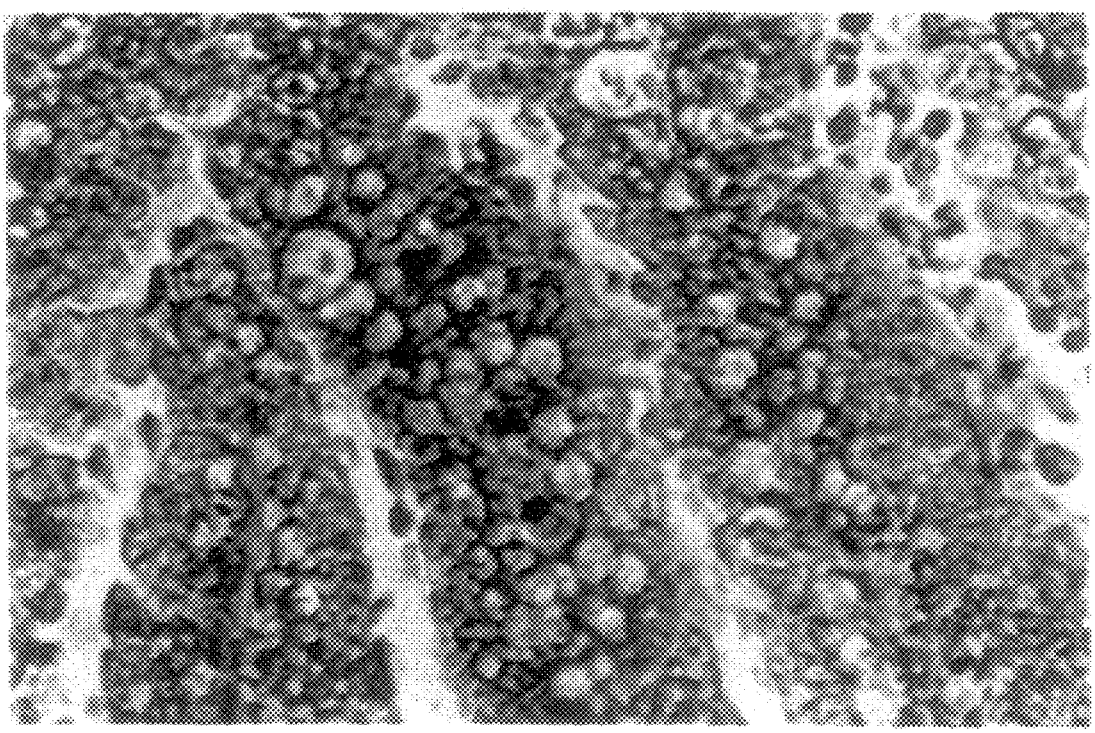
FIG. 13 shows vacuolated cells within the glands of the proventriculus of SPF white leghorn chickens challenged at 28 days post hatch with USDA/STC IBDV+Copper Sulfate at 4 days post challenge (40×).

Microscopic tissue lesions in the proventriculus following IBDV challenge were found predominantly in the lamina propria of the mucosa and were characterized by pleomorphism of the lymphoid cells in the mucosa (FIG. 12). This cellular pleomorphism was sometimes accompanied by lymphocyte depletion, similar to what is described in the bursa following IBDV challenge. The addition of copper sulfate in the infection scheme introduced a new type of lesion within the secretory glands of the proventriculus. The cells which line the glandular ducts appeared to be swollen and contain large vacuoles (FIG. 13). Lesions in the bursae were predominantly lymphoid depletion with an accompanied follicle degeneration.

Microscopic tissue lesions in the bursa following challenge with Variant E/1084 IBDV were present in all the SPF white leghorn chickens sampled on day 4 and day 11. Microscopic tissue lesions in the proventriculus following challenge with Variant E/1084 IBDV were present only on day 4 post challenge. There was a reduction in the number of SPF white leghorn chickens exhibiting lesions in the Variant E/1084+copper sulfate treatment (Table 22).

Microscopic tissue lesions in the bursa following challenge with USDA/STC IBDV were present in all the SPF white leghorn chickens sampled on day 4 and day 11 (Table 23). Microscopic tissue lesions in the proventriculus following challenge with USDA/STC IBDV were present only on day 4 post challenge. There was no significant reduction in the presence of lesions by any of the treatments (Table 23).

Bursa to body weight and spleen to body weight ratios of SPF white leghorn chickens at 4 days post challenge with Variant E/1084 IBDV were significantly different in all IBDV challenged groups (Table 24). There were no significant differences in the proventriculus to body weight ratios in any of the experimental groups at day 4 post challenge. At day 11 post challenge all IBDV challenged groups had significantly lower bursa to body weight ratios. The experimental group that received Variant E/1084 IBDV only was significantly different for the spleen to body weight ratios. The proventriculus to body weight ratios at day 11 post challenge were significantly different only for the experimental group that received Variant E/1084 IBDV+REO+copper sulfate (Table 24).

Bursa to body weight ratios of SPF white leghorn chickens at 4 days post challenge with USDA/STC IBDV were significantly different for groups that received USDA/STC IBDV+REO+copper sulfate, and USDA,/STC IBDV+REO (Table 25). At 4 days post challenge all USDA/STC IBDV challenged groups had significantly different spleen to body weight ratios. At 4 days post challenge the proventriculus to body weight ratios were significantly different only in the group that received USDA/STC IBDV only. On day 11 post challenge all experimental groups that received USDA/STC IBDV were significantly atrophied. On day 11 post challenge only the USDA/STC IBDV+copper sulfate group was significantly different from the negative control. On day 11 post challenge USDA/STC IBDV only, USDA/STC IBDV+copper sulfate, and USDA/STC IBDV+REO+copper sulfate were significantly different from the negative control (Table 25).

Figure 14:
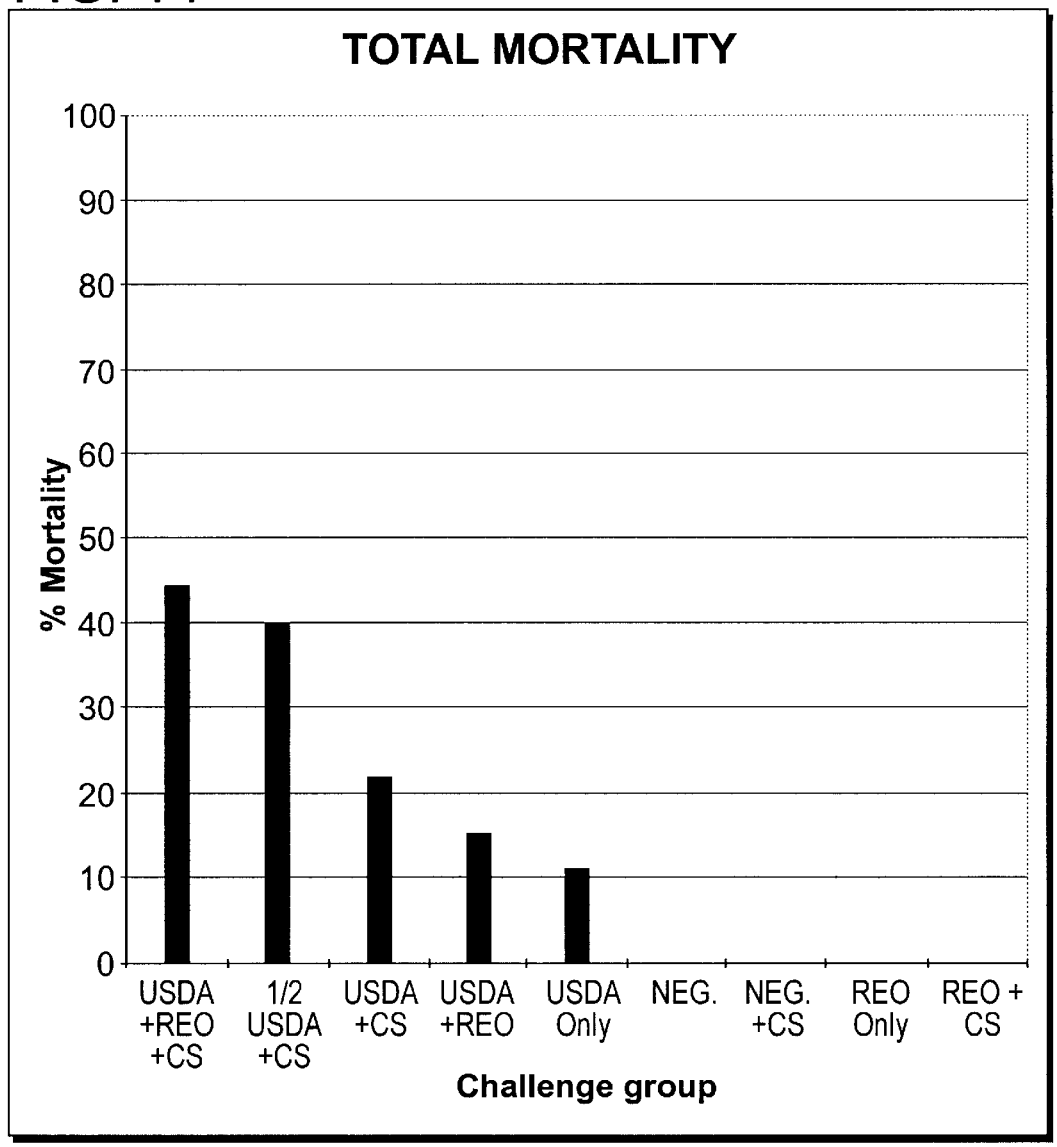
FIG. 14 is a diagram showing total mortality in SPF white leghorn chickens following challenge with Variant E/1084 IBDV and USDA/STC IBDV in the presence or absence of REO virus and/or copper sulfate.

Mortality for the study was 44% for SPF white leghorn chickens challenged with USDA/STC IBDV+REO+copper sulfate, 40% for ½× USDA/STC IBDV+copper sulfate, 21% for USDA/STC+copper sulfate, 15% for USDA/STC IBDV+REO, and 11% for USDA/STC IBDV only (FIG. 14). Mortality began at approximately 3 days post challenge, peaked at 4 days post challenge, and continued until 5 days post challenge. Variant E/1084 did not produce any mortality throughout the entire study (data not shown).

Figure 15:
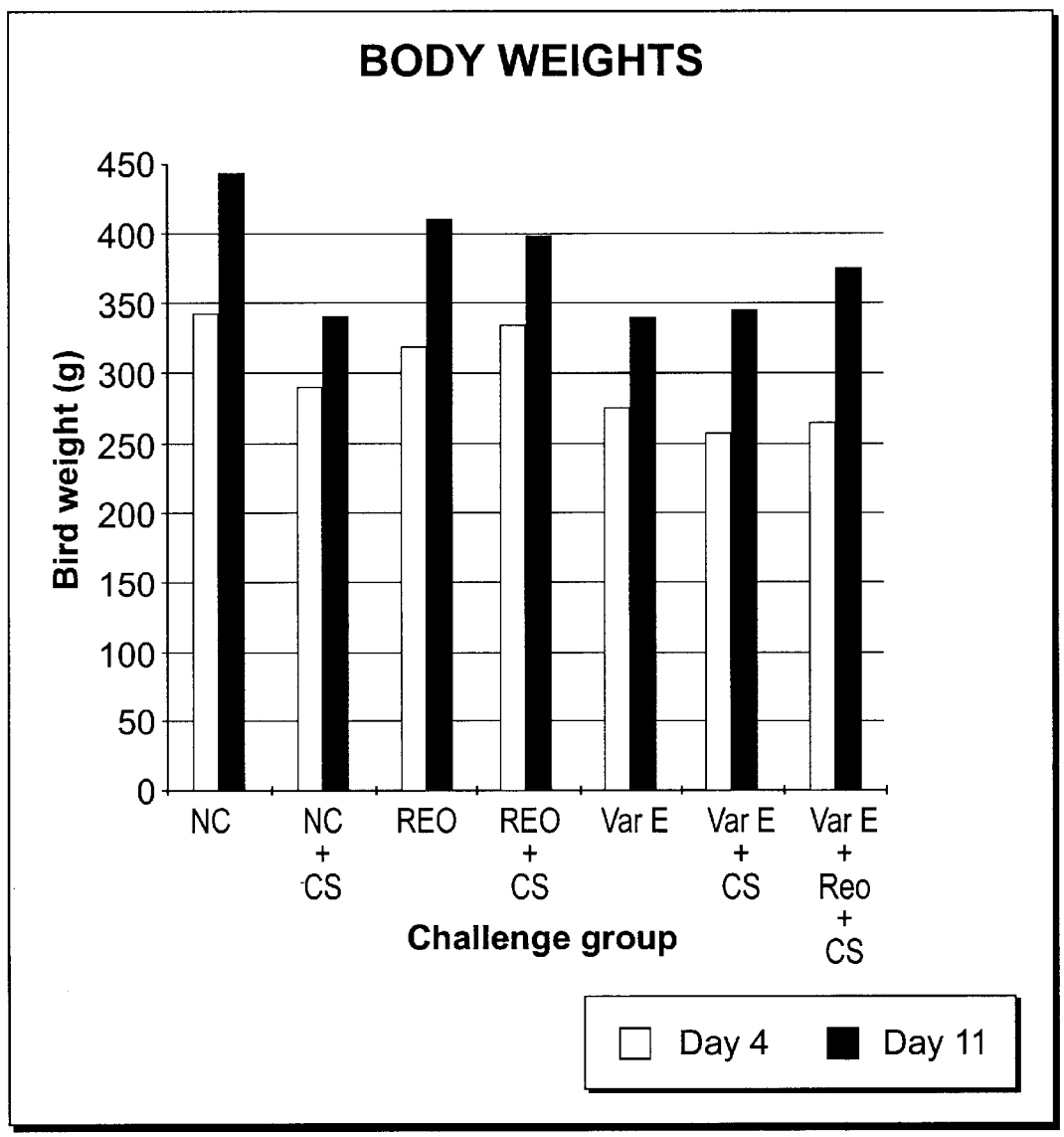
FIG. 15 is a diagram showing body weight means for SPF white leghorn chickens at 4 and 11 days post challenge with Variant E/1084 IBDV in the presence or absence of REO virus and/or copper sulfate.

Mean body weight differences were compared for 4 and 11 days post challenge with Variant E/1084 IBDV (FIG. 15). All SPF white leghorn chickens gained weight between day 4 and day 11 post challenge, however, all experimental groups had lower weight gains than the negative control group. REO virus infection in the presence and absence of copper sulfate, and Variant E/1084 did not significantly decrease weight gain. However, copper sulfate only, Variant E/1084 IBDV only, and Variant E/1084 IBDV+copper sulfate body weight gain was significantly lower than the negative control (FIG. 15).

Figure 16:
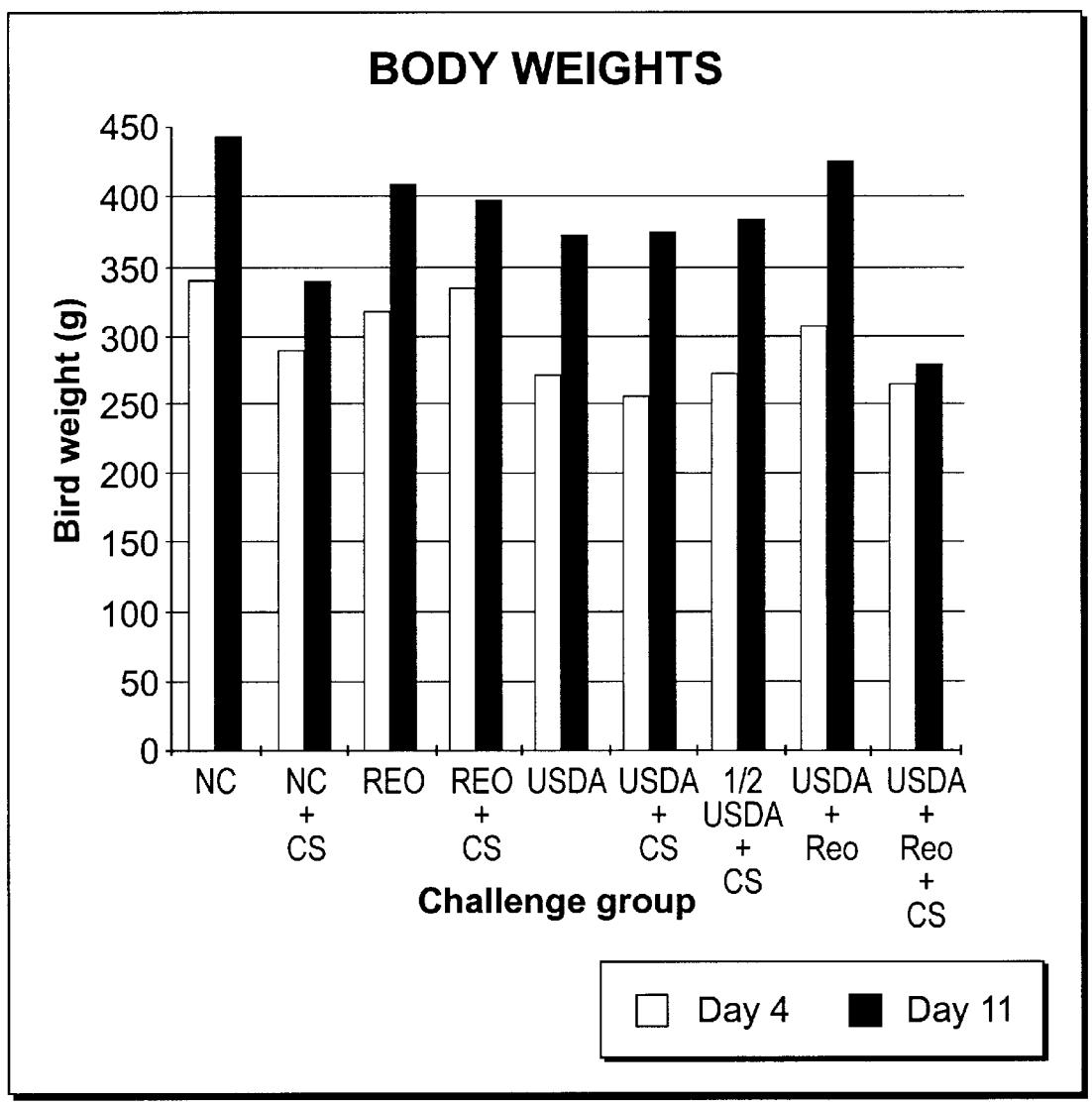
FIG. 16 is a diagram showing body weight means for SPF white leghorn chickens at 4 and 11 days post challenge with USDA/STC IBDV in the presence or absence of REO virus and/or copper sulfate.

Mean body weight differences were compared for 4 and 11 days post challenge with USDA/STC IBDV (FIG. 16). All SPF white leghorn chickens challenged with USDA/STC IBDV gained weight between day 4 and day 11 post challenge, however, all experimental groups had lower weight gains than the negative control group. Day 11 body weight means were only significantly different in the USDA/STC IBDV+REO+copper sulfate, and the copper sulfate only groups.

DISCUSSION

Electron micrographs reveal the presence of viral inclusion bodies at 4 days post challenge. These inclusions are similar in size and structural characteristics to those described by a number of other authors for bursal tissues infected with IBDV (17, 40, 52, 73, 86). While micrographs presented are from only one experimental group, USDA/STC IBDV+copper sulfate, they in no way indicate that other experimental IBDV groups were lacking in viral inclusions. Rather that pictures were selected based on the quality of the sections cut and the reproducibility of the photos.

AC-ELISA indicated the presence of USDA/STC and Variant E/1084 IBDV in the bursa and proventriculus at 4 days post challenge. The presence of REO virus S-1133 and copper sulfate did not interfere with the number of bursal tissues that tested positive by AC-ELISA. However, in IBDV challenged groups in the presence of REO S-1133 virus or copper sulfate there was a reduction in the number of tissues that tested positive by AC-ELISA. Both, the copper sulfate and REO virus S-1133 exert their effects on the chicken primarily in the proventriculus and the possibility exists that there is competition for limited substrate in the proventriculus and that the presence of both mediates the reaction. In on contrast, the combination of IBDV+REO+copper sulfate reduced the number of samples that tested positive in the bursa but not in the proventriculus indicating the possibility of other influencing factors.

Serological evidence showed a reduced response in the presence of copper sulfate for Variant E/1084 and an increased response to USDA/STC IBDV. USDA/STC IBDV antibody response was significantly reduced in the presence of REO S-1133 virus. Antibody response to USDA/STC IBDV has consistently been lower than antibody response to Variant E/1084 IBDV. This has been generally attributed to the higher degree of damage induced by USDA/STC IBDV and a lack of cells capable of producing antibodies. It would appear that the addition of REO S-1133 virus further reduces the production of antibodies against USDA/STC IBDV, possibly as it exerts its own immunosuppressive mechanisms or through interference.

Gross lesions in the proventriculus involving the papillae were noticeably increased in the presence of copper sulfate+ Variant E/1084. However, papillar lesions were reduced in the presence of REO S-1133. Gross lesions associated with USDA/STC IBDV included hemorrhage, and involvement of papillae in all but the USDA/STC IBDV+copper sulfate challenge group. Papillar lesions were of highest incidence in the presence of USDA/STC IBDV+REO S-1133 and with the addition of copper sulfate there appears to be a mediation of the reaction. Gizzard rigidity was also noticeably higher in SPF white leghorn chickens which received USDA/STC IBDV alone, or +copper sulfate, or +REO S-1133. The combination of all three did not appear to exert any effect.

Microscopic lesions are present in the bursa at day 4 and 11 post challenge with both IBDV strains as expected. Microscopic lesions in the proventriculus were however, only present on day 4 post challenge. There appears to be no treatment influence with USDA/STC IBDV, but the presence of copper sulfate reduced the number of birds showing lesions with Variant E/1084 IBDV.

Organ to body weight ratios were significantly different in the bursa and spleen on day 4 post challenge, but effects were seen in the proventriculus only on day 11 post challenge. The proventriculus was most affected by the combination of Variant E/1084+REO+copper sulfate and copper sulfate+REO challenge groups. Reduced overall body weights were noticed for all IBDV challenged groups as well as those receiving copper sulfate with no virus. Bayyari et al (5) described similar effects in broiler chickens given dietary copper sulfate in the presence of an undefined pathogen and Wideman et al (152) demonstrated similar findings with diets containing excessive levels of copper sulfate.

Mortality was significantly increased in the USDA/STC IBDV in the presence of REO S-1133 and copper sulfate, however, there was no increase in mortality with Variant E/1084. All mortality occurred prior to necropsy in the USDA/STC IBDV groups. SPF white leghorn chickens that died prior to necropsy were not tested for virus in the bursa and proventriculus and represent potential positive samples had they been tested.

SECTION 4

INFECTIOUS BURSAL DISEASE VIRUS INDUCED APOPTOSIS ASSOCIATED WITH PRODUCTION OF LESIONS IN THE PROVENTRICULUS AND BURSA

SUMMARY

The presence of apoptotic cells in the proventriculus and bursa at 4 days post challenge with USDA/STC IBDV and Variant E/1084 IBDV was determined using a modified TUNEL fluorescent staining procedure. Specific green fluorescence was found in highest quantity in the bursa, no differences in the intensity of staining could be determined for each IBDV strain. Fluorescence was focused predominantly in the medulla and cortex of infected bursae. Proventricular fluorescent staining was found predominantly in the villi and submucosa. Fluorescent intensity of proventricular sections appeared highest in tissue sections from SPF leghorn chickens challenged with USDA/STC IBDV.

INTRODUCTION

Apoptosis has been proposed as one of the mechanisms by which a number of viruses induce pathology (49, 70), recent studies have indicated that IBDV also utilizes this mechanism (6, 13, 145, 148, 149). Apoptosis is a genetically ordered sequence of events following a very specific cellular signaling stimulus in which irreparably damaged cells are disposed of with minimal damage to surrounding cells or tissue.

Apoptosis should not be confused with necrosis, as each represents a totally different set of events albeit with some overlap. Cellular necrosis results from physical injury and is not in any way genetically controlled, whereas apoptosis is a genetically predetermined deliberate cellular response to specific developmental and environmental stimuli. Injury events that produce necrosis can trigger apoptosis in response to the presence of cellular debris and inflammation. Likewise, it may be possible that induction of apoptosis could indirectly produce necrosis in some instances where cellular degeneration results from a disease process. Necrosis is typified by the destruction of cytoplasmic organelles and loss of the integrity of the plasma membrane (12, 92, 151). Apoptosis is associated with the boiling of the cytoplasm, chromatin condensation (12, 49, 70, 92, 151), fractured nuclear DNA, and can be distinguished from necrosis by lack of an inflammatory response (12, 92, 151).

Where viruses are concerned, the inhibition of apoptosis has resulted in persistent infections, latency, or enhanced virus production (49, 70, 145, 148, 149). On the other hand, promotion of apoptosis has been demonstrated to facilitate virus spread and release (12, 92, 151).

Infectious bursal disease virus infection occurs sometimes without overt clinical disease symptoms. Previous experiments utilizing IBDV challenge in SPF white leghorn chickens presented a number of tissues in which the cellular damage present could not be directly linked to necrosis following a viral inflammatory response. Experimental data also indicated that virus persistence in tissues (AC-ELISA) could be associated with more severe pathology during the acute stage of the infection. The purpose of this study was to determine the presence of apoptotic cells in the bursa and proventriculus following challenge with USDA/STC IBDV and Variant E/1084 IBDV.

MATERIALS AND METHODS

Formalin fixed tissues from experiments described in Section 3 were utilized in this staining procedure. All tissues utilized were harvested at 4 days post challenge with a 1× concentration of USDA/STC IBDV or Variant E/11084 IBDV. Tissues from specific birds were selected following an initial screening with hematoxylin and eosin stained sections. Tissue preparation and sectioning were as follows. Tissues were placed in 10% buffered formalin at necropsy. Twenty-four hours later tissues were removed, manually trimmed to a thickness of ⅛ inch and placed in tissue cassettes. Tissues were dehydrated through graded alcohols and cleared in two changes of toluene. Tissues were then infiltrated with paraffin over a 16 hour period using an autoprocessor. Following paraffin infiltration, tissues were positioned in paraffin blocks and trimmed to expose a uniform tissue face. Prepared tissue blocks were stored at −20° C. until ready to be sectioned. Sections were cut at a thickness of 5 µm and floated on a water bath containing 5% gelatin to facilitate attachment (55). Sections were captured onto standard 1×3 inch glass microscope slides that had been coated with poly L-lysine solution (Appendix) (Sigma, Inc., St. Louis, Mo.). Tissue blocks were sectioned and multiple slides were prepared for each specimen. Slides with tissue sections were stored at 4° C. until they were deparaffinized for staining.

TUNEL TISSUE STAINING PROCEDURE

The TUNEL procedure detects the presence of apoptotic cells by the in situ labeling of breaks in the nuclear DNA within individual cells. TUNEL stands for TdT-mediated dUTP-biotin nick end labeling and is based on the specific binding of terminal deoxynucleotidyl transferase(TdT) to exposed 3'-OH ends of DNA fragments generated through apoptotic mechanisms (12). The following procedure outlines a modified TUNEL procedure utilized for apoptotic assessment of bursal and proventricular tissues following challenge with IBDV.

Tissue sections were prepared as described earlier and removed from storage at 4° C. Tissue sections had been previously assigned numbers so that the individual screening of them would be blinded to the treatments. Each experimental group was represented by tissues from 3 SPF white leghorn chickens, and all sections were cut and stained in triplicate. Prepared slides with suspect tissue sections were deparaffinized and hydrated through the following solutions: twice in 100% Xylene for 5 minutes each, twice in 96% ethanol for 3 minutes each, 90% ethanol for 3 minutes, 80% ethanol for 3 minutes, and double distilled water (dd$H_2O$) for 10–20 minutes. Tissue sections were then treated with a proteinase K (Sigma, Inc., St. Louis, Mo.) solution (5 ug/ml with 0.5% Triton X-100) in Dulbecco's phosphate buffered saline (D-PBS) (Appendix) for 5–6 minutes. Slides were then washed 2 times with D-PBS for 5 minutes each. The slides were then placed on a flat slide tray and tissue sections were covered with equilibration buffer (Appendix) and incubated at room temperature for 10 minutes. Equilibration buffer was removed by wicking onto a Kimwipe™ (Kimberly Clark Corp., Roswell, Ga.). Tissue sections were then covered with TdT 12-dUTP reaction mixture (Appendix). Sections were incubated at 37° C. with high humidity for 1 hour. Reaction buffer was removed and slides were placed in stop buffer (330 mM NaCl, 3 mM NaCitrate, pH 8.0) at room temperature for 15 minutes. Slides were then counter stained using 0.1 ug/ml DAPI (4',6-Diamidine-2'-phenylindole dihydrochloride) (Boehringer Mannheim Biochemica, Indianapolis, Ind.) in D-PBS for 15 minutes. Slides were washed 3 times with D-PBS, coverslips were mounted and sealed with nail polish. Slides were stored at 4° C. overnight before viewing for the presence of fluorescence. Slides were viewed using an Olympus BX50 microscope equipped with a Olympus PM-C35X camera and Omega dye specific fluorescence filters (DAPI 385–395) (FITC 475–497). An Image Pro computer analysis system equipped with an Optronic cd video camera under the control of Image Pro Plus software (Media Cybernetics, Silver Spring, Md.) was utilized to capture images from stained slides at the same time.

RESULTS

Figure 17:
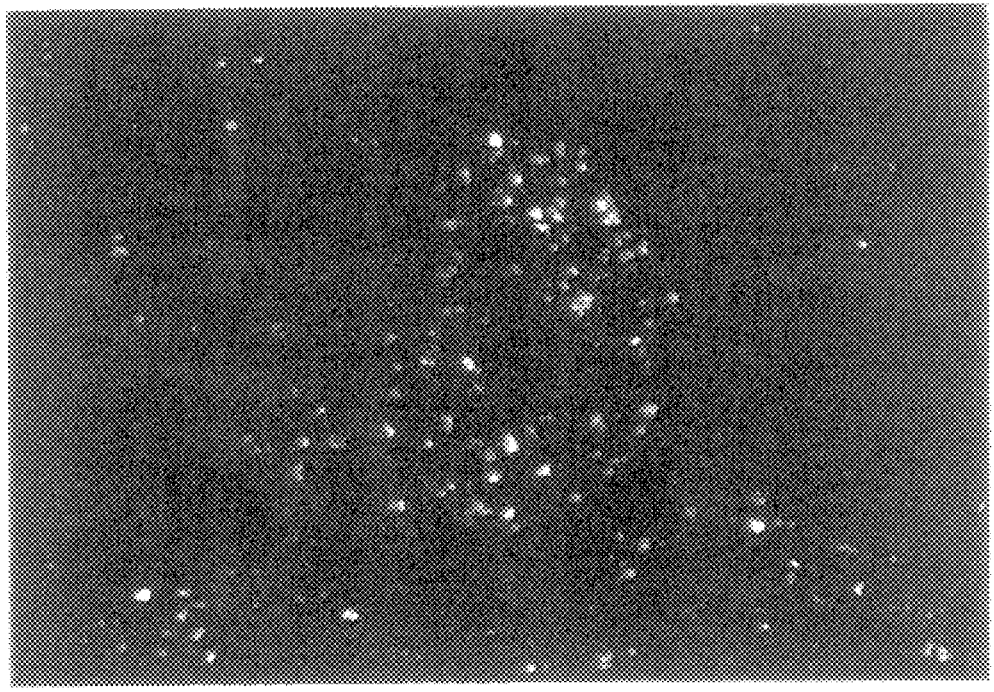
FIG. 17 shows a TUNEL staining for the presence of apoptosis. Bursa section from 32 day post hatch SPF white leghorn chickens at 4 days post challenge with Variant E/1084 IBDV. Positive fluorescence in the medulla and cortex of the bursal follicle (20×).
Figure 18:
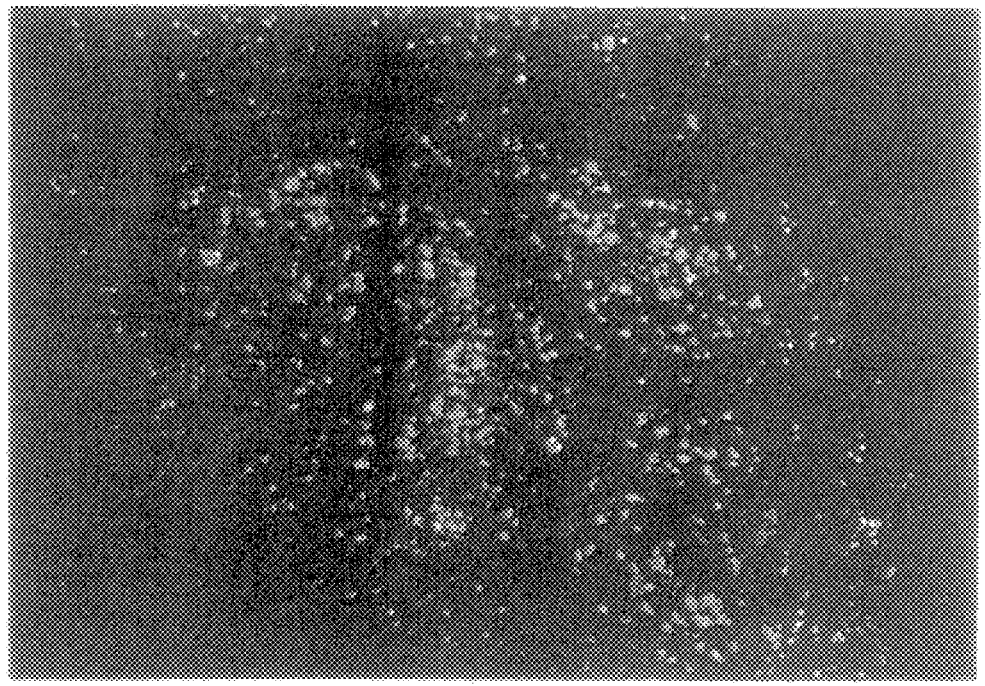
FIG. 18 shows a TUNEL staining for the presence of apoptosis. Bursa section from 32 day post hatch SPF white leghorn chickens at 4 days post challenge with USDA/STC IBDV. Positive fluorescence in the medulla and cortex of the bursal follicle (20×).
Figure 19:
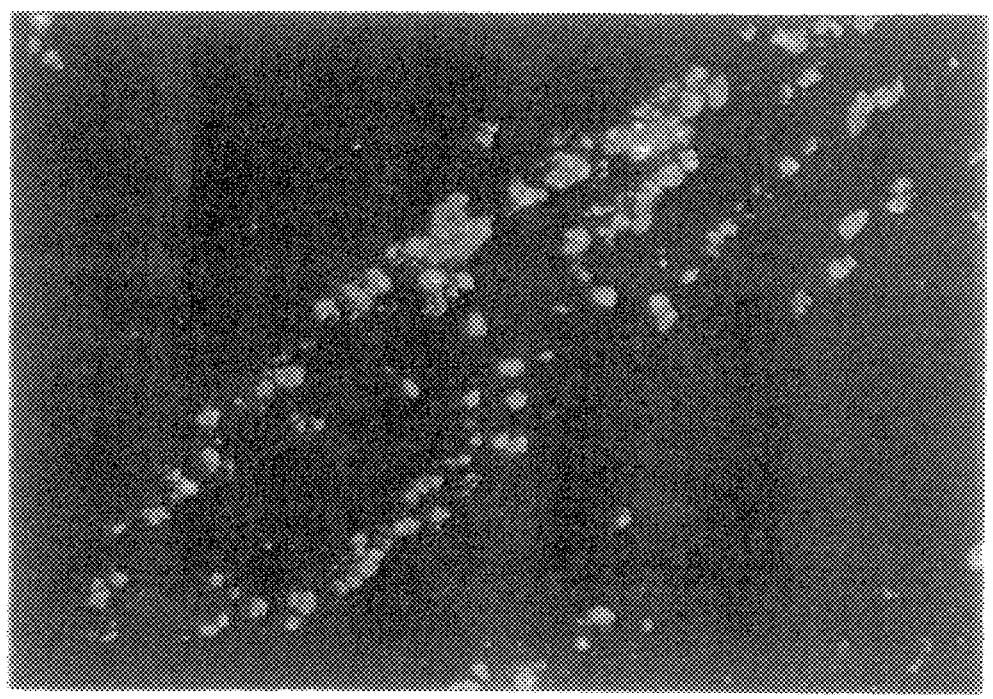
FIG. 19 shows a TUNEL staining for the presence of apoptotic cells. Proventriculus section from 32 day post hatch SPF white leghorn chickens at 4 days post challenge with USDA/STC IBDV. Positive fluorescence within the cells of the proventricular villus (40×).
Figure 20:
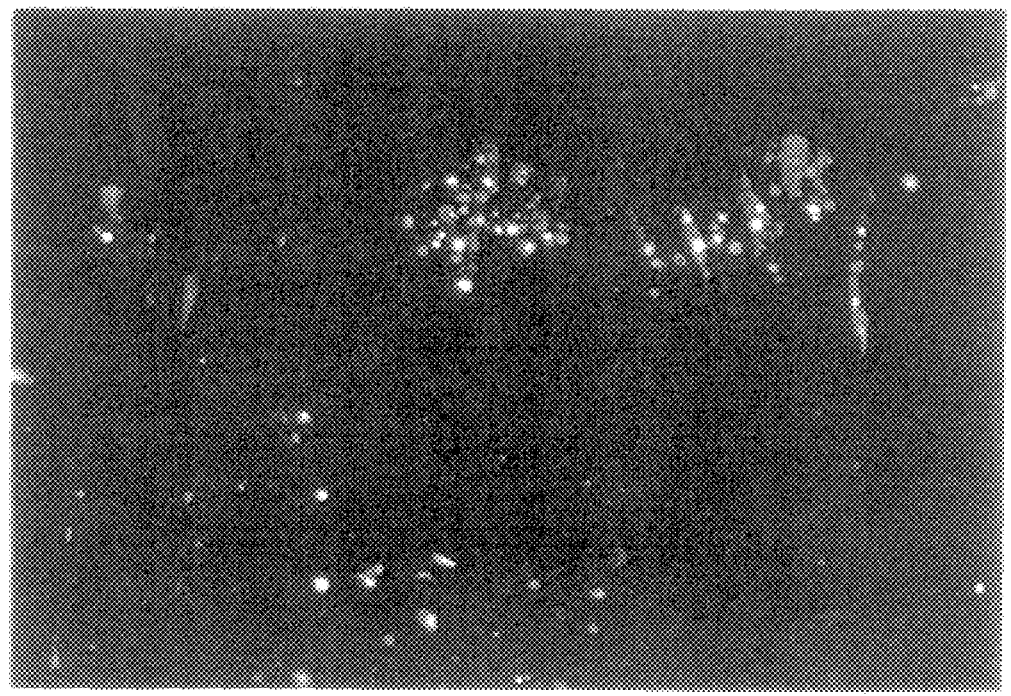
FIG. 20 shows a TUNEL staining for the presence of apoptotic cells. Proventriculus section from 32 day post hatch SPF white leghorn chickens at 4 days post challenge with Variant E/1084 IBDV. Positive fluorescence within the cells in the tips of the proventricular villi (40×).
Figure 21:
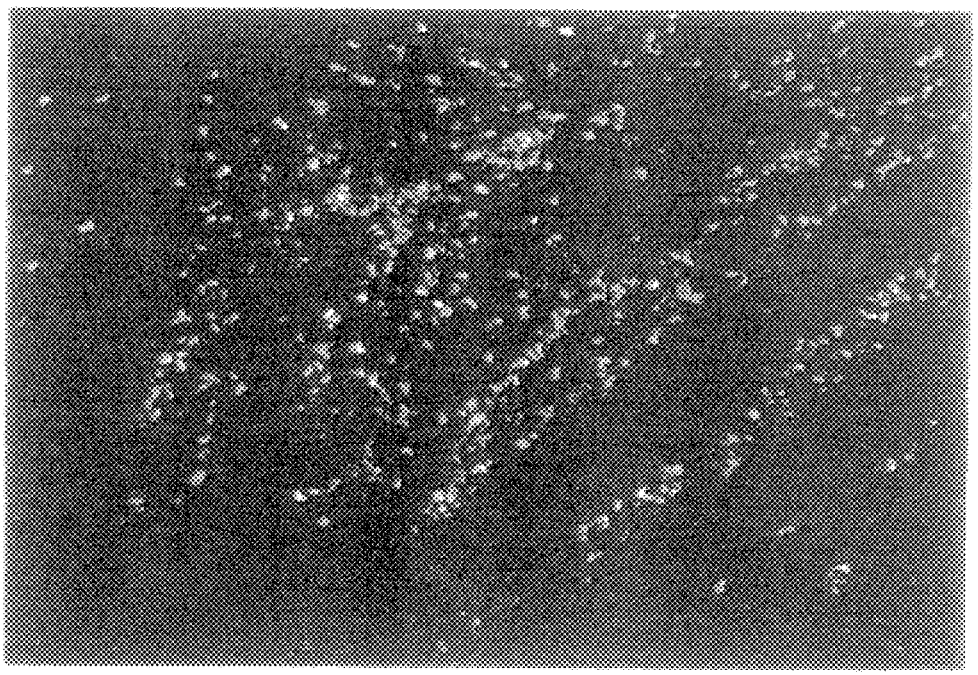
FIG. 21 shows a TUNEL staining for the presence of apoptotic cells. Proventriculus section from 32 day post hatch SPF white leghorn chickens at 4 days post challenge with Variant E/1084 IBDV. Positive fluorescence within the cells of the proventricular glands and surrounding connective tissue (20×).
Figure 22:
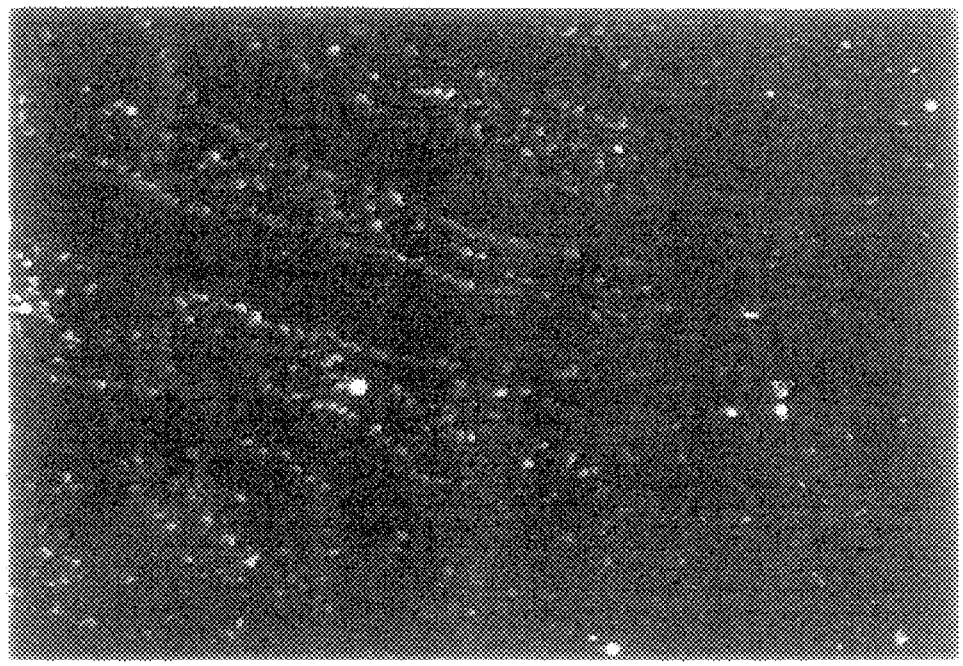
FIG. 22 shows a TUNEL staining for the presence of apoptotic cells. Proventriculus section from 32 day post hatch SPF white leghorn chickens negative control. Negative for green fluorescence, DAPI staining indication of normal DNA structure (20×).

Tissue sections were viewed for the presence of specific green fluorescence in the cellular nuclei and scored as positive when present and negative when absent (Table 26). No quantitation of the amount of fluorescence present was attempted, but visual differences were noticeable as to intensity of the fluorescence and the localization of the fluorescence within tissue sections. The degree of staining intensity as a reflection of the total involvement of the tissue section is reflected in the + or − score in Table 25. Fluorescence was present in all bursal and proventricular tissues from SPF white leghorn chickens that were challenged with USDA/STC IBDV or Variant E/1084 IBDV 4 days prior to sample collection. Staining intensity of the bursal sections was higher within the medulla and cortex of the bursal follicles (FIG. 17), with low levels of fluorescence in the connective tissue surrounding the follicles (FIG. 18). Staining of the proventricular tissues was found predominantly within the villi (FIGS. 19 and 20) with occasional staining in the glands (FIG. 21). The specific green fluorescence was noticeably absent from negative control SPF white leghorn chickens (FIG. 22). Tissues which demonstrated more severe lesions with H and E staining also reflected the presence of apoptotic cells deeper in the area of the glands (FIG. 21).

DISCUSSION

Formalin fixed paraffin embedded proventricular tissues harvested from SPF white leghorn chickens at 4 days post challenge with USDA/STC IBDV and Variant E/1084 IBDV demonstrated evidence of the presence of apoptotic cells. Although the intensity and the incidence of this particular type of staining were not quantitated, visual observations were that higher levels of apoptotic cells were present in the proventriculus of birds challenged with USDA/STC IBDV. This is not to say that apoptotic cells were totally absent from proventriculi that were exposed to Variant E/1084 but just that there number appears to be less. This may in fact be a reflection of where the section of tissue is actually cut, and not a reflection of viral pathogenicity. Also, please note that these sections were taken at only one time point following IBDV challenge, in SPF white leghorn chickens that were given what is considered a standard challenge of each IBDV strain. Based on the known infectivity titers of these two virus preparations, the USDA/STC IBDV had an advantage over Variant E/1084 IBDV. Previous studies have indicated that lesions are more severe in the proventriculus of SPF white leghorn chickens following challenge with the USDA/STC IBDV.

Bursal tissues also demonstrated the presence of apoptotic cells following challenge with both the USDA/STC IBDV and Variant E/1084 IBDV. No visual differences could be determined for fluorescent intensity and quantity of stained bursal cells between the two challenge strains of IBDV. This is more or less a reflection of the large number of cells that fluoresce in infected bursae following staining.

SECTION 5

MEASUREMENT OF HEMOLYTIC COMPLEMENT LEVELS AND VIRUS NEUTRALIZING ANTIBODY TITERS IN SPF WHITE LEGHORN CHICKENS 4, 6, 8 AND 11 DAYS POST CHALLENGE WITH INFECTIOUS BURSAL DISEASE VIRUS STRAINS USDA/STC, VARIANT E/DEL, and Variant E/1084

SUMMARY

Hemolytic complement levels were decreased at 4 days post challenge in all IBDV challenge groups. Highest level of depletion was in the SPF white leghorn chickens challenged with USDA/STC IBDV. Complement levels were recovered by 6 days post challenge which corresponded with measurable levels of neutralizing antibodies against USDA/STC IBDV. IBD virus was detectable by AC-ELISA at this time also, indicating go that all the components needed for the stimulation of complement mediated pathology are present and as such remain as one possible mechanism for IBDV induced tissue damage. Virus neutralizing antibodies appeared first in the SPF white leghorn chickens challenged with Variant E/DEL at 6 days post challenge. All IBDV challenged groups had measurable IgG titers at day 8, but there was a subsequent decrease in titer at day 11.

INTRODUCTION

Infectious bursal disease virus (IBDV) infection induces a higher level of morbidity and mortality in older chickens than in younger chickens. Neutralizing antibodies are at detectable levels within 3 days post challenge with IBDV. This corresponds well with the 3 and 5 day time period in which the clinical signs and mortality are most severe with IBDV infection (79, 134, 135, 136). Bursal lesions induced in older chickens during IBDV infection have been described as an Arthus-type reaction (134). An arthus reaction results from the interaction of antigen-antibody complexes and serum complement (C') and is usually localized in an area where the antigen-antibody complexes are plentiful. Some of the pathology observed with IBDV infection can at least in part be attributed to this type of hyperimmune reaction (135). Lesions in the bursa, following IBDV infection, are well characterized, but evidence suggests that this virus affects other lymphoid areas in the chicken, and few if any lesions have been thoroughly characterized.

Previous experiments at the University of Arkansas have demonstrated that IBDV infection and related pathology also occurs in the proventriculus. Acute infection often results in the presence of hemorrhages in the papillae of the proventriculus. Pathology observed following IBDV infection in the proventriculus could also be a result of an Arthus type reaction. The purpose of this study was two fold: (1) to determine if there were different levels of circulating serum complement during IBDV infection with different strains of IBDV; (2) to measure neutralizing antibody levels, and time of appearance following infection with IBDV. Our goal at this point was to link complement levels and neutralizing antibody titers with the appearance and intensity of lesions in the proventriculus following IBDV infection.

MATERIALS AND METHODS

One hundred specific pathogen free (SPF) chicks were hatched at the University of Arkansas Poultry Health Laboratory Isolation Facility. Chicks were derived from fertile SPF eggs obtained from HYVAC Inc., Adel, Iowa. Chicks were placed in negative pressure isolation cages on day of hatch. Twenty-five chicks were placed in each of 4 isolation cages. All birds received water and the standard University of Arkansas diet formulation as specified by age and breed ad libitum. Lighting was maintained continuously for brooding purposes throughout the entire study utilizing a 250 watt incandescent light bulb. Birds were maintained under isolation until they reached the age of 28 days post hatch.

IBDV CHALLENGE INOCULUM PREPARATION

USDA/STC IBDV lot #92-1 was obtained from the National Veterinary Services Laboratory (NVSL) in Ames, Iowa. The virus was maintained at the University of Arkansas Poultry Health Laboratory Isolation Facility at $-70°$ C. until needed. One ampule of virus was removed from the ultralow freezer, and thawed at room temperature in a laminar flow hood. The outside of the virus ampule was wiped with 70% ETOH to remove any surface contamination. The ampule of virus was snapped open by wrapping the neck with a paper towel and breaking along the prescored line. The USDA/STC IBDV inoculum was prepared as per NVSL instructions in which 1.5 ml of lot #92-1 USDA/STC IBDV were diluted in 13.5 ml of Dulbecco's Phosphate Buffered Saline (D-PBS) (Appendix). The titer of the USDA/STC IBDV virus was previously determined to be $10^{4.1}$ EID$_{50}$/ml.

The Variant E (E/DEL) challenge virus (Intervet America, Millsboro Del.) was prepared from stock virus lot #060490. The lyophilized challenge virus aliquot was removed from the ultralow freezer ($-70°$ C.) and placed in a laminar flow hood. The outside of the vacuum sealed lyophilization container was wiped with 70% ETOH prior to removal of the aluminum seal to remove any surface contamination. The butyl rubber septum was also disinfected with 70% ETOH before insertion of needle with fluid for resuspension. A three cc syringe (Becton Dickinson and Company, Rutherford, N.J. ) was filled with two ml of sterile D-PBS through a 16 gauge 1½ inch needle (Becton Dickinson and Company, Rutherford, N.J.). The needle was then inserted through the butyl rubber seal, and the contents of the syringe was drawn into the vacuum of the lyophilization vial. The lyophilization vial was gently agitated to facilitate the rehydration of the viral pellet. The vial was then inverted and 0.5 ml of the Variant E/DEL IBDV suspension were withdrawn from the vial into the syringe. The contents of the syringe was then diluted into 74.5 ml of sterile D-PBS. The syringe was rinsed twice with the diluent solution to remove any residual virus and was then discarded into the hazardous medical waste container. The remainder of the challenge virus stock was aliquoted to cryovials, labeled and frozen at $-70°$ C. Challenge virus stock titer was $10^{5.7}$ EID$_{50}$/ml following dilution at 1:150 the challenge Var E/DEL concentration was $10_{3.0}$ EID$_{50}$/ml.

The Variant E/1084 strain IBDV challenge virus (Select Laboratories, Gainsville, Ga.) was prepared from stock virus. The challenge virus aliquot was removed from the ultralow freezer ($-70°$ C.), placed in a laminar flow hood, and thawed at room temperature. The outside of the cryovial tube was wiped with 70% ETOH prior to opening to remove any surface contamination. The virus was then diluted 1:100 and 1:1000 in sterile deionized water. The titer of the IBDV Variant E/1084 challenge stock virus was $10^{5.6}$ TCID$_{50}$/ml. Virus challenge inoculum titers were as follows: 1:100 1084-E=$10^{3.6}$ TCID$_{50}$/ml and for the 1:1000 1084-E=$10^{2.6}$ TCID$_{50}$/ml.

SPF BIRD CHALLENGE

All SPF white leghorn chickens were maintained under isolation until they reached 28 days post hatch. Each of three isolation cages of SPF white leghorn chickens were challenged with one of three different IBDV virus strains, with the fourth isolation cage remaining as the negative control. All IBDV challenges were administered bilaterally to each eye using an Eppendorf pipettor (Brinkmann, Inc., Westbury, N.Y.) and a sterile pipette tip (Costar Corp., Cambridge, Mass.). All IBDV challenge inoculum's were given at the standard 1x challenge dose.

SAMPLE COLLECTION

On days 4 and 11 post challenge 10 SPF white leghorn chickens were necropsied from each virus strain challenge group and also from the negative control. Each bird was weighed, bled, and euthanized by $CO_2$ asphyxiation. All birds were necropsied which time the bursa and proventriculus were scored for the presence of gross lesions. The bursa, spleen and proventriculus were weighed individually and results recorded. Individual tissues from each bird were cut in half, with one half being placed into 10% buffered formalin, and the other half being placed into an individual sterile sampling bag (Fisher Scientific, Pittsburgh. Pa.). Tissues in sterile sampling bags were frozen at $-20°$ C. for later analysis utilizing IBDV Antigen Capture ELISA (AC-ELISA) as described by Snyder et al (138).

ANTIGEN CAPTURE ELISA PROCEDURE

AC-ELISA test plates were prepared as described earlier in Section 1. Tissues were homogenized in AC-ELISA dilution buffer at a ratio of 1:5 tissue weight to volume. Homogenates were analyzed in duplicate against IBDV monoclonal B-29 (University of Maryland, College Park, Md.; Intervet Inc., Millsboro Del.) AC-ELISA plates as described earlier in Section 1. Plates were read and means were calculated for the paired samples within each group and the homogenates were determined to be positive or negative based on the mean absorbance values as compared to the negative and positive controls on each plate.

BLOOD SAMPLE COLLECTION AND PROCESSING

Blood samples were collected individually on 4, 6, 8 and 11 days post challenge, using 4.5 ml Sarstedt monovette™ syringes (Sarstedt, Inc. Arlington, Tex.) that contain clot activating beads and 22 gauge 1 inch needles (Becton Dickinson and Company, Rutherford, N.J.). All blood was collected by cardiac puncture on days 4 and 11 and from the brachial vein on days 6 and 8 post challenge. In order to reduce stress and insure a sufficient recovery period birds bled on days 6 and 8 post challenge were rotated based-on wing band numbers, with each successive bleed utilizing only 5 birds from the previous bleed. Serum was separated from the clot by centrifugation at 1000 rpm for 10 minutes using an IEC tabletop centrifuge and placed in both a 96 well round bottom plate (Corning Glass Works, Corning N.Y.) and into two Nalgene™ cryovials (Nalge Company, Rochester, N.Y.). All serum samples were processed and frozen at −20° C. or −70° C. within 2 hours of collection. Serum remained frozen until analyzed using the commercial KPL Infectious Bursal Disease Virus ELISA Kit and the Flock Profile™ software (Kirkegaard and Perry Laboratories, Inc., Gaithersburg, Md.), as well as virus neutralization, and hemolytic complement assay.

VIRUS NEUTRALIZATION

Virus neutralization (VN) assay of serum from experimental SPF leghorn chickens challenged at 28 days post hatch with three different IBDV strains was carried out utilizing the β procedure. In this assay the known virus concentration remains constant while the serum concentration is varied which allows for a quantitative measurement of antibody present to the known virus. This procedure is carried out in two distinct parts. In the first part, the diluted virus is mixed with diluted serum and allowed to incubate for a given period of time in order for neutralization to take place. The second part requires a method of analysis for any residual virus that might be present and can be any viable indicator assay system (45, 119).

The virus utilized in this VN analysis was the Edgar strain of IBDV virus stock at the 18th passage in primary cell culture. The virus concentration was adjusted to 100 $TCID_{50}$/0.025 ml by diluting the stock virus 1:150 in sterile tissue culture medium. Then 0.025 ml of diluted IBDV was placed in each well of 11 columns by 8 rows of a 96 well flat bottom sterile microtiter tissue culture plate (Corning Glass Works, Corning N.Y.). Column 12 received neither virus or serum and served as a cell culture viability control. Each serum sample had been previously heat inactivated at 56° C. for 30 minutes to remove non-specific viral inhibitory components and diluted 1:5 in sterile tissue culture medium (GIBCO-BRL, Grand Island, N.Y.). Then 0.025 ml of each diluted serum was placed in duplicate wells on row A of each microtiter plate using an Eppendorf micropippetor (Brinkmann, Inc., Westbury, N.Y.) and a sterile pippette tip (Costar Corp., Cambridge, Mass.). The sera were then serially diluted by using a 12-pette micropipettor (Costar Corp., Cambridge, Mass.) to transfer and mix each consecutive 0.025 ml dilution step. Pipette tips were changed after each successive dilution step to eliminate any residual carryover from the previous dilution. Infectious bursal disease virus and suspect sera were allowed to incubate at room temperature for 1 hour.

Primary chicken embryo fibroblast (CEF) cells were prepared from 9 day old SPF embryonated eggs (HYVAC, Inc., Adel Iowa). All eggs were candled to determine viability, and only eggs with healthy, active embryos were utilized. Eggs were placed in a laminar flow hood and the outside shell was disinfected with 70% ETOH. The alcohol was allowed to evaporate and the shell above the air cell was aseptically removed with a pair of sterile forceps. Forceps were then dipped in 95% ETOH and flame sterilized before removal of W the air cell membrane. Embryos were removed from the eggs and placed in sterile, warm D-PBS in a 150 mm petri dish (Fisher Scientific, Pittsburgh. Pa.). Each embryo was W processed by which the head, feet, wings and internal viscera were removed, leaving tissue of predominantly epithelial type cells. Tissues were washed two times in warm sterile D-PBS to remove nucleated red blood cells prior to enzymatic digestion. Tissue was manually homogenized by pushing through a 20 cc syringe (Becton Dickinson and Company, Rutherford, N.J.) and then subjected to a 15 minute digestion at room temperature with 0.25% trypsin solution (GIBCO-BRL, Grand Island, N.Y.) at a ratio of 4 ml of 0.25% trypsin per embryo utilized. Trypsinization was arrested by the addition of fetal bovine serum (FBS) (GIBCO-BRL, Grand Island, N.Y.), and liberated cells were separated from the trypsin digestion solution by centrifugation at 1000 rpm for 10 minutes in an IEC tabletop centrifuge. The supernatant was removed and the cellular pellet was washed one additional time in tissue culture medium., and pelleted by repeating the centrifugation step. The supernatant was again discarded and the cellular pellet was resuspended in a known volume of fresh sterile tissue culture medium. Cells were counted using a hemacytometer and assessed for viability by the trypan blue (GIBCO-BRL, Grand Island, N.Y.) dye exclusion method. The final concentration of CEF cells was adjusted to $1 \times 10^6$ cells per ml in 1X Minimum Essential Medium (GIBDCO-BRL, Grand Island, N.Y.) supplemented with 5% FBS.

Following the one hour incubation at room temperature, 100 μl of CEF cells were added to each well of the 96 well microtiter plate. Plates were then incubated at 37° C. with high humidity and an atmosphere of 5% $CO_2$ (Precision Scientific, Chicago, Ill.) for four days. Plates were examined visually for the presence of viral induced cytopathic effects (CPE) using a Nikon-diaphot phase contrast inverted microscope (Nikon Inc., Garden City, N.Y.). Lids were removed from each plate and then the contents of each well were emptied into a container of disinfectant. Remaining cellular monolayers were fixed by the addition of 95% ETOH. Following fixation, the alcohol was removed, and the plates were stained with crystal violet for approximately 30 seconds and then rinsed thoroughly in cold tap water. Virus neutralization endpoints were determined by the visual presence of intact cellular monolayers and are expressed as a mean neutralization antibody titer in FIG. 25.

HEMOLYTIC COMPLEMENT ASSAY

Hemolytic complement assay was utilized to determine the effect each of the different strains of IBDV exerted on levels of serum complement in SPF white leghorn chickens following challenge. Serum complement was analyzed for 10 individual birds on days 4, 6, 8, and 11 post challenge with IBDV. Blood was collected as described earlier, and serum aliquots were stored at −70° C. until they could be analyzed for hemolytic complement activity.

Sheep red blood cells (SRBC's) (Remel, Inc., Lenexa Kans.) were washed 3 times with 5 to 10 volumes of GBB-EDTA (Appendix). Following each wash cells were pelleted at 900 RPM for 20 minutes. Following the final wash SRBC's were resuspended in GBB-EDTA buffer to a final concentration of 5%. SRBC's were filtered through cotton to remove any clumps or clots. Then 0.5 ml of the filtered blood suspension was removed and lysed with 7.0 ml of 0.1% sodium carbonate solution. The optical density of the SRBC lysate was determined using a JENWAY 6105 UV/VIS spectrophotometer (Jenway Ltd., Essex, England) at a wavelength of 541 mu. An optical density reading of 0.700 corresponds to $1 \times 10^9$ SRBC's per ml of suspension. The final volume of the SRBC suspension was adjusted using the following formula, $V_f = V_i \cdot O.D./0.700$. Rabbit anti-sheep rbc hemolysin (Sigma Inc., St. Louis, Mo.) was diluted 1:100 in GBB-EDTA, mixed with an equal volume of 5% SRBC's, and incubated at room temperature for 45 minutes. Sensitized SRBC's were washed once in GBB-EDTA buffer and twice in $BB^{-++}$ buffer (Appendix), pelleting cells after each wash at 900 RPM in an IEC table top centrifuge for 20 minutes. SRBC's were brought to their original 5% concentration in GVB+buffer (Appendix) (134). Serum samples were removed from the −70° C. freezer, and thawed at room temperature. Fifty µl of each serum sample was diluted 1:2 in NaCl-Veronal Buffer with Ca and Mg (Appendix), and placed in duplicate in row A of a 96 well round bottom microtiter plate (Corning Glass Works, Corning N.Y.). Each row was then diluted in NaCl-Veronal Buffer with Ca and Mg in two fold steps using a 12-pette micropipettor and sterile pipette tips (Costar Corp., Cambridge, Mass.). Sensitized sheep red blood cells (sSRBC) were then added (0.050 ml) to each well and plates were covered and allowed to incubate at 37° C. for 1 hour. Plates were then viewed on a light box. The presence of a bright red color dispersed throughout the contents of the well was an indication that the sSRBC's had been lysed, the presence of compact buttons of sSRBC's was an indication that lysis had not occurred. Serum hemolytic complement titers were recorded as the reciprocal of the highest dilution at which lysis occurred.

HISTOPATHOLOGY

Tissues were placed in buffered formalin at necropsy, and processed twenty-four hours later by the method described in Section 1 (55). Tissues were examined for the presence of histopathological lesions induced by IBDV infection.

Tissues were given a numerical index score based on the presence or absence as well as the intensity of the lesions present. The score ranged from a low of "0" which indicates no lesions or pathology observed to a high of "4" which indicates extensive tissue damage.

STATISTICS

All data was entered into Microsoft™ Excel (Microsoft Corp., Redmond, Wash.) and was analyzed using SAS (124) (SAS Institute Inc., Cary N.C.). Statistical significance was determined at the $P<0.05$ level using the General Linear Models Procedure and least squared means for body weight, bursa:body weight ratios, spleen: body weight ratios, and proventriculus:body weight ratios. In addition, statistical differences were determined for means of the numerical index scores for gross lesions in the bursa and proventriculus.

RESULTS

Serum antibody levels from SPF white leghorn chickens challenged at 28 days post hatch with Variant E/DEL, Variant E/1084 and USDA/STC IBDV were not at detectable levels at 4 days post challenge (FIG. 23). Variant E/DEL initiated a small antibody response at 6 days post challenge. All IBDV challenged groups had antibody titers by day 8 post challenge. Interestingly, antibody titers at 8 days post challenge were higher than antibody titers at day 11 for all IBDV groups. The highest antibody titers were produced against Variant E/DEL at 8 days post challenge (FIG. 23).

Figure 24:
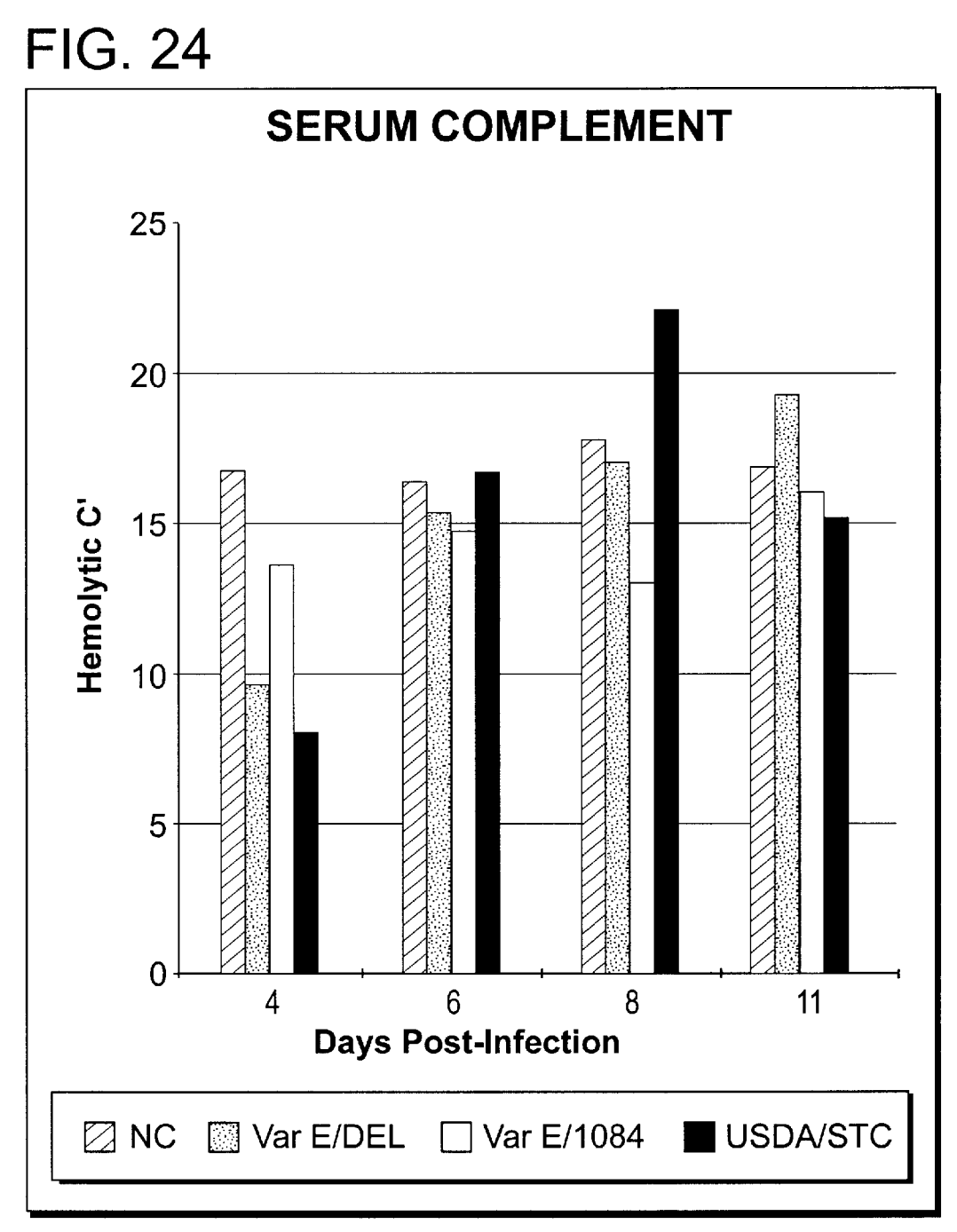

Hemolytic serum complement levels were reduced for all IBDV challenged groups at 4 days post challenge, with USDA/STC IBDV the most severely affected, followed by Variant E/DEL, and Variant E/1084 (FIG. 24). Complement levels at 6 days post challenge were essentially normal when compared to the negative control for all IBDV challenged groups. Complement levels at 8 days post challenge were elevated for USDA/STC IBDV, lower for Variant E/DEL IBDV, and significantly lower for Variant E/1084 IBDV. Complement levels at 11 days post challenge were essentially normal with a slight elevation in Variant E/DEL IBDV (FIG. 24).

Figure 25:
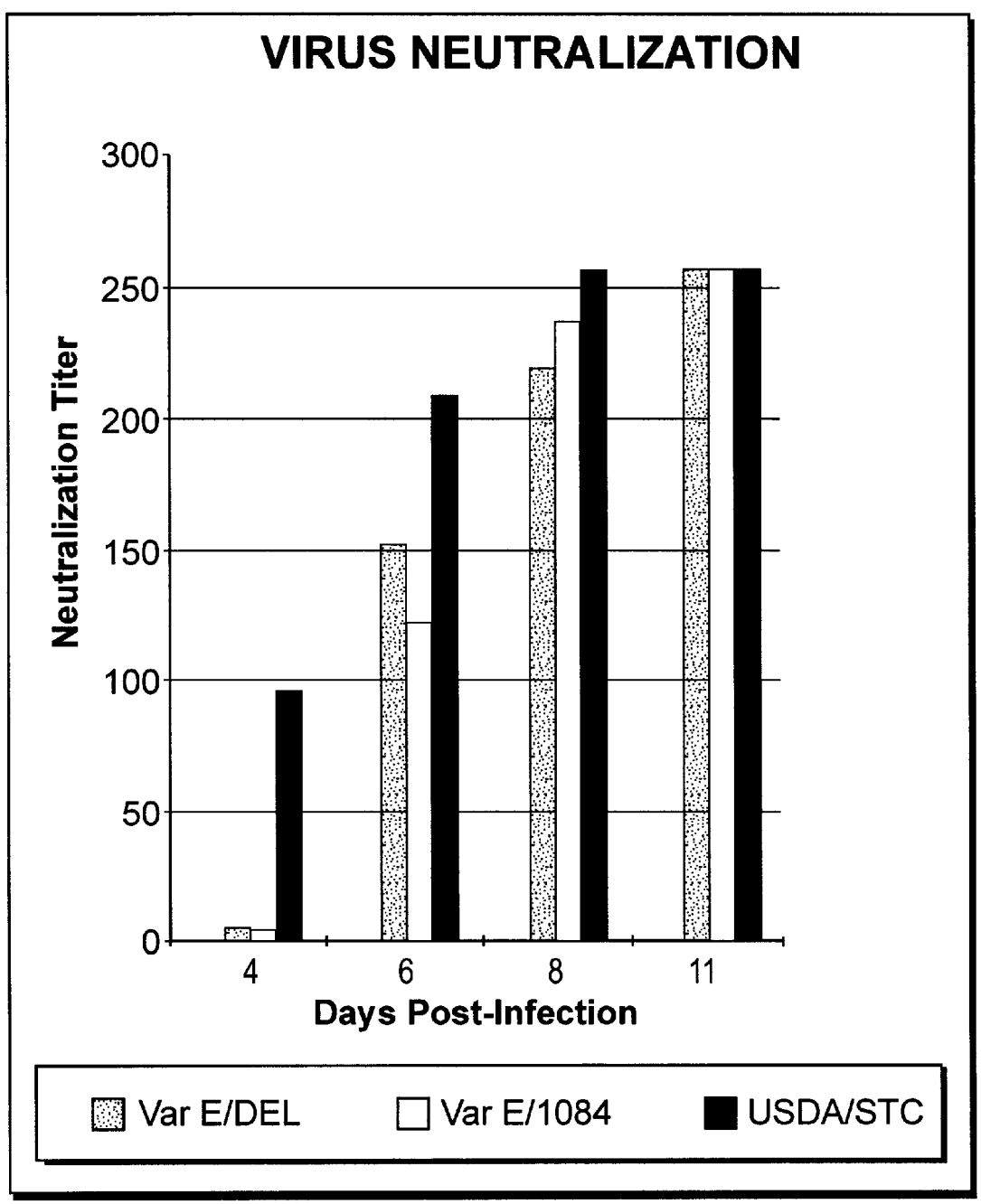
FIG. 25 is a diagram showing virus neutralization (VN) levels from SPF white leghorn chickens challenged at 28 days post hatch with Variant E/DEL, Variant E/1084, and USDA/STC IBDV at 4, 6, 8 and 11 days post challenge.

Neutralizing antibody was present in all IBDV challenge groups at 4 days post challenge (FIG. 25). Neutralizing antibody levels were higher in the USDA/STC IBDV challenge group at 4 days post challenge when compared to all other challenge groups. Neutralizing antibody titers at 6 days post challenge were highest with USDA/STC IBDV, followed by Variant E/DEL and Variant E/1084. Neutralizing antibody titers to IBDV at 8 days post challenge were highest against USDA/STC IBDV, followed by Variant E/1084, and Variant E/DEL. Neutralization antibody titers at day 11 post challenge are all at the maximum dilution value tested regardless of the challenge virus strain (FIG. 25).

Tissues harvested at day 4 and 11 post challenge were analyzed for the presence of IBDV antigen by AC-ELISA. The bursae of all IBDV challenge groups were positive at 4 days post challenge (Table 27). The spleens of fifty percent of the Variant E/1084 IBDV challenged SPF leghorn chickens were positive at 4 days post challenge, all other groups tested negative in the spleen. Proventricular homogenates tested positive for all IBDV challenge groups at 4 days post challenge. However, Variant E/DEL had a much lower incidence of virus detection as compared to Variant E/1084 and USDA/STC IBDV (Table 27). All tissues for all IBDV challenge groups tested negative by AC-ELISA at 11 days post challenge (Table 28).

Microscopic lesions in the bursa and proventriculus at 4 days post challenge were detected in all IBDV challenge groups (Table 29). However, both the Variant E/DEL IBDV, and Variant E/1084 IBDV seem to have less of a trophism for the proventriculus than USDA/STC IBDV (Table 29). Microscopic lesions were detected in the bursa at 11 days post challenge in all IBDV challenge groups, but were absent from the proventriculus (Table 30).

DISCUSSION

Serum antibody appears at day 6 post challenge for only one experimental group Variant E/DEL. On day 8 post challenge serum antibody levels are measurable for all IBDV experimental challenge groups, but again the highest titers are against both of the Variant E IBDV strains. Antibody levels at 11 days post challenge are still highest for the Variant E/IBDV groups as the USDA/STC IBDV group continues to be the poorest antibody producer. This may reflect the more extensive damage present in the bursa following challenge with USDA/STC IBDV and because of the inability to mount an effective immune response because of damage to immune cells.

Complement levels in all IBDV challenged groups were decreased below the negative controls at day 4 post challenge as described in a number of papers (79, 134, 135, 136). It would appear that hemolytic complement reaches normal levels at 6 days post challenge. However, at day 8 post challenge birds challenged with USDA/STC IBDV continue to increase complement levels seeming to overcompensate for the deficiency at 4 days post challenge. By day 11, complement levels appear normal for all but the Variant E/DEL which appear to be increasing. The levels of complement following IBDV challenge appear to be cyclic at their lowest levels when virus populations are highest (detectable by AC-ELISA), and increasing with the corresponding increased levels of neutralizing antibodies, and serum IgG titers. The induction of pathology as a result of the presence of IBDV antibody-antigen complexes and complement interaction would seem to fall on day 6 post challenge. Interestingly, lesions observed in the tissues examined at 4 and 11 days following IBDV challenge were the most severely affected in the USDA/STC IBDV challenge group. This corresponds well with the presence of a high neutralizing antibody titer on day 6 post challenge, at a time when complement levels are returning to normal. Ideally, complement levels, neutralizing antibody levels, IgG antibody titers and virus AC-ELISA should be measured at much closer intervals to fully elucidate this viral induced pathogenic mechanism.

SECTION 6

THE INTERACTION OF INFECTIOUS BURSAL DISEASE VIRUS (USDA/STC) AND COPPER SULFATE IN THE PRODUCTION OF LESIONS ASSOCIATED WITH PROVENTRICULITIS IN BROILER CHICKENS

SUMMARY

Broiler chickens challenged with USDA/STC IBDV at 35 days post challenge exhibited gross lesions in the bursa and proventriculus at 4 days post challenge in the presence and absence of copper sulfate. Antigen capture ELISA (AC-ELISA) analysis of tissue homogenates indicates that the USDA/STC IBDV was present at 4 days post challenge and was not influenced by the presence of dietary copper sulfate. Broiler chickens did produce an immune response to IBDV following challenge.

INTRODUCTION

Previous experiments at the University of Arkansas indicated that challenge with infectious bursal disease virus (IBDV) was exacerbated by the presence of dietary copper sulfate supplementation. Bayyari et al (5) reported a similar finding with broiler chickens given supplemental copper sulfate in the presence of challenge with a proventricular tissue homogenate containing an undefined pathogen. SPF white leghorn chickens showed decreased weights, increased lesions in the proventriculus and higher mortality following challenge with USDA/STC IBDV in the presence of copper sulfate. The purpose of this experiment was to attempt to reproduce the syndrome seen in SPF white leghorn chickens in commercial broiler chickens.

MATERIALS AND METHODS

One hundred twenty commercial broiler chickens were procured from a local hatchery. Chicks received Marek's vaccine at the hatchery by subcutaneous injection but were given no other vaccines. Chicks were dispersed into battery cages at day of hatch, and sequestered by treatment group. All birds received the standard University of Arkansas diet formulation as specified by age and water ad libitum. Chicks given the diet supplemented with copper sulfate received it beginning on day 1 and throughout the entire study at the rate of 1 lb/ton.

VIRUS CHALLENGE INOCULUM PREPARATION

USDA/STC IBDV challenge inoculum was prepared from lot #92-1 (NVSL, Ames Iowa.) as follows: The virus was removed from the ultralow freezer (−70° C.), and thawed at room temperature in a laminar flow hood. The outside of the virus containing glass ampule was wiped with 70% ETOH, to remove any surface contamination. The ampule of virus was snapped open by wrapping the neck with a paper towel and breaking along the prescored line. The virus was then diluted 1:10 by mixing 1.5 ml of USDA/STC IBDV virus into 13.5 ml of Dulbecco's Phosphate Buffered Saline (D-PBS) (Appendix A).

BROILER CHALLENGE

Broiler chickens were challenged or, day 35 post hatch (PH) with the USDA/STC IBDV prepared inoculum as described previously. Infectious bursal disease virus challenge was administered to each individual bird bilaterally to the eye (30 $\mu$l per eye) using an Eppendorf micropipettor (Brinkmann Inc., Westbury, N.Y.) and a sterile pipette tip (Costar Corp., Cambridge, Mass.).

SAMPLE COLLECTION

On days 4 and 11 post challenge 25 birds were necropsied from each virus challenge group and an additional 10 birds from the negative control. Each bird was weighed, bled, and euthanized by $CO_2$ asphyxiation. All birds were necropsied at which time the bursa and proventriculus were scored for the presence of gross lesions. The bursa, spleen, and proventriculus were individually weighed and results recorded. Tissues from each of the birds were cut in half, with one half being placed into 10% buffered formalin, and the other half being placed into a sterile sampling bag (Fisher Scientific, Pittsburgh, Pa.). Tissues in sterile sampling bags were frozen at −20° C. for later analysis utilizing IBDV Antigen Capture ELISA(AC-ELISA), as described by Snyder et al (138).

ANTIGEN CAPTURE ELISA PROCEDURE

AC-ELISA test plates were prepared as described earlier in Section 1. Tissues were homogenized in AC-ELISA dilution buffer at a ratio of 1:5 tissue weight to volume. Homogenates were analyzed in duplicate against IBDV monoclonal B-29 AC-ELISA plates as described earlier in Section 1. Plates were read and means were calculated for the paired samples within each group and the homogenates were determined to be positive or negative based on the mean absorbance values as compared to the negative and positive controls on each plate.

BLOOD SAMPLE COLLECTION AND PROCESSING

Blood samples were collected on days 1 and 35 post hatch and days 4 and 11 post challenge from individual chickens using 4.5 ml Sarstedt monovette™ syringes (Sarstedt, Inc., Arlington, Tex.) containing clot activating beads and 22 gauge 1½ inch needles (Becton Dickinson and Company, Rutherford, N.J.). Serum was separated from the clot by centrifugation at 1000 rpm for 10 minutes using an IEC tabletop centrifuge. Serum was collected and placed in both a 96 well round bottom plate (Corning Glass Works, Corning N.Y.) and into Nalgene™ cryovials (Nalge Company, Rochester, N.Y.) All serum samples were frozen at −20° C. until they were analyzed using the commercial KPL Infectious Bursal Disease Virus ELISA Kit and the Flock Pro-file™ software (Kirkegaard and Perry, Laboratories, Inc., Gaithersburg, Md.).

HISTOPATHOLOGY

Tissues were placed in buffered formalin at necropsy, and processed twenty-four hours later by the method described in Section 1 (55). Tissues were examined for the presence of histopathological lesions induced by IBDV infection. Lesions in the lamina propria of the proventriculus were predominantly pleomorphism of the lymphoid cells in the mucosa along with lymphocyte depletion. Lesions in the bursa were predominantly lymphoid depletion with accompanied follicle degeneration.

Tissues were given a numerical index score based on the presence or absence as well as the intensity of the lesions present. The score ranged from a low of "0" which indicates no lesions or pathology observed to a high of "4" which indicates extensive tissue damage.

FEED ANALYSIS

Feed samples were pulled at the end of the study and sent for analysis to establish that the two diets varied only in the different levels of copper sulfate present. Feed samples were analyzed at the Center for Excellence in Poultry Science, Central Analytical Laboratory. The diet without copper sulfate supplementation contained 14.95 ppm copper. The diet with copper sulfate supplementation contained 126.35 ppm copper.

STATISTICS

All data was entered into Microsoft™ Excel (Microsoft Corp., Redmond, Wash.) and was analyzed using SAS (3) (SAS Institute Inc., Cary N.C.). Statistical significance was determined at the $P<0.05$ level using General Linear Models Procedure and least squared means for body weight, bursa-:body weight ratios, spleen: body weight ratios, and proventriculus:body weight ratios. In addition, statistical differences were determined for means of the numerical index scores for gross lesions in the bursa and proventriculus.

RESULTS

Figure 26:
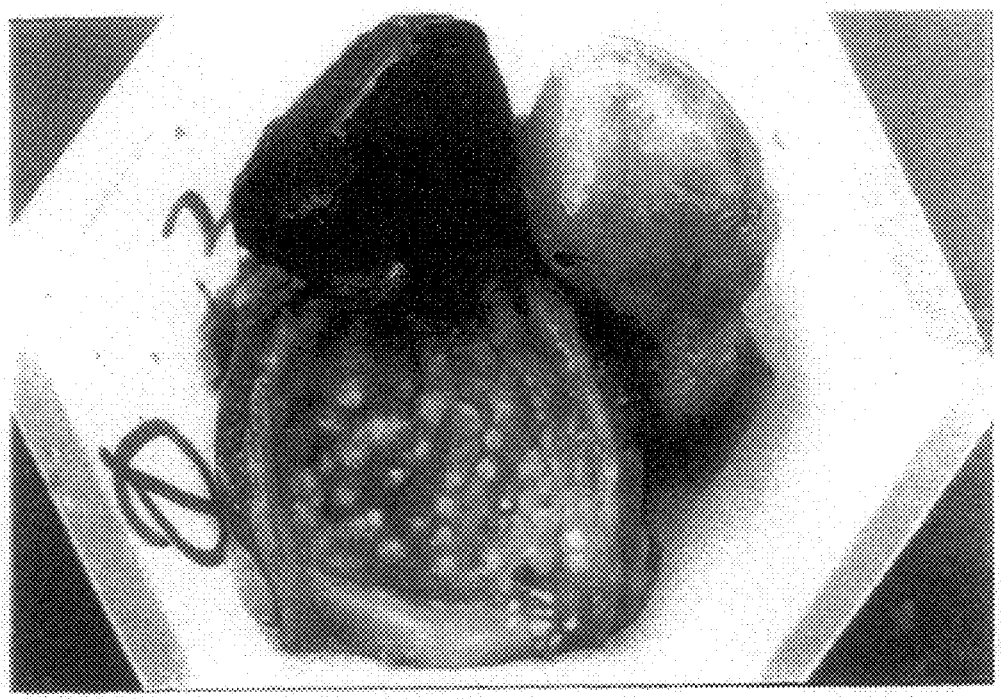
FIG. 26 shows the proventriculus, spleen and bursa from 43 day post hatch broiler without USDA/STC IBDV challenge and in the absence of copper sulfate supplementation.

The proventriculi from broilers challenged with USDA/STC IBDV in the presence of copper sulfate at 35 days post hatch had gross lesions involving the discoloration of the mucosal lining and enlargement of the papillae (FIG. 27) as compared to an unchallenged hatchmate without copper sulfate supplementation (FIG. 26). Virus induced effects are evident in the bursa (atrophy) and spleen (splenomegaly) (FIG. 27) when compared to the negative control bursa and spleen (FIG. 26).

Organ to body weight ratios were compared for each experimental group at day 4 and day 11 post challenge with USDA/STC IBDV. Significant differences were noted only in the spleen at 4 days post challenge for the USDA/STC IBDV and USDA/STC IBDV+copper sulfate (Table 31). Bursa to body weights ratios at 11 days post challenge were significantly higher for all challenge groups that received USDA/STC IBDV. Spleen to body weight ratios were significantly lower only in the USDA/STC IBDV challenged group (Table 32).

Gross lesion scores for the proventriculus were significant for only two criteria, which was different for each necropsy day. Papillae were significantly affected in the USDA/STC IBDV challenged group only at 4 days post challenge. Feed impaction was of significantly higher incidence in the challenge group that received USDA/STC IBDV only (Table 33).

AC-ELISA analysis of bursal and proventricular homogenates at 4 and 11 days post challenge with USDA/STC IBDV indicated the presence of virus in both the bursa and the proventriculus at 4 days post challenge only. The number of AC-ELISA detectable positives was not significantly different between USDA/STC challenged groups in the presence or absence of copper sulfate for either the bursa or the proventriculus.

Microscopic lesions at 4 and 11 days post challenge were assessed for the proventriculus and bursa (Table 35). Bursal lesions at 4 days post challenge were present in the USDA/STC IBDV challenged groups in the presence or absence of copper sulfate. Proventricular lesions at 4 days post challenge are present in the USDA/STC IBDV challenged groups in the presence or absence of copper sulfate. Bursal lesions at 11 days post challenge were present in all experimental groups. Proventricular lesions were not present in any of the experimental groups at 11 days post challenge.

Figure 28:
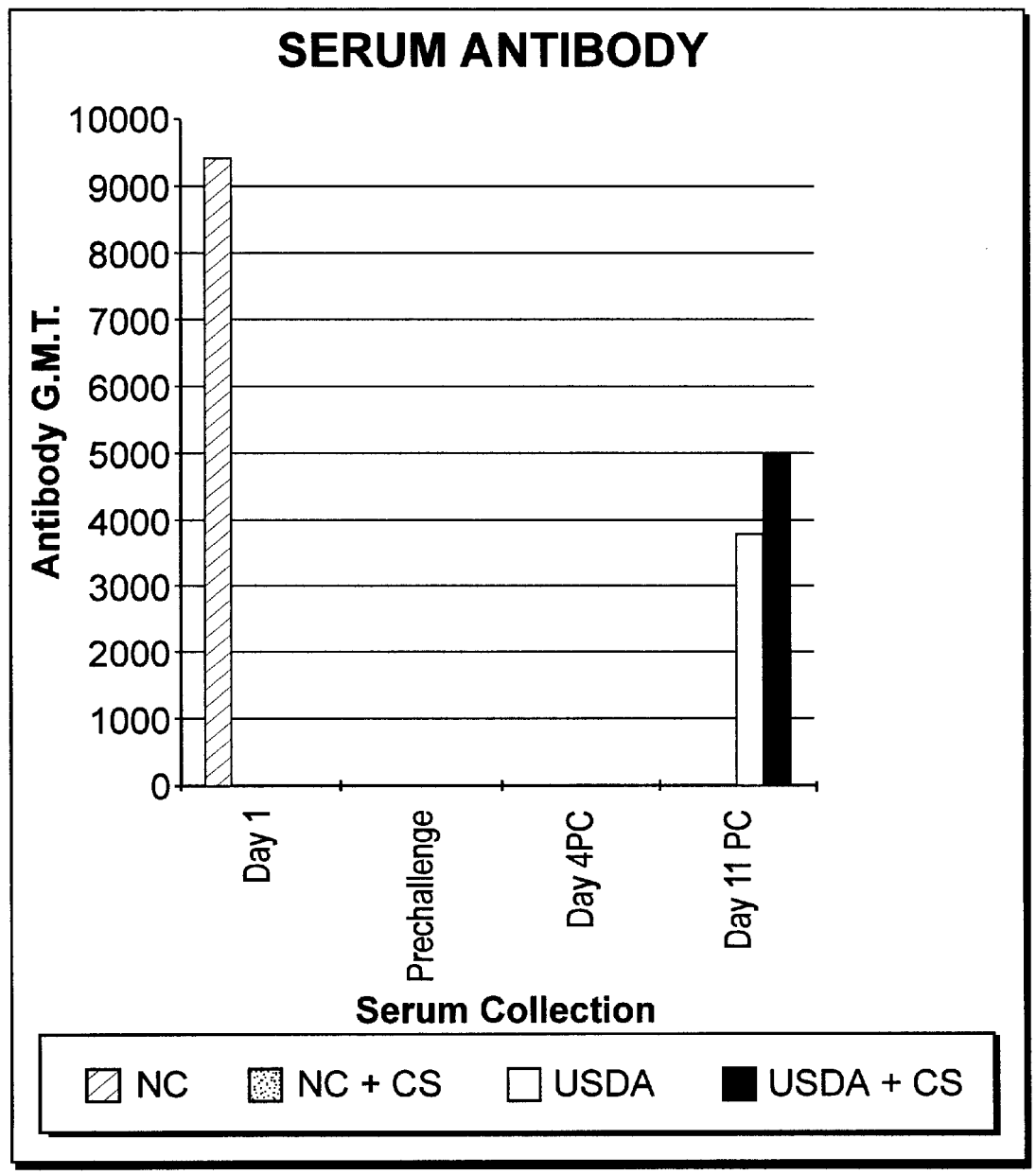
FIG. 28 is a diagram showing serum antibody levels of commercial broilers at day of hatch, 35 days post hatch and 4 and 11 days post challenge with USDA/STC IBDV in the presence or absence of copper sulfate.

Maternal serum antibody titers were in excess of 9000 at day of hatch but had dropped below detectable levels by 35 days post hatch. Immune response following challenge was detectable at 11 days post challenge. Post challenge titers did not approach antibody levels present at hatch (FIG. 28).

DISCUSSION

Figure 27:
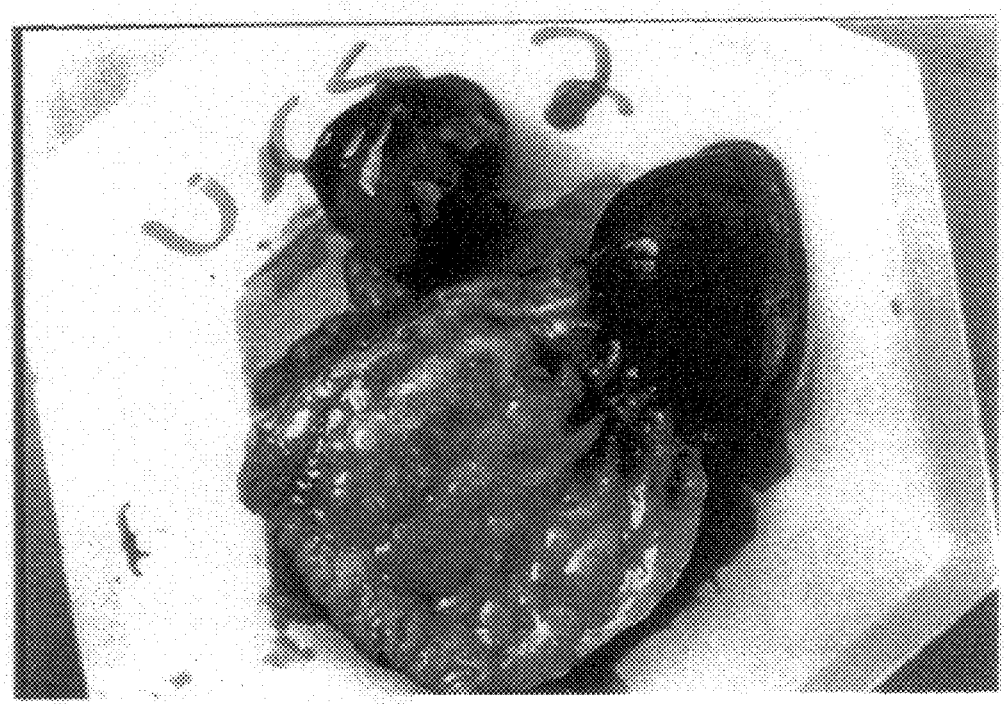
FIG. 27 shows the Proventriculus, spleen and bursa from a 43 day post hatch broiler at 4 days post challenge with USDA/STC IBDV in the presence of copper sulfate dietary supplement.

The gross lesions visible following challenge with USDA/STC IBDV in the proventriculus indicate that there is an effect on the mucosal surface of the proventriculus (FIG. 27). The enlarged papillae were also present in the unchallenged group that received copper sulfate but the yellow discoloration was absent (data not shown). This coloration is reminiscent of the pigment that is absorbed from corn in the diet, however, birds exhibiting yellow mucosal proventricular linings did not exhibit pale shanks or bleaching. The enlarged papillae have been seen previously in SPF white leghorn chickens following challenge with USDA/STC IBDV in the presence and absence of copper sulfate but were much less evident.

AC-ELISA indicates the presence of virus in the bursa and proventriculus. Virus presence within the tissues does not appear to be influenced by the presence of copper sulfate. AC-ELISA has not been capable of picking up tissue homogenate positives in any of the experimentally challenged birds beyond day 4 post challenge. This appears to be a reflection of the sensitivity of the assay as well as the rapid viral replication and clearance.

Organ to body weight ratios indicated that the virus was capable of exerting an effect. There were no significant differences in body weights following challenge with USDA/STC IBDV in the presence or absence of dietary copper sulfate. Bayyari et al reported a reduction in body weights and feed conversion following challenge of day old broilers with an undefined pathogen in the presence of copper sulfate. This phenomenon Was also noted in SPF white leghorn chickens following challenge with USDA/

STC IBDV in the presence of copper sulfate. The microscopic tissue lesions should confirm whether or not the lesions are typical of IBDV infection.

Microscopic lesions in the bursa were present in the USDA/STC IBDV challenged group at a higher frequency than the USDA/STC IBDV+copper sulfate group. It would appear that infection of the bursa is delayed or there is some type of interference when copper sulfate is present. At 11 days post challenge lesions are present in all experimental groups indicating that the USDA/STC IBDV virus had spread laterally within the experimental house. Proventricular lesions at 4 days post challenge are of higher incidence in the USDA/STC IBDV+copper sulfate experimental group. At 11 days post challenge lesions are absent from the proventriculus in all experimental groups, which is similar to what is described in SPF white leghorn chickens.

Serum antibody titers demonstrate that immunity to infectious bursal disease virus is not of long duration when relying entirely on maternally derived antibody. It is necessary to point out that IBDV challenge did not take place until 35 days post hatch. The goal was to allow for the catabolism of maternally derived antibody so that is was possible to infect these birds with IBDV. Antibody levels were not checked on a regular interval and may have waned well before challenge took place.

SECTION 7

Isolation and Characterization of Infectious Bursal Diseasevirus from Broiler Chickens Exhibiting Symptoms of Proventriculitis

SUMMARY

To date submissions for AC-ELISA screening of broiler flocks affected with proventriculitis have encompassed 46 facilities from 6 different states. Broiler chicken tissue submissions come from flocks ranging in age from 14 to 35 days post hatch. Virus immunoprecipitation following AC-ELISA screening has resulted in the isolation of 5 infectious bursal disease viruses of proventricular origin. Virus isolations are primarily from broiler flocks ranging in age from 22–29 days post hatch.

Inoculation of proventricular origin IBDV isolates into 28 day post hatch SPF white leghorn chickens, revealed the production of lesions associated with infectious bursal disease virus infection. At 11 days post challenge all SPF white leghorn chickens demonstrate IgG antibody titers to IBDV following screening of serum with a commercial IBDV ELISA kit.

RT/PCR-RFLP analysis of new proventricular IBDV isolates indicate that the viruses have a unique restriction enzyme pattern within a 700 bp fragment of the VP2 genomic region. The new isolates appear to share characteristics of both the Delaware variant and a more recent California IBDV isolate from the bursa.

INTRODUCTION

Poultry producers have continued to report increased incidence of proventriculitis in broiler flocks as well as the associated processing complications. Producers were given an option to submit tissues to the University of Arkansas from affected flocks for initial screening by Antigen capture ELISA (AC-ELISA) assay. The AC-ELISA technology was obtained through a cooperative agreement with University of Maryland, College Park, Md. and Intervet Inc., Millsboro, Del. Proventricular tissues from field submissions which tested positive by AC-ELISA were then immunoprecipitated using a IBDV monoclonal antibody B29 (University of Maryland, College Park, Md.; Intervet Inc., Millsboro, Del.) in an attempt to isolate any IBDV present. The purpose of this experiment was to isolate and characterize new IBDV isolates of proventricular origin from broiler chickens experiencing proventriculitis.

MATERIALS AND METHODS

Tissues from birds with proventriculitis were collected from affected farms and placed in individual sterile sample bags ( Fisher Scientific, Pittsburgh. Pa.) and frozen until they could be shipped to the University of Arkansas. Suspect tissues were received at the University of Arkansas Poultry Health Laboratory and stored at −20° C. until they could be processed.

Each farm from which affected tissues were collected was given a University of Arkansas case number so that they could be identified. All tissues were prepared for Antigen Capture ELISA (AC-ELISA) analysis by the following procedure. Tissues were thawed, weighed, and homogenized . Homogenization was accomplished as described earlier in Section 1. Following homogenization, tissues were resuspended in a volume of AC-ELISA Sample Dilution Buffer (Appendix), that was equivalent to 4 times the weight of the tissue sample. The resulting end dilution being 1:5 or 20% tissue by weight to volume. Duplicate sample templates were then prepared for the AC-ELISA test.

All bursal sample homogenates were screened for the presence of infectious bursal disease virus (IBDV) at a final tissue concentration of 1:40. All proventricular tissue homogenates were screened for the presence of IBDV at a final tissue concentration of 1:10. Samples were screened only against monoclonal antibody B29 (University of Maryland, College Park, Md.; Intervet Inc., Millsboro, Del.). After completion of all the AC-ELISA test requirements as described earlier in Section 1, plates were read using BIO-TEK model EL 312e ELISA reader. Optical densities for each well were determined, recorded by the reader, and printed- Samples were determined to be positive or negative based on the optical density reading they produced in comparison to the negative and positive control.

VIRAL IMMUNOPRECIPITATION

Samples that were determined to be positive, were then immunoprecipitated utilizing IBDV monoclonal antibody B29 and Pansorbin Cells™ (Calbiochem, LaJolla, Calif.) using methods described by Kessler (75) and Harris (41) . Briefly Pansorbin cells (10% w/v cell suspension in D-PBS) were washed three times in NET+NP40 buffer (Appendix), and the pellet was resuspended in NET+NP40 to the original volume to restore the 10% suspension. Sixty μl of proventricular tissue homogenate was added to 20 μl of IBDV Mab B-29 ascitic fluid and incubated at room temperature for 60 minutes. Twenty-five μl of NET+NP40 and 25 μl of washed pansorbin cells were added to the antigen antibody complex and incubated at room temperature for 15 minutes. The Pansorbin antigen:antibody complex was then pelleted for 2 minutes in an Eppendorf microfuge (Brinkmann Inc., Westbury, N.Y.) at 6000 rpm. The pellet was then resuspended and washed three times in NET+NP40 buffer. Following the final wash the pellet was retained. The precipitated virus:antibody complex was inoculated into SPF eggs.

SPF EGG INOCULATION

Eggs utilized were laboratory grade specific pathogen free (SPF) (HYVAC Inc., Adel, Iowa). Eggs were incubated to the 9th day of development, at which time they were removed from the incubator, and candled to determine viability. All viable eggs were Ken manually ha manipulated to expose the chorioallantoic membrane (CAM). Each sample was then injected onto the CAM of 5 fertile SPF eggs. Immunoprecipitated samples were introduced onto the CAM utilizing a 1 cc tuberculin syringe and 26G ½ inch needle (Becton Dickinson and Company, Rutherford, N.J.). Egg shell openings were then closed using melted wax. Inoculated eggs were incubated at 37° C. with high humidity. Eggs were candled daily to determine viability of experimental embryos. As embryo deaths occurred, non-viable embryos were removed, recorded and place at 4° C. until all embryos could be visually examined for the presence or absence of viral lesions. After 7 days of incubation, all remaining viable embryos were chilled at 4° C. overnight.

Examination of embryos for viral lesions was accomplished by the removal of the external side shell and shell membrane of each egg. Chorioallantoic membranes were visually examined for the presence of viral infection. The number of affected membranes was recorded for each experimental isolate. The chick embryo was then removed from the egg and any external lesions present were recorded. The final examination was of the internal organs of each embryo. Target organs examined were the liver, spleen, proventriculus, and bursa of Fabricius. All affected tissues including the chorioallantoic membrane were harvested into a sterile container, labeled, homogenized and diluted in Dulbecco's phosphate buffered saline (D-PBS) with 10 $\mu$g/ml gentamycin (Schering Plough Union, N.J.) and 250 $\mu$g/ml of Amphotericin B (GIBCO-BRL, Grand Island, N.Y.). The egg inoculation procedure was then repeated up to three passages at which time samples not exhibiting viral lesions were discarded.

SPF BIRD CHALLENGE

Tissues and CAMs harvested from affected embryos on the third passage were then homogenized, and inoculated into 28 day post hatch SPF white leghorn chickens (HYVAC, Inc., Adel, Iowa). The inoculum was administered 30 $\mu$l bilaterally to the eye using an Eppendorf micropipettor (Brinkmann Inc., Westbury, N.Y.) and a sterile pipette tip (Costar Corp., Cambridge, Mass.). Approximately 50% of the SPF white leghorn chickens were then necropsied at 4 and 11 days post exposure. Birds were weighed, bled, euthanized by $CO_2$ asphyxiation, and examined by necropsy for the presence of viral lesions. The bursa and spleen were visually scored for the presence of gross lesions. In addition, bursa, spleen, and proventriculus were harvested, weighed, and cut into three pieces with one section going into 10% buffered formalin, one section for AC-ELISA (138) and the final section for reverse transcriptase polymerase chain reaction with restriction fragment length polymorphism analysis (RT/PCR-RFLP) (60). Serum antibody titers were determined utilizing a commercial ELISA kit for IBDV (Kirkegaard and Perry, Laboratories Inc., Gaithersburg, Md.).

HISTOPATHOLOGY

Tissues were placed in buffered formalin at necropsy, and processed twenty-four hours later by the method described in Section 1 (55). Tissues were examined for the presence of histopathological lesions induced by IBDV infection.

Tissues were given a numerical index score based on the presence or absence as well as the intensity of the lesions present. The score ranged from a low of "0" which indicates no lesions or pathology observed to a high of "4" which indicates extensive tissue damage.

STATISTICS

All data was entered into Microsoft™ Excel (Microsoft Corp., Redmond, Wash.). and were analyzed using SAS (5) (SAS Institute Inc. Cary N.C.). Statistical significance was determined at the $P<0.05$ level using General Linear Models Procedure and least squared means for body weight, bursa-:body weight ratios, spleen: body weight ratios, and proventriculus:body weight ratios. In addition, statistical differences were determined for means of the numerical index scores for gross lesions in the bursa and proventriculus.

RESULTS

Figure 29:
FIG. 29 shows an enlarged proventriculus in a 22 day post hatch production broiler chicken.
Figure 30:
FIG. 30 shows the internal characteristics of acute proventriculitis in 27 day post hatch production broiler. Note the hemorrhages in the papillar ducts, loss of papillar definition, and discoloration of the mucosal surface.

FIG. 29 demonstrates an abnormally enlarged proventriculus in a 22 day post hatch broiler. FIG. 30 illustrates the internal lesions in a 27 day post hatch broiler that are commonly associated with proventriculitis syndrome in the field. Note the hemorrhages in the papillae, the loss of papillae definition, and the abnormal coloration of the mucosal surface.

Microscopic lesions in the bursa of SPF white leghorn chickens challenged with field IBDV isolates were present in all but two challenged groups at day 4 and 11 post challenge. Microscopic lesions in the proventriculi of SPF white leghorn chickens challenged with field IBDV isolates were present on day 4 in all but two of the challenge groups. There were no microscopic lesions in the proventriculus at 11 days post challenge (Table 35). Samples W/L #22 and #33 consistently tested negative in inoculated birds although they appeared to produce lesions in embryonated eggs. SPF leghorn chickens challenged with these two isolates did not produce serum antibodies to IBDV. These isolates will be screened for the presence of other pathogens but at this point do not appear to be IBDV.

Gross lesion scores from the proventriculus were not significantly diff(Vent from the negative control at 4 or 11 days post challenge for any of the suspect virus challenge groups (data not shown).

AC-ELISA analysis of bursal and proventricular homogenates from SPF white leghorn chickens challenged with USDA/STC IBDV and proventricular origin field isolates at 28 days post hatch tested positive in the bursa at 4 days post challenge with the exception of the two isolates discussed earlier. All bursal homogenates tested negative at 11 days post challenge. Proventricular homogenates from field isolates had fewer positives when compared to the USDA/STC IBDV.

Organ to body weight ratios of SPF white leghorn chickens demonstrate the induction of significant effects on the bursa and spleen at 4 days post challenge with field isolates RB/Texas 3 and 4, Farm 57–7, and W/L #39 (Table 37). There were no significant differences in the proventriculus to body weight ratio on day 4 post challenge (Table 37). The bursa to body weight ratio was lower than the negative control in all challenge groups with the exception of W/L #22 and #33 at 11 days post challenge (Table 38).

Figure 33:
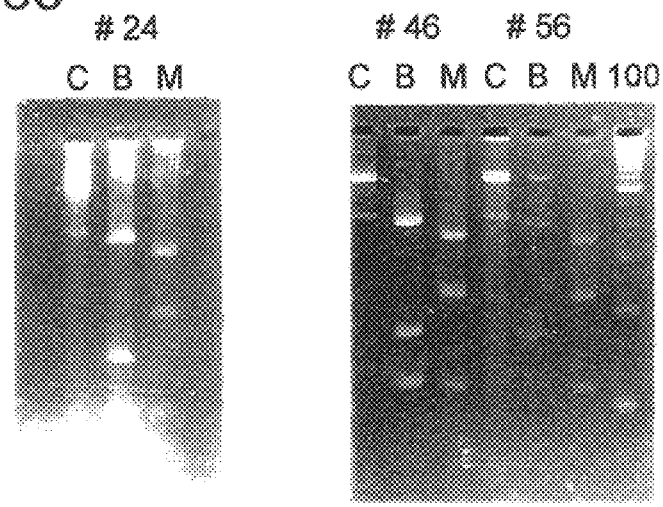
FIG. 33 shows the RT/PCR-RFLP analysis of proventricular and bursal homogenates from the two original proventricular IBDV isolates at 4 days post challenge in 28 day post hatch SPF white leghorn chickens.
Figure 34:
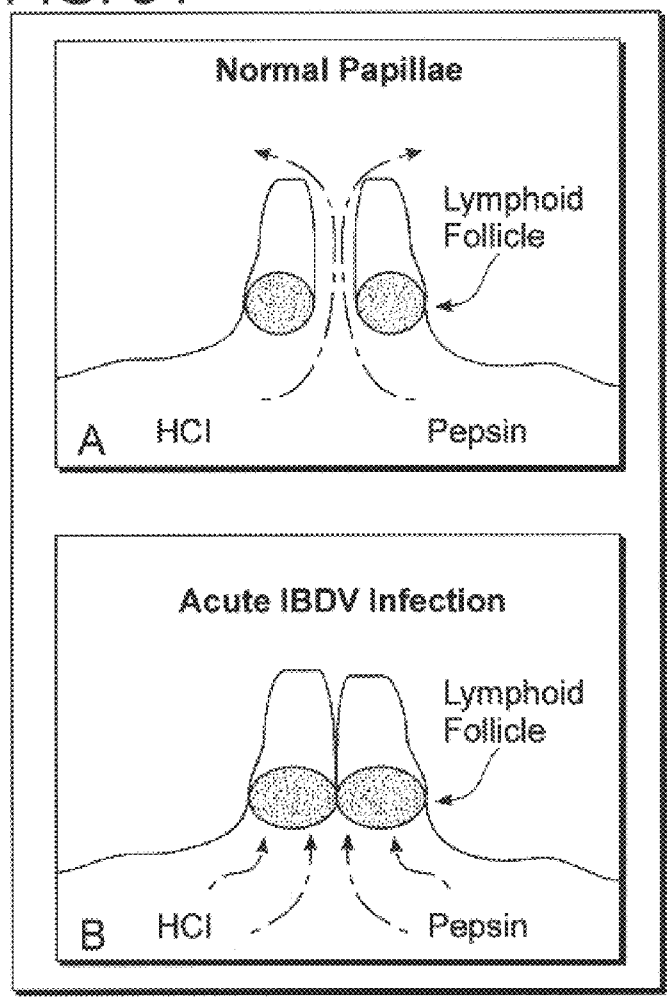
FIG. 34A is a schematic cross-section representation of normal papillae.
FIG. 34B is a schematic cross-section representation of abnormal papillae affected by acute IBDV infection.

RT/PCR-RFLP analysis of new proventricular IBDV isolates RB/Texas 3 and RB/Texas 4 indicate that the viruses have a unique restriction enzyme pattern within a 700 bp fragment of the VP2 genomic region. The agarose gel electrophoretic separation of digested and undigested PCR products is demonstrated in FIG. 33. Samples #24 and #34

(not shown) are PCR amplifications of bursa and proventriculus respectively from SPF white leghorn chickens challenged with isolate RB/Texas 3. Sample #34 did not amplify during the RT/PCR reaction. Samples #46 and #56 are RT/PCR amplification of bursa and proventriculus respectively from SPF white leghorn chickens challenged with isolate RB/Texas 4. RT/PCR products from both RB/Texas 3 and RB/Texas 4 are identical with respect to their restriction profile in this 700 bp VP2 fragment. This was expected as both uses isolates were obtained from the same poultry facility.

Figure 31:
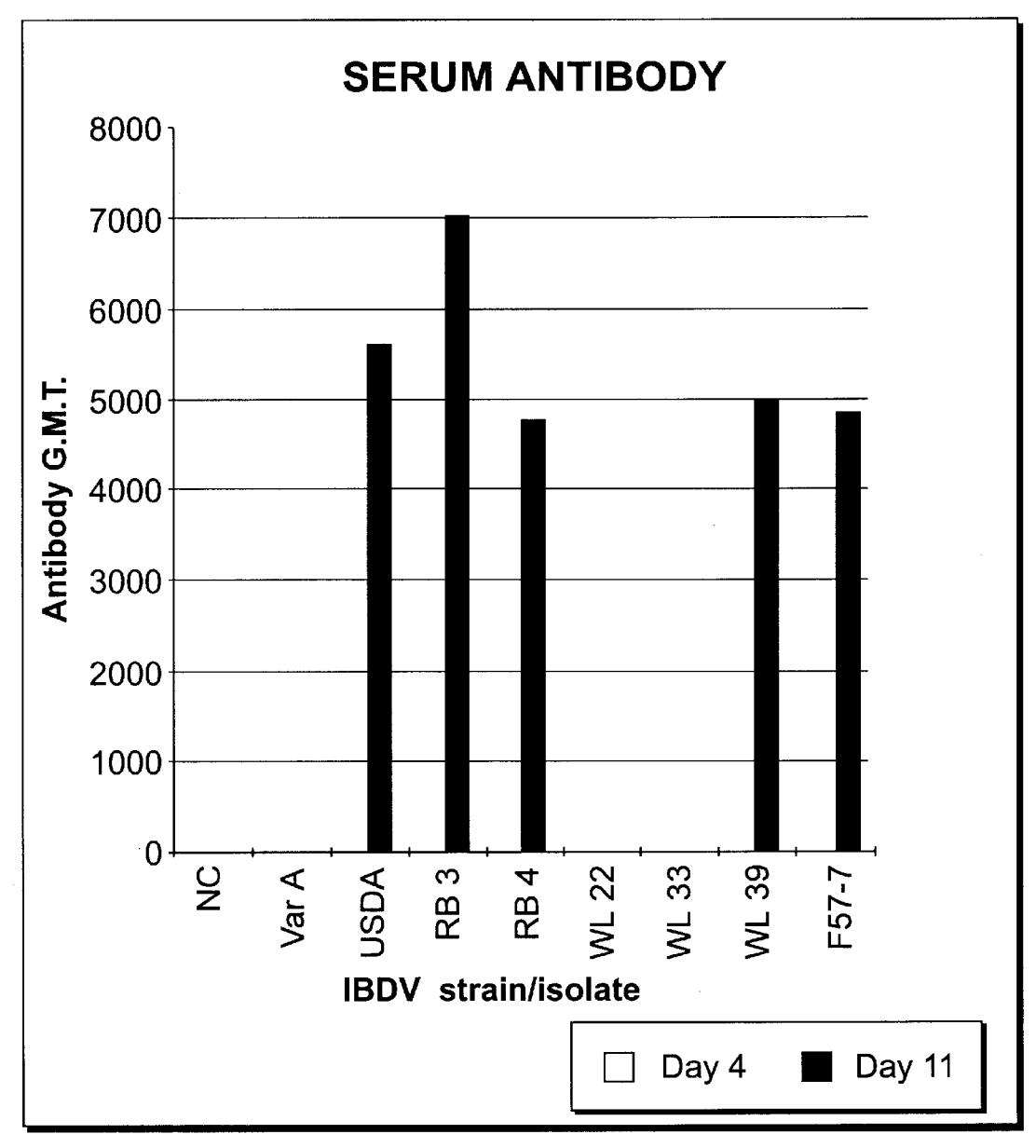

As shown in FIG. 31, serum antibody response of 28 day post hatch SPF white leghorn chickens following challenge with USDA/STC IBDV and proventricular origin IBDV field isolates indicate that all challenge groups with the exception of W/L #22 and #33 produced measurable levels of antibodies at 11 days post challenge.

DISCUSSION

Figure 32:
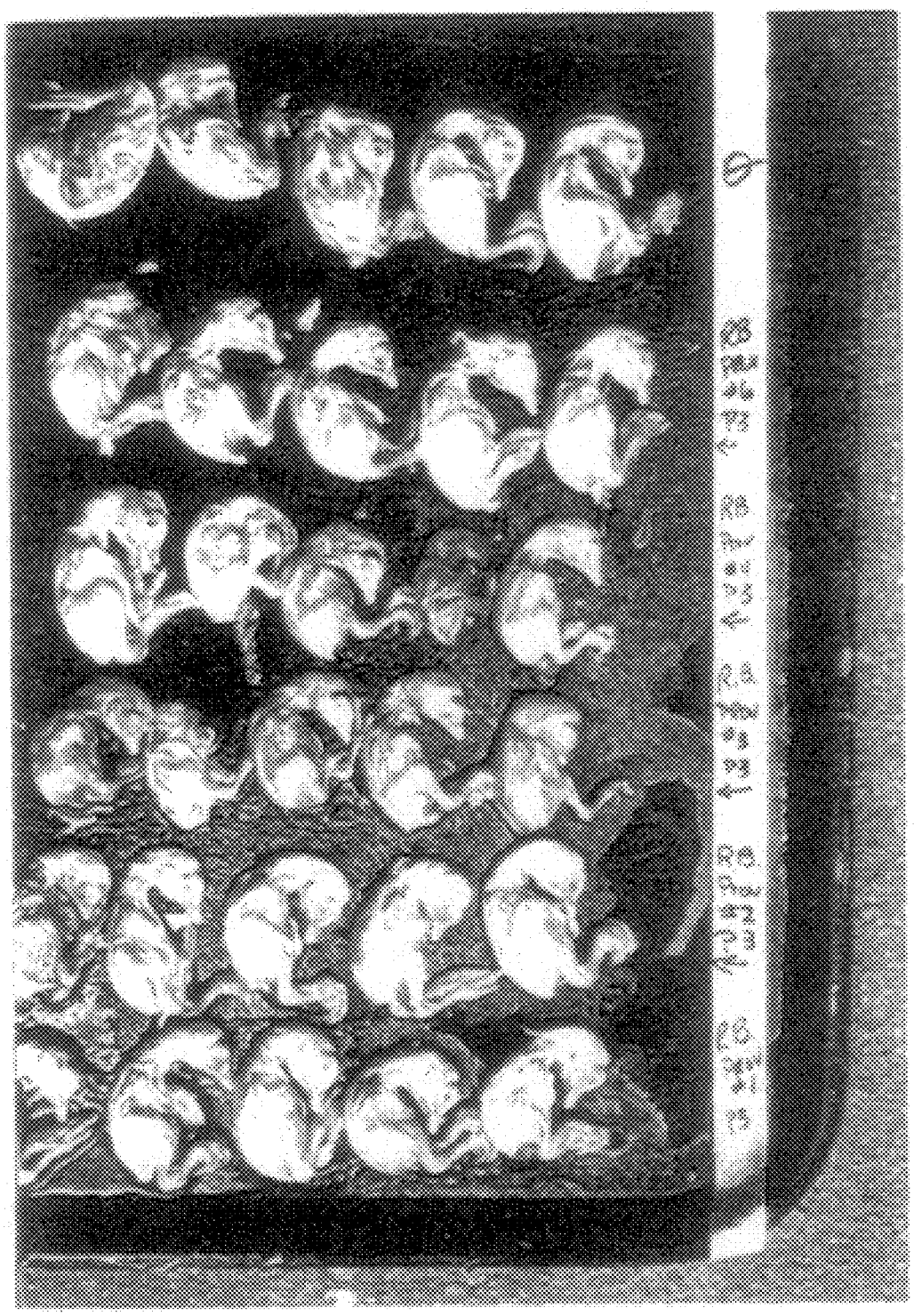
FIG. 32 shows a demonstration of lesions produced following immunoprecipitation of AC-ELISA positive proventriculi after three consecutive passages in SPF eggs.

Immunoprecipitation of IBDV antigen from AC-ELISA positive tissue homogenates is quite easy to perform. This procedure represents a rapid method for separating and concentrating IBDV from field samples that could potentially contain many virus types. The uniqueness of the binding of the IBDV Mab B29 without neutralization of virus infectivity makes this particular procedure adaptable to a any number of assay systems, and as we have demonstrated here works quite well for virus isolation in eggs (FIG. 32).

Proventricular origin IBDV suspect isolates demonstrated repeated characteristics of bursal lesion production, antibody stimulation, and AC-ELISA analysis which indicate that they are indeed IBDV. These particular isolates are capable of producing lesions in the proventriculus but do not appear to be significantly more pathogenic than the USDA/STC IBDV isolate for the proventriculus. There are two considerations at this point: field isolates may have a lower affinity for infecting the proventriculus, or there may be differences in virus inoculum titer (Table 36).

The new isolates appear to share characteristics of both the Delaware variant and a more recent California IBDV isolate from the bursa. RT/PCR characterization of two isolates indicate that they may represent a unique group of IBD viruses.

The viral isolates Texas RB 3, Texas RB 4, HBS, F57–7, W/L 39, GAR 1, and/or others are deposited with the American Type Culture Collection (ATCC) patent depository, 10801 University Blvd., Manasses, Va. 20110–2209, Telephone 703 365–2700 on behalf of the University of Arkansas, Arkansas, U.S.A. and have respective deposit accession numbers.

FURTHER DISCUSSION

It was a goal of this invention that the data compiled provide significant inroads toward solving what appears to be a very widely distributed poultry industry problem involving proventriculitis syndrome. It is also necessary at this point to recognize that although this data establishes the ability of infectious bursal disease virus infection to induce lesions in other lymphoid areas in the chicken, it does not establish that all proventriculitis occurs as a result of infectious bursal disease virus infection. However, at this point it appears safe to say that infectious bursal disease virus represents a significant portion of the problem identified as proventriculitis.

In consideration of the information provided in this patent application, the poultry industry might wish to review current vaccination protocols concerning infectious bursal disease virus prevention and control. An additional emphasis should also be applied to the consideration of infectious bursal disease virus and the role it plays as an enteric pathogen. If poultry industry dogma continues to consider only the immunosuppressive nature of infectious bursal disease virus infection, then it will continue to do battle with a virus it does not understand.

Infectious bursal disease virus has historically demonstrated the ability to adapt and escape whatever control measures the industry has managed to put in place. Of course the possibility exists that infectious bursal disease virus infection of the proventriculus has been simply overlooked all this time. But the sudden onset of widespread proventriculitis in multiple geographical areas might also suggest that these new IBDV isolates are simply the latest adaptation of an extremely hard to control virus.

Future considerations in the control of infectious bursal disease virus should encompass and consider infectious bursal disease as an enteric pathogen. The eventual goal of this work and the work of a number of individuals to follow is the reduction in the incidence of proventriculitis and the possibility of an improved feed conversion, with a new generation of vaccines derived from infectious bursal disease virus isolates of enteric origin.

The present invention is directed to at least poultry virus isolates Texas RB 3, Texas RB 4, HBS, F57-1, W/l 39, and GAR 1 and the use of these virus isolates as or in vaccines for proventriculitis.

Numerous experiments were conducted to determine the role of infectious bursal disease (IBD) virus in the induction of lesions associated with proventriculitis syndrome in chickens. Parameters examined included age of the chicken at IBD virus exposure, concentration of IBD virus at exposure, the strain of IBD virus, dietary influence in the presence of IBD virus, mixed IBD virus infection, autoimmune mediated IBD reactions associated with lesion production, viral induced apoptotic tissue injury and isolation and characterization of the causative agent.

The experiments were carried out in SPF white leghorns, with the experimental birds being examined for the presence of gross and microscopic lesion at 4 and 11 days post challenge. Tissue homogenates were analyzed for the presence of IBDV at 4 and 11 days post challenge with Antigen Capture ELISA (AC-ELISA). Determinations of neutralizing antibody levels and IgG antibody responses were monitored as well as depletion of serum complement following IBDV infection. Physical parameters were also considered utilizing body weights and organ to body weight ratios to determine IBDV effects following experimental challenge.

Physical parameters indicated that the primary viral response is predominantly in the bursa of Fabricius, but changes were also noted in the proventriculus. Physical changes in the proventriculus occurred primarily during the acute stage of the IBD virus infection.

REFERENCES

1. Allan, W., J. Faragher, G. Cullen, (1972). Immunosuppression by the infectious bursal agent in chickens immunized against Newcastle disease. Vet. Rec. 90:511–512.
2. Avakian, A., C. Whitfill, E. Haddad, C. Ricks, K. Skeeles, P. Andrews, and J. Thoma, (1993). Efficacy of a novel infectious bursal disease (IBD) vaccine administered in-ovo to broiler chickens. Poultry Sci. 72 (Suppl.1):49.
3. Azad, A., M. Jagadish, M. Brown, and P.Hudson, (1987). Deletion mapping and expression in *Escherichia coli* of the large genomic segment of a Birnavirus. Virology 161:145–152.

4. Bayliss, C., U. Spies, K. Shaw, R. Peters, A. Papageorgiou, H. Müller, and M. Boursnell, (1990). A comparison of the sequences of segment A of four infectious bursal disease virus strains and identification of a variable region in VP2. J. Gen. Virol. 71:1303–1312.
5. Bayyari, G., W. Huff, J. Beasley, J. Balog, and N. Rath, (1996). The effect of dietary copper sulfate on infectious proventriculitis. Poult. Sci. 75:1961–1969.
6. Bayyari, G. J. Skeeles. J. Story, and M. Slavik, (1991). Determination of infectious bursal disease virus titration and neutralization endpoints using fluorogenic staining. Avian Dis. 35:476–480.
7. Bayyari, G., J. Story, J. Beasley, and J. Skeeles (1996). Pathogenicity studies of an Arkansas variant infectious bursal disease virus. Avian Dis. 40:516–532.
8. Bayyari, G., J. Story, J. Beasley, and J. Skeeles (1996). Antigenic characterization of an Arkansas isolate of infectious bursal disease virus. Avian Dis. 40:588–599.
9. Bayyari, G., W. Huff, J. Balog, N. Rath, and J. Beasley (1995). Experimental reproduction of proventriculitis using homogenates of proventricular tissue. Poult. Sci. 74:1799–1809.
10. Becht, H., (1980). Infectious bursal disease virus. Curr. Top. Micro. Immuno. 90:107–121.
11. Becht, H., H. Müller, and H. K. Müller, (1988). Comparative studies on structural and antigenic properties of two serotypes of infectious bursal disease virus. J. Gen. virology 69:631–640.
12. Ben-Sasson, S. A., Y. Sherman, and Y. Gavrieli, (1995). Identification of Dying Cell-In Sitit Staining. Chapter 2, Methods in Cell Biology Vol. 46. Academic Press Inc., San Diego, CA. pp 29–39.
13. Benton, W., M. Cover, J. Rosenberger, and R. Lake, (1967). Physiochemical properties of the infectious bursal agent (IBA). Avian Dis. 11:438–445.
14. Bernard, J., (1980). Drosophila X virus RNA polymerase: tentative model for in-vitro replication of the double stranded virion RNA. J. Virol. 33:717–723.
15. Brown, M. , Green P., and M. Skinner, (1984). Sequence analysis of a very virulent UK isolate of infectious bursal disease. Proceedings of the Intl. Symposium on Infectious Bursal Disease and Chicken Infectious Anaemia, Rauischholzhausen, Germany, June 21–24.
16. Burkhardt, E., and H. Müller, (1987). Susceptibility of chicken blood lymphoblasts and monocytes to infectious bursal disease virus (IBDV). Arch. Virol. 94:297–303.
17. Cheville, N. F. (1994). In: Ultrastructural Pathology, An Introduction To Interpretation. Chapters 3–4 pp.476–478, 566. Iowa State University Press, Ames Iowa.
18. Cheville, N. F. (1967). Studies on the pathogenesis of Gumboro disease in bursa of Fabricius, spleen and thymus of chickens. Am. J. Path. 51: 527–551.
19. Cho, B., R. Raymond, and R. Hill, (1979). Growth of infectious bursal disease virus with plaque formation in chick embryo fibroblast cell culture. Avian Dis. 24:423–434.
20. Cho, Y. and S. Edgar (1972). Characterization of infectious bursal disease. Poult. Sci. 51:60–69.
21. Cosgrove, A. S. (1962). An apparently new disease of chickens—Avian nephrosis. Avian Dis. 6:385–389.
22. Craft, D., J. Brown, P. Lukert, (1990). Effects of standard and variant strains of infectious bursal disease virus on infections of chickens. Am. J.Vet. Res. 51:1192–1197.
23. Cummings, T., C. Broussard, R. Page, S. Thayer, and P. Lukert, (1986). Infectious bursal disease virus in turkeys. Vet. Bull. 56:757–761.
24. Cursiefen, D., I. Kaufer, and H. Becht, (1979). Loss of virulence in a small plaque mutant of the infectious bursal disease virus. Arch. Virol. 59:39–46.
25. Davis V., and J. Boyle, (1990). Random cDNA probes to infectious bursal disease virus. Avian Dis. 34:329–335.
26. Dobos, P., (1979). Peptide map comparison of the proteins of infectious bursal disease virus. J. Virol. 32:1047–1050.
27. Dobos, P., B. Hill, R. Hallett, D. Kells, H. Becht, and D. Teninges, (1979). Biophysical and biochemical characterization of five animal viruses with bisegmented double stranded RNA genomes. J. Virol. 32(2):593–605.
28. Dohms, J., K. Lee, and J. Rosenberger, (1981). Plasma cell changes in the gland of harder following infectious bursal disease virus infection of the chicken. Avian Dis. 25:683–695.
29. Ezeokoli, C., E. Ityondo, A. Nwannenna, and J.Umoh, (1990). Immuno-suppression and histopathological changes in the Bursa of Fabricius associated with infectious bursal disease vaccination in chicken. Comp. Immun. Microbiol. Infect. Dis. Vol 13:181–188.
30. Fadly, A. and K. Nazerian, (1983). Pathogenesis of infectious bursal disease in chickens infected with virus at various ages. Avian Dis. 27(3): 714–723.
31. Fahey, K., I. O'Donnell, and T. Bagust, (1985). Antibody to the 32K structural protein of infectious bursal disease virus neutralizes viral infectivity in vitro and confers protection on young chickens. Virology 66:2693–2702.
32. Fahey, K., K. Erny and J. Crooks, (1989).A conformational immunogen on VP-2 of infectious bursal disease virus that induces virus-neutralizing antibodies that passively protect chickens. Virology 70:1473–1481.
33. Fahey, K., P. McWaters, M. Brown, K. Erny, V. Murphy, and D. Hewish. (1991). Virus-neutralizing and passively protective monoclonal antibodies to infectious bursal disease virus of chickens. Avian Dis. 35:365–373.
34. Faragher, J., W. Allan, P. Wyeth, (1974). Immunosuppressive effect of infectious bursal agent on vaccination against Newcastle disease. Vet. Rec. 95:385–388.
35. Gelb, J., C. Eidson, O. Fletcher, and S. Kleven, (1979). Studies on interferon induction by infectious bursal disease virus (IBDV). II. Interferon production in White Leghorn chickens infected with an attenuated or pathogenic isolate of IBDV. Avian Dis. 23:634–645.
36. Giambrone, J. and R. Clay (1986). Evaluation of the immunogenicity, stability. pathogenicity and immunodepression of four commercial live infectious bursal disease vaccines. Poult. Sci. 65:1287–1290.
37. Glick, B., T. Chang, and R. Japp (1956). The bursa of Fabricius and antibody production. Poult. Sci. 35:224–226.
38. Goodwin, M., S. Hafner, D. Bounous, K. Latimer, E. Player, F. Niagro, R.
Campagnoli, J. Brown, (1996). Viral proventriculitis in chickens. Avian Path. 25:369–379.
39. Haddad, E., C. Whitfill, C. Ricks, A. Avakian, K. Skeeles, P. Andrews, and J. Thoma. (1993). Efficacy of a novel infectious bursal disease (IBD) vaccine administered in-ovo to SPF chickens. Poultry Sci. 72 (Suppl 1): 49.
40. Harkness, J., D. Alexander, M. Pattison, and A. Scott (1975). Infectious bursal disease agent, morphology by negative stain electron microscopy. Arch. Virol. 48:63–73.
41. Harris, T. J. R., F. Brown, and D. V. Sangar, (1981). Differential precipitation of foot and mouth disease virus proteins made in vivo and in vitro by hyperimmune and virus particle guinea pig antiserum. Virology, 112:91–98.

42. Hassan, M. and Y. Saif (1996). Influence of the host system on the pathogenicity, immunogenicity, and antigenicity of infectious bursal disease virus. Avian Dis. 553–561.
43. Hassan, M., Y. Saif, and S. Shaky, (1996). Comparison between antigen—capture ELISA and conventional methods used for titration of infectious bursal disease virus. Avian Dis. 40:562–566.
44. Hassan, M., M. Natour, L. Ward, and Y. Saif (1996). Pathogenicity, attenuation, and immunogenicity of infectious bursal disease virus. Avian Dis. 40:567–571.
45. Hebert, C. N., N. E. Reed, J. C. Muskett and D. H. Thorton (1982). Factors affecting the reproducibility of the serum neutralization test for infectious bursal disease. J. of Biological Standardization 10:221–229.
46. Heine, H., M. Haritow, P. Failla, K. Fahey, and A. Azad (1991). Sequence analysis and expression of the host-protective immunogen VP2 of a variant strain of infectious bursal disease virus which can circumvent vaccination with standard type I strains. J. Gen Virol. 72:1835–1843.
47. Helmbolt, C. and E. Garner (1964). Experimentally induced Gumboro disease (IBA). Avian Dis. 8:561–575.
48. Henderson, K., and D. J. Jackwood, (1990). Comparison of the dot blot hybridization assay with antigen detection assays for the diagnosis of infectious bursal disease virus infections. Avian Dis. 34:744–748.
49. Hinshaw, V. S., C. W. Olsen, N. Dybdahl-Sissoko and D. Evans, (1994). Apoptosis:a Mechanism of Cell Killing by Influenza A and B Viruses. J. Virol. 68(6):3667–3673.
50. Hirai, K., and B. Calnek (1979). In vitro replication of infectious bursal disease virus in established lymphoid cell line and chicken B lymphocytes. Infect. Immun. 25:964–970.
51. Hirai, K., and S. Shimakura, (1974). Structure of infectious bursal disease virus. J. Virol. 14:957–964.
52. Hirai, K., S. Shimakura, and E. Kawamoto (1974). Electron-microscope characterization of infectious bursal disease virus. Avian Dis. 18:467–471.
53. Hirai, K., S. Shimakura, E. Kawamoto, F. Taguchi, S. T. Kim, C. N. Chang, and Y. Iritani (1974). The immunodepressive effect of infectious bursal disease virus in chickens. Avian Dis. 18:50–57.
54. Hitchner, S. B. (1971). Persistence of parental infectious bursal disease antibody and its effects on susceptibility of young chickens. Avian Dis 15:894–900.
55. Humason, G. L. (1972). In: Animal Tissue Techniques. 3rd Edition. W.H. Freeman and Company, San Franscisco. pp 37–156.
56. Ismail, N., A. Fadly, and T. Chang, (1987). Effect of bursal cell number on the pathogenesis of infectious bursal disease in chickens. Avian Dis. 31: 546–555.
57. Ismail, N. and Y. Saif, (1991). Immunogenicity of infectious bursal disease viruses in chickens. Avian Dis. 35:460–469.
58. Ivanyi, J., and R. Morris, (1976). Immunodefficiency in the chicken IV. An immunological study of infectious bursal disease. Clin. Exp. Immunol. 23:154–165.
59. Jackwood, D. H., and Y. Saif, (1987). Antigenmc diversity of infectious bursal disease viruses. Avian Dis. 31:766–770.
60. Jackwood, D. H., G. Hanes, and S. Heins Miller, (1996). Infectious bursal disease viral RNA amplification using RT/PCR from bursa tissue following phenol:chloroform inactivation of the virus. Avian Dis 40:457–460.
61. Jackwood, D. H., Y. Saif, and J. Hughes, (1987). Replication of infectious bursal disease virus in continuous cell lines. Avian Dis. 31:370–375.
62. Jackwood, D. J., F. Kibenge, and C. Mercado, (1990). The use of biotin-labeled cDNA probes for the detection of infectious bursal disease viruses. Avian Dis. 34:129–136.
63. Jackwood, D. J., F. Kibenge, and C. Mercado, (1989). Detection of infectious bursal disease viruses by using cloned cDNA probes. J. Clin.Micro. 27:.2437–2443.
64. Jackwood, D. J., Y. Saif, and J. Hughes, (1984). Nucleic acid and structural proteins of infectious bursal disease virus isolates belonging to serotypes I and II. Avian Dis. 28:990–1006.
65. Jackwood, D. J., Y. Saif, and J. Hughes, (1982). Characteristics and serologic studies of two serotypes of infectious bursal disease virus in turkeys. Avian Dis. 26:871–882.
66. Jagadish, M., and A. Azad, (1991). Localization of a VP3 epitope of infectious bursal disease virus. Virology. 184:805–807.
67. Jagadish, M., P. Vaughan, R. Irving, A. Azad, and I. Macreadie, (1990). Expression and characterization of infectious bursal disease virus polyprotein in yeast. Gene. 95:179–186.
68. Jagadish, M., V. Staton. P. Hudson, and A. Azad, (1988). Birnavirus precursor polyprotein is processed in *Escherichia coli* by its own virus-encoded polypeptide. J.Virol. 62(3): 1084–1087.
69. Jeurissen, S., L. Vervelde, and E. Janse, (1994). Structure and function of lymphoid tissue of the chicken. Poultry Sci. Rev. 5:183–207.
70. Jeurissen, S. H., F. Wagenaar, J. M. Pol, A. J. vander Eb, M. H. Noteborn, (1992). Chicken anemia virus causes apoptosis of thymocytes after in-vivo infection and of cell lines after in vitro infection J. Virol 66(12):7383–7388.
71. Jönsson, L. and B. Engstrom (1986). Immunohistochemical detection of infectious bursal disease and infectious bronchitis antigens in paraffin embedded chicken tissue Avian Path. 15:385–393.
72. Kaüfer, I and E. Weiss, (1980). Significance of bursa of Fabricius as target organ in infectious bursal disease of chickens. Infect. Immun. 27:364–367.
73. Kaüfer, I. and E. Weiss, (1976). Electron-microscope studies on the pathogenesis of infectious bursal disease after intrabursal application of the causal virus. Avian Dis. 29: 483–495.
74. Karnovsky, M. J., (1965). A formaldehyde-glutaraldehyde fixative of high osmolarity for use in electron microscopy. J. Cell. Biol. 27:137A.
75. Kessler, S. W., (1975). Rapid isolation of antigens from cells with a staphylococcal protein A-antibody adsorbent: Parameters of the interaction of antibody-antigen complexes with protein A. J. of Immunology 115(6):1617–1624.
76. Kiberge, F., A. Dhillon, and R. Russell, (1988). Biochemistry and immunology of infectious bursal disease virus. J. Gen. Virology 69:1757–1775.
77. Kiberge, F., D. Jackwood, and C. Mercado, (1990). Nucleotide sequence analysis of genome segment A of infectious bursal disease virus. J. Gen. Virology 71:569–577.
78. Komine, K. , H. Ohta, S. Kamata, K. Uchida, and K. Hirai, (1989). Infectivity of infectious bursal disease virus neutralized by maternal antibody in various chicken cells. Jpn. J. Vet. Sci. 51:634–635.
79. Komine K., H. Ohta, S. Kamata, K. Uchida, Y. Yoshikawa, K. Yamanouchi. and H. Okada, (1989). Complement activation by infectious bursal disease virus and its relevance to virus growth in the lymphoid cells. Jpn. J. Vet. Sci. 51:1259–1262.

80. Lam, K. M., (1991). Infectious bursal disease virus type 1-induced suppression of chicken lymphocyte response to mitogen. Avian Path. 20:205–212.
81. Lange, H., H. Müller, I. Kaüller, and H. Becht, (1987). Pathogenic and structural properties of wild type infectious bursal disease virus (IBDV) and virus grown in vitro. Arch. of Virol. 92:187–196.
82. Ley, D. H., R. Yamamoto, and A. A. Bickford, (1979). Immune complex involvement in the pathogenesis of infectious bursal disease virus in chickens. Avian Dis. 23: 219–224.
83. Lukert, P. and R. Davis, (1974). Infectious bursal disease virus: growth and characterization in cell cultures. Avian Dis. 18:243–250.
84. Lukert P. and Y. Saif, (1991). Infectious bursal disease. In: Diseases of Poultry, edited by B. W. Calnek, H. J. Barnes, C. W. Beard, W. M. Reid. H. W. Yoder Jr., 9th edit. Iowa State University Press, Ames, Iowa pp.648–663.
85. Lukert, P., J. Leonard, and R. Davis, (1975). Infectious bursal disease virus: antigen production and immunity Am. J. Vet. Res. 36:539–540.
86. Lunger, P. and T. Maddux, (1972). Fine structure studies of the avian infectious bursal agent. I. In vivo viral morphogenesis. Avian Dis. 16:874–893.
87. Mackenzie, M. and P. Spradbrow, (1981). Persistence of infectious bursal disease virus in experimentally infected chickens. Aust. Vet. Journal no. 57.
88. Macreadie, A., P. Vaughan, A. Chapman, N. McKern, M. Jagadish, H. Heine, C.Ward, K. Fahey, and A. Azad, (1990). Passive protection against infectious bursal disease virus by viral VP2 expressed in yeast. Vaccine 8:549–552.
89. Masegi, H. Fukushi, K. Hirai (1996). In-vitro attenuation of highly virulent infectious bursal disease virus: Some characteristics of attenuated strains. Avian Dis. 40:501–509.
90. McFerran, J., M. McNulty, E. McKillop, T. Connor, R. McCracken, D. Collins, and G. Allan (1980). Isolation and serological studies with infectious bursal disease viruses from fowl, turkeys and ducks: Demonstration of a second serotype. Avian Path. 9:395–404.
91. McNulty, M., G. Allan, and J. McFerran (1979). Isolation of infectious bursal disease virus form turkeys. Avian Path. 8:205–212.
92. Mitra, G. , 1995. Apoptosis: Detection of Apoptotic Cells. Promega Notes vol. 57. Promega Inc., Madison Wiss., pp. 10–15.
93. Morgan, M., I. Macreadie, V. Harley, P. Hudson, and A. Azad, (1988). Sequence of the small double stranded RNA genomic segment of infectious bursal disease virus and its deduced 90 kDa product. Virology 163:240–242.
94. Müller, H., (1986). Replication or infectious bursal disease virus in lymphoid cells. Arch. Virol. 87:191–203.
95. Müller, H. and H. Becht, (1982). Biosynthesis of virus-specific proteins in cells infected with infectious bursal disease virus and their significance as structural elements for infectious virus and incomplete particles. J. Virol. 44:384–392.
96. Müller, H., and R. Nitschke, (1987). Molecular weight determination of the two segments of double stranded RNA of infectious bursal disease virus, a member of the birnavirus group. Med. Microbiol Immunol 176:113–121.
97. Müller, H., and R. Nitschke, (1987). The two segments of the infectious bursal disease virus genome are circularized by a 90,000-kDa protein. Virology. 159:174–177.
98. Müller, H., C. Scholtissek, and H. Becht, (1979). The genome of infectious bursal disease virus consists of two segments of double-stranded RNA. J.Virol. 31(3): 584–589.
99. Müller, H., H. Lange, and H. Becht, (1986). Formation, characterization and interfering capacity of a small plaque mutant and of incomplete virus particles of infectious bursal disease virus. Virus Research 4:297–309.
100. Nagabashi, T., H. Izawa, and M. Soekawa (1973). Infectious bursal disease viral particles revealed in avian cell culture by electron microscope. Arch. of Exp. Med. Vol 46(3–4): 135–137.
101. Nakai, T., and K. Hirai, (1981). In-vitro infection of fractionated chicken lymphocytes by infectious bursal disease virus. Avian Dis. 25:831–838.
102. Nakamura, T., S. Hoshi, Y. Nagasawa, S. Ueda, (1995). The effect of route of inoculation on protection by killed vaccines in chickens. Avian Dis. 39:507–513.
103. Naqi, S. and D. Millar, (1979). Morphologic changes in the bursa of Fabricius of chickens after inoculation with infectious bursal disease virus. Am. J. Vet Res., Vol 40(8): 1134–1139.
104. Nick, H. Curisiefen, D., and H. Becht (1976). Structural and growth characteristics of infectious bursal disease virus. J. Virol. 18:227–234.
105. Okoye, J. O. A. (1984). Infectious bursal disease of chickens. Vet. Bulletin 54(6):425–436.
106. Okoye, J. and M.Uzoukwu, (1990). Pathogenesis of infectious bursal disease in embryonally bursectomised chickens. Avian Path. J.W.V.P.A. 19:555–569.
107. Olah, I., and B. Glick, (1992). Follicle-associated epithelium and medullary epithelial tissue of the bursa of Fabricius are two different compartments. Anat. Rec. 233:577.
108. Oppling, V., H. Müller, H. Becht, (1991). Heterogeneity of antigenic sites responsible for the induction of neutralizing antibodies in infectious bursal disease virus. Arch. Virol. 1191:211–273.
109. Oppling, V., H. Müller, H. Becht, (1991). The structural polypeptide VP3 of infectious bursal disease virus carries group and serotype specific epitopes. J. Gen. Virol. 72:2275–2278.
110. Otaki, Y., T. Nunoya, H. Tajima, K. Saito, T. Nomura. (1989). Enhanced pathogenicity of chick anemia agent by infectious bursal disease virus relating to the occurrence of Mareks's disease vaccination breaks. Jpn. J. Vet. Sci. 51(4):849–852.
111. Ozel, M. and H. Gelderbloom, (1985). Capsid symmetry of viruses of the proposed Birnavirus group. Arch. of Virol. 84:149–161.
112. Panigraphy, B., L. Misra, and L. Adams, (1982). Humoral and cell-mediated immune response in chickens with infectious bursal disease. Vet. Micro. 7:383–387.
113. Persson, R. and R. MacDonald (1982). Evidence that infectious pancreatic necrosis virus has a genome linked protein. J. Virol. 44:437–443.
114. Petek, M., P. D'Aprile, and F. Cancelloti, (1973). Biological and physiochemical properties of infectious bursal disease virus (IBDV). Avian Path. 2:135–152.
115. Pope, C. R. (1996). Lymphoid system. In: Avian Histopathology. C. Riddell ed. American Association of Avian Pathologists, Kennett Square, Pa. p.17–44.
116. Randall, C. J. and R. L. Reece,eds. (1996). Lymphoid and Hematopoietic System. In: Color Atlas of Avian Histopathology. Mosby-Wolfe, Milan Italy. p.101–124.
117. Rosales, A., P. Villegas,. P. Lukert, O. Fletcher M. Mohamed, and J. Brown (1989). Isolation, identification, and pathogenicity of two field strains of infectious bursal disease virus. Avian Dis. 33:35–41.
118. Rosales, A., P. Villegas, P. Lukert, O. Fletcher, M. Mohamed, and J. Brown, (1989). Pathogenicity of recent solates of infectious bursal disease virus in specific-pathogen-free chickens: Protection conferred by an intermediate vaccine strain. Avian Dis. 33:729–734.
119. Rosenberger J. K. (1989). Infectious bursal disease. In: A laboratory manual for the isolation and identification of avian pathogens, 3rd ed. H. G. Purchase, L. H. Arp, C. H. Domermuth, and J. E. Pearson, ed. American Association of Avian Pathologists, Kennett Square, Pa. pp.165–166.
120. Rosenberger, J. and S. Cloud (1986). Isolation and characterization of variant infectious bursal disease viruses. Proceedings of the 123rd Annual Meeting of the A.V. M. A. abstract 181.
121. Rosenberger, J. and J. Gelb Jr. (1978). Response to several avian respiratory viruses as affected by infectious bursal disease virus. Avian Dis. 22:95–105.
122. Saif, Y. M., (1984). Infectious bursal disease virus type. Proceedings of the 19th National Meeting on Poultry Health and Condemnations, 105–107.
123. Salio, K., M. Higashihara, Y. Fujisaki, and M. Matumoto, (1990). Isolation and characterization of attenuated plaque variants of infectious bursal disease virus.
Vet. Micro. 22:171–178.
124. SAS Institute Inc., SAS/STAT® User's Guide, Version 6, Fourth Edition, Volume 2, Cary NC: SAS Institute Inc., 1989. 846pp.
125. Schat, K., Lucio, B. and J. Carlisle (1981). Pathogenesis of infectious bursal disease virus in embryonally bursectomized chickens. Avian Dis. 25:996–1004.
126. Sharma, J. M. (1988). Presence of natural suppressor cells in the chicken embryo spleen and the effect of virus infection of the embryo on suppressor cell activity. Vet. Immuno. Immunopath. 19:51–66.
127. Sharma, J. M. ( 1986). Embryo vaccination of specific pathogen free chickens with infectious bursal disease virus: Tissue distribution of the vaccine virus and protection of hatched chickens against disease Avian Dis. 30(4): 776–780.
128. Sharma, J., and L. Lee, (1983). Effect of infectious bursal disease on natural killer cell activity and mitogenic response of chicken lymphoid cells: Role of adherent cells in cellular immune suppression. Infection and Immunity, :747–754.
129. Sharma, J., J. Dohms, and A. Metz, (1989). Comparative pathogenesis of serotype 1 and variant serotype 1 isolates of infectious bursal disease virus and their effect on humoral and cellular immune competence of specific pathogen free chickens. Avian Dis. 33:112–124.
130. Sharma, J., J. Dupuy, and L. Lamontagne, (1988). In:Virus-Induced Immunosuppression, S. Specter, M. Bendinelli, and H. Friedman, Eds. ( Plenum Press, New York and London), pp. 201–216.
131. Sharma, J. M. and J. K. Rosenberger, (1987). Infectious bursal disease and reovirus infection of chickens: Immune responses and vaccine control. In: Avian Immunology: Basis and Practice vol II. . A. Toivanen, and P. Toivanen, Eds. (CRC Press Inc. Boca Raton, Fla.)
132. Sivanandan, V. and S. Maheswaran, (1980). Immune profile of infectious bursal disease. III. Effect of infectious bursal disease virus on the lymphocyte responses to phytomitogens and on mixed lymphocyte reaction of chickens. Avian Dis. 25(1): 112–120.
133. Skeeles, J., M. Slavik, J. Beasley, A. Brown, C. Meinecke, S. Maruca, and S. Welch, (1980). An age-related coagulation disorder associated with experimental infection with infectious bursal disease virus. Am. J. Vet. Res. 41:1458–1461.
134. Skeeles, J., P. Lukert, E. De-Buysscher, O. Fletcher, and J. Brown, (1979). Infectious bursal disease viral infections. I. Complement and virus -neutralizing antibody response following infection of susceptible chickens. Avian Dis. 23:95–106.
135. Skeeles, J., P. Lukert, E. DeBuysscher, O. Fletcher, and J. Brown, (1979). Infectious bursal disease viral infections. II. The relationship of age, complement levels, virus-neutralizing antibody, clotting, and lesions. Avian Dis. 23: 107–117.
136. Skeeles, J. , P. Lukert, and E. DeBuysscher, (1979). Hemolytic complement in specific pathogen free chickens: Influence of age and sex. Avian Dis. 23: 225–228.
137. Skeeles, J., P. Lukert, O. Fletcher, and J. Leonard, (1979). Immunization studies with a cell-culture adapted infectious bursal disease virus. Avian Dis. 23:456–465.
138. Snyder, D., D. Lana, B. Cho, and W. Marquandt, (1988). Group and strain specific neutralization sites of infectious bursal disease virus defined with monoclonal antibodies. Avian Dis. 32:527–534.
139. Snyder, D., D. Lutticken, P. Savage, F. Yancy, P. Marel, S. Mengei, E. Russek-Cohen, and W. Marquandt (1988). Differentiation of infectious bursal disease viruses directly from infected tissues. Isolation and geographical distribution of a novel antigenic variant of infectious bursal disease virus. Avian Dis. 32:535–539.
140. Solano, W., J. Giambrone, and V. Panagala (1986). Comparison of a kinetic based enzyme linked immunosorbent assay (KELISA) and virus neutralization test for infectious bursal disease virus II. Decay of maternal antibody in progeny from white leghorns receiving various vaccination regimens. Avian Dis. 30(1):126–131.
141. Spies, U., and H. Müller, (1990). Demonstration of enzyme activities required for cap structure formation in infectious bursal disease virus, a member of the birnavirus group. J. Gen. Virol. 71:977–981.
142. Spies, U., H. Müller, and H. Becht, (1987). Properties of RNA polymerase activity associated with infectious bursal disease virus and characterization of its reaction products. Virus Res. 8:127–140.
143. Spurr, A. R., 1969. A low-viscosity epoxy resin embedding medium for electron microscopy. J. Ultrastruct. Res. 26:31–43.
144. Tanimura, N., K. Tsukamoto, K. Nakamura, M. Narita, M. Maeda, (1995). Association between pathogenicity of infectious bursal disease virus and virus antigen distribution detected by immunohistochemistry. Avian Dis. 39:9–20.
145. Tham, K. and C. Moon, (1996). Apoptosis in cell cultures induced by infectious bursal disease virus following in vitro infection. Avian Dis. 40:109–113.
146. Tsukamoto, K., N. Tanimura, M. Mase and K. Imar (1995). Comparison of virus replication efficiency in lymphoid tissues among three infectious bursal disease virus strains. Avian Dis. 39:844–852.
147. Van Den Berg, T., and G. Meulemans, (1991). Acute infectious bursal disease in poultry: protection afforded by maternally derived antibodies and interference with live vaccination. Avian Pathol. J.W.V.P.A. 20:409–421.

148. Vasconcelos, A. and K. Lam, (1995). Apoptosis in chicken embryos induced by the infectious bursal disease virus. J. Comp. Path. 112:327–338.
149. Vasconcelos, A. and K. Lam, (1994). Apoptosis induced by infectious bursal disease virus. J. Gen. Virol. 75: 1803–1806.
150. Weiss E. and I. Kaufer-Weiss, (1994). Pathology and pathogenesis of infectious bursal disease. Proceedings Intl. Symposium on Infectious Bursal Disease and Chicken Infectious Anaemia. Rauischholzhausen, Germany, Jun. 21–24.
151. White, E. (1996). Pathways for regulation of apoptosis: Overview of apoptosis. In: Oncogene Research Products Scientific Reference Guide. Calbiochem™. p. 9–15.
152. Wideman, R. F, Y. Kochera Kirby, T. L. Barton, D. Clark, G. R. Bayyari, W. E. Huff, P. A. Moore, and P. A. Dunn (1996). Excess dietary copper triggers enlargement of the proventriculus in broilers. J. Appl. Poultry Res.5:219–230.
153. Winterfield, R. W. and H. L. Thacker, (1978). Immune response and pathogenicity of different strains of infectious bursal disease virus applied as vaccines. Avian Dis. 22:721–731.
154. Wu, C., T. L. Lin, H. G. Zhang, V. S. Davis, and J. A. Boyle, (1992). Molecular detection of infectious bursal disease virus by polymerase chain reaction. Avian Dis. 36:221–226.
155. Yamaguichi, T., T. Kondo, Y. Inoshima, M. Ogawa, M. Miyoshi, T. Yanai, T. Maseg,i, H. Fukushi, K. Hirai (1996). In-vitro attenuation of highly virulent infectious bursal disease virus: Some characteristics of attenuated strains. Avian Dis. 40501–590.
156. Newberry, L. A. Doctoral Dissertation: Determination of the role of standard and variant strains of infectious bursal disease virus in the induction of viral proventriculitis and enteric disease in chickens. University of Arkansas, Fayetteville, AR, December 1996.
157. Villines, J. 1995. The evaluation of eleven isolates of avian reovirus to induce proventriculitis in chickens. M. S. Thesis. University of Arkansas, Fayetteville.
158. Wilson, M A., L. A. Newberry, J. K. Skeeles, G. R. Bayyari, W. E. Huff, N. N. Beasley, R. W. McNew, F. D. Clark, C. A. Whitfill and E. E. Haddad. A study of prventriculitis, its association with infectious bursal disease virus and the efficacy of commercial IBDV vaccines in prevention. Proceedings of the 46th North Central Conference of Avian Diseases and Symposium on New Vaccines and Delivery Systems. Sep. 17–19 1995. Bloomington, Minn. p. 121.

TABLE 1

Antigen Capture ELISA analysis of proventriculi tissue pools collected at 4 and 11 days post challenge with Variant E/1084 IBDV given at 7, 14, 21 and 28 days post hatch and after challenge with USDA/STC IBDV at 28 days post hatch only.

| Age at Challenge | 4 Days Post Challenge | 11 Days Post Challenge |
| --- | --- | --- |
| Day 7 Variant E/1084 | − | − |
| Day 7 Negative Control | − | − |
| Day 14 Variant E/1084 | +/− | − |
| Day 14 Negative Control | − | − |
| Day 21 Variant E/1084 | − | − |
| Day 21 Negative Control | − | − |
| Day 28 Variant E/1084 | + | − |
| Day 28 USDA/STC | + | − |
| Day 28 Negative Control | − | − |

TABLE 2

Antigen Capture ELISA analysis of bursal tissue pools collected at 4 and 11 days post challenge with Variant E/1084 IBDV given at 7, 14, 21 and 28 days post hatch and after challenge with USDA/STC IBDV at day 28 post hatch only.

| Age at Challenge | 4 Days Post Challenge | 11 Days Post Challenge |
| --- | --- | --- |
| Day 7 Variant E/1084 | + | − |
| Day 7 Negative Control | − | − |
| Day 14 Variant E/1084 | + | − |
| Day 14 Negative Control | − | − |
| Day 21 Variant E/1084 | + | − |
| Day 21 Negative Control | − | − |
| Day 28 Variant E/1084 | − | − |
| Day 28 USDA/STC | + | − |
| Day 28 Negative Control | − | − |

TABLE 3

Microscopic proventricular lesions at 4 and 11 days post challenge with Variant E/1084 IBDV given at 7, 14, 21 and 28 days post hatch and after challenge with USDA/STC IBDV at 28 days post hatch only.

| Age at Challenge | Day 4 Post* | Day 11 Post |
| --- | --- | --- |
| Day 7 NC | 1/10 | 0/5 |
| Day 7 Var E | 17/20 | 0/4 |
| Day 14 NC | 0/5 | 0/5 |
| Day 14 Var E | 5/5 | 0/5 |
| Day 21 NC | 0/5 | 0/5 |
| Day 21 Var E | 5/5 | 1/5 |
| Day 28 NC | 0/5 | 2/5 |
| Day 28 Var E | 5/5 | 0/5 |
| Day 28 USDA | 4/5 | 2/5 |

*Ratios represent the number of tissues exhibiting lesions over the total number of tissues screened.

TABLE 4

Microscopic bursal lesions of SPF white leghorn chickens at 4 and 11 days post challenge with Variant E/1084 IBDV given at 7, 14, 21 and 28 days post hatch and after challenge with USDA/STC IBDV given at 28 days post hatch only.

| Age at Challenge | Day 4 Post* | Day 11 Post |
| --- | --- | --- |
| Day 7 NC | 0/10 | 0/5 |
| Day 7 Var E | 10/10 | 4/4 |
| Day 14 NC | 0/5 | 0/5 |
| Day 14 Var E | 5/5 | 5/5 |
| Day 21 NC | 0/5 | 0/5 |
| Day 21 Var E | 5/5 | 5/5 |

TABLE 4-continued

Microscopic bursal lesions of SPF white leghorn chickens at 4 and 11 days post challenge with Variant E/1084 IBDV given at 7, 14, 21 and 28 days post hatch and after challenge with USDA/STC IBDV given at 28 days post hatch only.

| Age at Challenge | Day 4 Post* | Day 11 Post |
|---|---|---|
| Day 28 NC | 0/5 | 2/5 |
| Day 28 Var E | 5/5 | 5/5 |
| Day 28 USDA | 5/5 | 4/4 |

*Ratios represent number of tissues exhibiting lesions over the total number of tissues screened.

TABLE 5

Bursa: Body weight ratios of SPF white leghorn chickens 4 and 11 days post challenge with Variant E/1084 IBDV given at 7, 14, 21 and 28 days post hatch and after challenge with USDA/STC IBDV at 28 days post hatch only.

| Days PH** | Neg. Control | 7 | 14 | 21 | 28 Var E | 28 USDA |
|---|---|---|---|---|---|---|
| 11 | 3.46 ± 0.33 | 2.59 ± 0.23 | | | | |
| 18 | 5.06 ± 0.33 | 1.15 ± 0.33 | 4.15 ± 0.33 | | | |
| 25 | 5.19 ± 0.33 | | 1.26 ± 0.33 | 4.76 ± 0.33 | | |
| 32 | 5.50 ± 0.33 | | | 1.51 ± 0.33 | 3.69 ± 0.33 | 4.52 ± 0.37 |
| 39 | 5.97 ± 0.37 | | | | 1.13 ± 0.33 | 1.49 ± 0.37 |

*Numerical values within shaded boxes are significantly different from the negative control values at the $P < 0.05$ confidence interval.
**Days PH = Days post hatch and refers to the chronological age of the bird at necropsy.

TABLE 6

Proventriculus: Body weight ratios for SPF white leghorn chickens at 4 and 11 days post challenge with Variant E/1084 IBDV given at 7, 14, 21 and 28 days post hatch and after challenge with USDA/STC IBDV given at 28 days post hatch only.

| Days PH** | Neg. Control | 7 | 14 | 21 | 28 | 28 USDA |
|---|---|---|---|---|---|---|
| 11 | 7.84 ± 0.25 | 9.35 ± 0.17 | | | | |
| 18 | 7.44 ± 0.25 | 8.16 ± 0.28 | 7.35 ± 0.25 | | | |
| 25 | 6.30 ± 0.25 | | 6.76 ± 0.25 | 6.49 ± 0.25 | | |
| 32 | 5.76 ± 0.25 | | | 6.68 ± 0.25 | 6.08 ± 0.25 | 6.09 ± 0.28 |
| 39 | 5.48 ± 0.28 | | | | 5.60 ± 0.25 | 6.08 ± 0.28 |

*Numerical values within shaded boxes are significantly different from the negative control values at the $P < 0.05$ confidence interval.
**Days PH = Days post hatch and refers to the chronological age of the bird at necropsy.

TABLE 7

Spleen: Body weight ratios for SPF white leghorn chickens at 4 and 11 days post challenge with Variant E/1084 IBDV at 7, 14, 21 and 28 days post hatch, and challenge with USDA/STC IBDV given at day 28 post hatch only.

| Days PH** | Neg. Control | CHALLENGE DATE | | | | |
|---|---|---|---|---|---|---|
| | | 7 | 14 | 21 | 28 | 28 USDA |
| 11 | 0.98 ± 0.16 | 1.86 ± 0.11 | | | | |
| 18 | 1.37 ± 0.16 | 1.84 ± 0.16 | 2.22 ± 0.16 | | | |
| 25 | 1.5 ± 0.16 | | 1.45 ± 0.16 | 2.81 ± 0.16 | | |
| 32 | 1.74 ± 0.16 | | | 2.50 ± 0.16 | 2.86 ± 0.16 | 2.77 ± 0.18 |
| 39 | 2.81 ± 0.18 | | | | 2.56 ± 0.16 | 2.59 ± 0.18 |

*Numerical values within shaded boxes are significantly different from the negative control values at $P < 0.05$ confidence interval.
**Days PH = Days post hatch and refers to the chronological age of the bird at necropsy.

TABLE 8

Papillae scores of infected proventriculi from SPF white leghorn chickens at 4 and 11 days post challenge with Variant E/1084 IBDV at 7, 14, 21 and 28 days post hatch, and challenged with USDA/STC IBDV given at 28 days post hatch only.

| Days PH** | Neg. Control | CHALLENGE DATE | | | | |
|---|---|---|---|---|---|---|
| | | 7 | 14 | 21 | 28 Var E | 28 USDA |
| 11 | 0.00 ± 0.20 | 0.75 ± 0.14 | | | | |
| 18 | 0.00 ± 0.20 | 0.40 ± 0.20 | 0.70 ± 0.20 | | | |
| 25 | 0.00 ± 0.20 | | 0.00 ± 0.20 | 0.40 ± 0.20 | | |
| 32 | 0.00 ± 0.20 | | | 0.40 ± 0.20 | 1.60 ± 0.20 | 0.63 ± 0.23 |
| 39 | 0.13 ± 0.23 | | | | 0.50 ± 0.20 | 0.13 ± 0.23 |

*Numerical values within shaded boxes are significantly different from the negative control values at the $P < 0.05$ confidence interval.
**Days PH = Days post hatch and refers to the chronological age of the bird at necropsy.

TABLE 9

Virus inoculum preparation, route and volume of administration, and paired virus titer groups based on virus stock titers of USDA/STC IBDV and Variant E/1084 IBDV.

| Challenge Group | Virus Inoculum Dilution | Volume Inoculated | Treatment Identification | Equivalent Virus Titer Groups |
|---|---|---|---|---|
| Negative Control | NA | NA | NC | 0 |
| USDA/STC | undilute | 30 μl/eye | USDA 10X | A |
| USDA/STC | 1:10 | 30 μl/eye | USDA 1X | B |
| USDA/STC | 1:10 | 15 μl/eye | USDA 0.5X | C |
| Variant E/1084 | 1:1000 | 15 μl/eye | Variant E 1X | C |
| Variant E/1084 | 1:1000 | 30 μl/eye | Variant E 2X | B |
| Variant E/1084 | 1:100 | 30 μl/eye | Variant E 20X | A |

TABLE 10

AC-ELISA analysis of proventricular homogenates from SPF white leghorn chickens challenged at 32 days post hatch with different concentrations of USDA/STC IBDV and Variant E/1084 IBDV at 2, 3, 4, and 11 days post challenge.

| Treatment | Days Post Challenge | | | |
|---|---|---|---|---|
| | 2 | 3 | 4 | 11 |
| Negative Control | 0/8 (0%) | 0/8 (0%) | 0/8 (0%) | 0/8 (0%) |
| USDA - 0.5X | 1/8 (13%) | 6/8 (75%) | 2/6 (33%) | 0/8 (0%) |
| USDA - 1X | 4/8 (50%) | 7/8 (88%) | 4/5 (80%) | 0/8 (0%) |
| USDA - 10X | 0/8 (0%) | 8/8 (100%) | 0/8 (0%) | 0/8 (0%) |
| Variant E - 1X | 7/8 (88%) | 5/8 (63%) | 3/8 (38%) | 0/8 (0%) |
| Variant E - 2X | 2/8 (25%) | 3/8 (38%) | 1/8 (13%) | 0/8 (0%) |
| Variant E - 20X | 7/8 (88%) | 7/8 (88%) | 0/8 (0%) | 0/8 (0%) |

*Ratios represent the number of birds which tested positive over the number of birds tested by AC-ELISA.

TABLE 11

AC-ELISA analysis of bursal homogenates from SPF white leghorn chickens challenged at 32 days post hatch with different concentrations of USDA/STC IBDV and Variant E/1084 IBDV at 2, 3, 4, and 11 days post challenge.

| Treatment | Days Post Infection | | | |
|---|---|---|---|---|
| | 2 | 3 | 4 | 11 |
| Negative Control | 0/8 (0%) | 0/8 (0%) | 0/8 (0%) | 0/8 (0%) |
| USDA-0.5X | 8/8 (100%) | 6/7 (86%) | 6/6 (100%) | 0/8 (0%) |
| USDA-1X | 8/8 (100%) | 8/8 (100%) | 5/5 (100%) | 0/8 (0%) |
| USDA-10X | 3/8 (38%) | 8/8 (100%) | 8/8 (100%) | 0/8 (0%) |
| Variant E-1X | 8/8 (100%) | 8/8 (100%) | 1/8 (13%) | 0/8 (0%) |
| Variant E-2X | 3/8 (38%) | 4/8 (50%) | 7/8 (88%) | 0/8 (0%) |
| Variant E-20X | 6/8 (75%) | 7/8 (88%) | 8/8 (100%) | 0/8 (0%) |

*Ratios represent the number of birds which tested positive over the total number of birds tested by AC-ELISA.

TABLE 12

Microscopic proventricular lesions in SPF white leghorn chickens challenged at 32 days post hatch with different concentrations of USDA/STC IBDV and Variant E (1084-E) IBDV at 2, 3, 4, and 11 days post challenge.

| Treatment | Days Post Infection | | | |
|---|---|---|---|---|
| | 2 | 3 | 4 | 11 |
| Negative Control | 0/5 (0%) | 0/5 (0%) | 0/5 (0%) | 0/5 (0%) |
| USDA-0.5X | 4/5 (80%) | 5/5 (100%) | 5/5 (100%) | 0/5 (0%) |
| USDA-1X | 1/5 (20%) | 5/5 (100%) | 2/5 (40%) | 0/5 (0%) |
| USDA-10X | 1/5 (20%) | 5/5 (100%) | 2/5 (40%) | 0/5 (0%) |
| Variant E-1X | 3/5 (60%) | 2/4 (50%) | 2/5 (40%) | 0/5 (0%) |
| Variant E-2X | 0/5 (0%) | 1/5 (20%) | 4/5 (80%) | 0/5 (0%) |
| Variant E-20X | 1/5 (20%) | 5/5 (100%) | 3/5 (60%) | 0/5 (0%) |

*Ratios represent the number of birds exhibiting lesions over the number of birds screened.

TABLE 13

Microscopic bursal lesions in SPF white leghorn chickens challenged at 32 days post hatch with different concentrations of USDA/STC IBDV and Variant E (1084-E) IBDV at 2, 3, 4, and 11 days post challenge.

| | Days Post Infection | | | | | | | |
|---|---|---|---|---|---|---|---|---|
| Treatment | 2 | | 3 | | 4 | | 11 | |
| Negative Control | 0/5 | (0%) | 0/5 | (0%) | 0/5 | (0%) | 0/5 | (0%) |
| USDA-0.5 | 4/5 | (80%) | 5/5 | (100%) | 5/5 | (100%) | 5/5 | (100%) |
| USDA-1X | 2/5 | (40%) | 5/5 | (100%) | 5/5 | (100%) | 5/5 | (100%) |
| USDA-10X | 1/5 | (20%) | 5/5 | (100%) | 5/5 | (100%) | 5/5 | (100%) |
| Variant E-1X | 5/5 | (100%) | 5/5 | (100%) | 5/5 | (100%) | 5/5 | (100%) |
| Variant E-2X | 2/5 | (40%) | 2/5 | (40%) | 5/5 | (100%) | 5/5 | (100%) |
| Variant E-20X | 2/5 | (40%) | 5/5 | (100%) | 5/5 | (100%) | 5/5 | (100%) |

*Ratios represent the number of birds exhibiting lesions over the number of birds screened.

TABLE 14

Proventriculus: Body weight ratios for SPF white leghorn chickens challenged at 32 days post hatch with different concentrations of USDA/STC IBDV and Variant E/1084 IBDV at 2, 3, 4, and 11 days post challenge.

| | Days Post Challenge | | | |
|---|---|---|---|---|
| Challenge Groups | 2 | 3 | 4 | 11 |
| Negative Control | $6.28\pm0.22^{ab}$ | $5.52\pm0.22^{a}$ | $6.14\pm0.22^{a}$ | $5.6\pm0.21^{d}$ |
| USDA 0.5X | $5.67\pm0.22^{d}$ | $5.92\pm0.22^{a}$ | $5.68\pm0.25^{a}$ | $6.55\pm0.20^{abc}$ |
| USDA 1X | $6.33\pm0.22^{a}$ | $5.74\pm0.22^{a}$ | $6.12\pm0.28^{a}$ | $6.69\pm0.20^{ab}$ |
| USDA 10X | $5.53\pm0.22^{d}$ | $5.49\pm0.22^{a}$ | $6.16\pm0.22^{a}$ | $7.02\pm0.19^{a}$ |
| Variant E 1X | $5.99\pm0.22^{abc}$ | $5.96\pm0.22^{a}$ | $6.46\pm0.22^{a}$ | $6.12\pm0.23^{bcd}$ |
| Variant E 2X | $6.32\pm0.22^{ab}$ | $5.97\pm0.22^{a}$ | $5.99\pm0.22^{a}$ | $6.1\pm0.21^{cd}$ |
| Variant E 20X | $5.71\pm0.22^{bc}$ | $5.84\pm0.22^{a}$ | $6.17\pm0.22^{a}$ | $5.72\pm0.28^{d}$ |

* Values in shaded boxes with superscripts with different letters indicate significant differences at the $P < 0.05$ confidence interval.

TABLE 15

Bursa: Body weight ratios for SPF white leghorn chickens challenged at 32 days post hatch with different concentrations of USDA/STC IBDV and Variant E/1084 IBDV at 2, 3, 4, and 11 days post challenge.

| Challenge Groups | Days Post Challenge | | | |
|---|---|---|---|---|
| | 2 | 3 | 4 | 11 |
| Negative Control | 5.52±0.44$^{ab}$ | 5.63±0.44$^a$ | 5.13±0.44$^a$ | 5.95±0.41$^a$ |
| USDA 0.5X | 5.97±0.44$^a$ | 4.42±0.44$^a$ | 4.63±0.51$^{ab}$ | 1.13±0.30$^a$ |
| USDA 1X | 5.46±0.44$^{ab}$ | 4.70±0.44$^a$ | 4.95±0.56$^{ab}$ | 1.02±0.4$^a$ |
| USDA 10X | 4.39±0.44$^b$ | 3.77±0.44$^a$ | 4.40±0.44$^{ab}$ | 1.73±0.39$^a$ |
| Variant E 1X | 6.06±0.44$^a$ | 4.53±0.44$^a$ | 2.29±0.44$^c$ | 1.59±0.47$^a$ |
| Variant E 2X | 4.54±0.44$^b$ | 4.78±0.44$^a$ | 4.73±0.44$^{ab}$ | 1.21±0.42$^a$ |
| Variant E 20X | 6.14±0.44$^a$ | 4.34±0.45$^a$ | 3.76±0.44$^c$ | 0.83±0.56$^a$ |

\* Values in shaded boxes with superscripts with different letters indicate significant differences at the P < 0.05 confidence interval.

TABLE 15

Spleen: Body weight ratios for SPF white leghorn chickens challenged at 32 days post hatch with different concentrations of USDA/STC IBDV and Variant E/1084 IBDV at 2, 3, 4, and 11 days post challenge.

| Challenge Groups | Days Post Challenge | | | |
|---|---|---|---|---|
| | 2 | 3 | 4 | 11 |
| Negative Control | 2.20±0.21$^{bc}$ | 1.67±0.21$^d$ | 1.77±0.21$^c$ | 2.19±0.20$^a$ |
| USDA 0.5X | 2.78±0.21$^b$ | 2.93±0.21$^b$ | 2.89±0.24$^b$ | 2.78±0.19$^a$ |
| USDA 1X | 2.74±0.21$^b$ | 2.86±0.21$^b$ | 3.62±0.28$^b$ | 2.70±0.19$^a$ |
| USDA 10X | 2.31±0.21$^{bc}$ | 2.32±0.21$^c$ | 3.77±0.21$^b$ | 2.76±0.19$^a$ |
| Variant E 1X | 3.60±0.21$^a$ | 3.89±0.21$^a$ | 3.58±0.21$^a$ | 2.48±0.22$^a$ |
| Variant E 2X | 2.12±0.21$^c$ | 2.57±0.21$^c$ | 3.21±0.21$^b$ | 2.79±0.20$^a$ |
| Variant E 20X | 2.66±0.21$^{bc}$ | 2.88±0.21$^{bc}$ | 3.31±0.21$^{ab}$ | 2.76±0.26$^a$ |

\* Values in shaded boxes with superscripts with different letters indicate significant differences at the P < 0.05 confidence interval.

TABLE 17

Challenge group identification and outline of viral inoculums and volumes administered to SPF white leghorn chickens at 28 days post hatch.

| Challenge Groups | Challenge Given |
|---|---|
| Negative Control | None |
| Negative Control + Copper Sulfate | None |
| USDA/STC | USDA/STC 30 μl bilateral eyedrop |
| USDA/STC + Copper Sulfate | USDA/STC 30 μl bilateral eyedrop |
| 0.5X USDA/STC + Copper Sulfate | USDA/STC 15 μl bilateral eyedrop |
| Variant 1084-E | Variant E 30 μl bilateral eyedrop |
| Variant 1084-E + Copper Sulfate | Variant E 30 μl bilateral eyedrop |
| REO S1133 | REO S1133 100 μl oral |
| REO S1133 + Copper Sulfate | REO S1133 100 μl oral |
| USDA/STC + REO S1133 | USDA/STC 30 μl bilateral eyedrop REO S1133 100 μl oral |
| USDA/STC + REO S1133 + Copper Sulfate | USDA/STC 30 μl bilateral eyedrop REO S1133 100 μl oral |
| Variant E/1084 + REO S1133 | Variant E 30 μl bilateral eyedrop REO S1133 100 μl oral |
| Variant E/1084 + REO + Copper Sulfate | Variant E 30 μl bilateral eyedrop REO S1133 100 μl oral |

TABLE 18

AC-ELISA analysis of bursal and proventricular homogenates from SPF white leghorn chickens at 4 and 11 days post challenge with Variant E/1084 IBDV in the presence or absence of REO virus and/or copper sulfate.

| | Bursa | | Proventriculus | |
|---|---|---|---|---|
| Treatment | Day 4 | Day 11 | Day 4 | Day 11 |
| NC | 0/10 | 0/10 | 0/10 | 0/10 |
| NC + CS | 0/10 | 0/10 | 0/10 | 0/10 |
| Reo Only | 0/10 | 0/10 | 0/10 | 0/10 |
| Reo + CS | 0/10 | 0/10 | 0/10 | 0/10 |
| Var E Only | 8/10 | 0/10 | 3/10 | 0/10 |
| Var E + CS | 7/10 | 0/10 | 3/10 | 0/10 |
| Var E + REO + CS | 9/10 | 0/10 | 0/10 | 0/10 |

\*Ratios represent the number of individual tissue homogenates that test positive over the total number of samples tested for that challenge group
NC = Negative Control
CS = Copper Sulfate

TABLE 19

AC-ELISA analysis of bursal and proventricular homogenates from SPF white leghorn chickens at 4 and 11 days post challenge with USDA/STC IBDV in the presence or absence of REO virus and/or copper sulfate.

| | Bursa | | Proventriculus | |
|---|---|---|---|---|
| Treatment | Day 4 | Day 11 | Day 4 | Day 11 |
| NC | 0/10 | 0/10 | 0/10 | 0/10 |
| NC + CS | 0/10 | 0/10 | 0/10 | 0/10 |
| Reo Only | 0/10 | 0/10 | 0/10 | 0/10 |
| Reo + CS | 0/10 | 0/10 | 0/10 | 0/10 |
| USDA/STC Only | 8/10 | 0/10 | 5/10 | 0/10 |
| USDA/STC + CS | 6/10 | 0/10 | 2/10 | 0/10 |
| 1/2 USDA + CS | 9/10 | 0/10 | 4/10 | 0/10 |

TABLE 19-continued

AC-ELISA analysis of bursal and proventricular homogenates from SPF white leghorn chickens at 4 and 11 days post challenge with USDA/STC IBDV in the presence or absence of REO virus and/or copper sulfate.

|  | Bursa | | Proventriculus | |
|---|---|---|---|---|
| Treatment | Day 4 | Day 11 | Day 4 | Day 11 |
| USDA/STC + REO + CS | 9/10 | 0/8 | 4/10 | 0/8 |
| USDA/STC + REO | 6/10 | 0/10 | 4/10 | 0/10 |

*Ratios represent the number of individual tissue homogenates that test positive over the total number of samples tested for that challenge group.
NC = Negative Control
CS = Copper Sulfate

TABLE 20

Gross lesion scores from the proventriculus of SPF white leghorn chickens at 4 days post challenge with Variant E/1084 IBDV, in the presence or absence of REO virus, and/or copper sulfate.

| Treatment | Hemorrhage | Papillae | Gizzard |
|---|---|---|---|
| NC | 0.00$^c$ | 0.00$^d$ | 1.00$^{ab}$ |
| NC + CS | 0.00$^c$ | 0.00$^d$ | 1.60$^a$ |
| Reo Only | 0.00$^c$ | 0.21$^{cd}$ | 0.57$^{bc}$ |
| Reo + CS | 0.00$^c$ | 0.00$^d$ | 0.43$^{bc}$ |
| Var E. Only | 0.08$^c$ | 0.54 | 1.00$^{ab}$ |
| Var E + CS | 0.11$^c$ | 1.00 | 0.78$^{bc}$ |
| Var E + Reo + CS | 0.27$^c$ | 0.27 | 0.78$^{bc}$ |

*Values in shaded boxes with different superscripts are significantly different from the negative control at the P < 0.05 confidence interval.
NC = Negative Control
CS = Copper Sulfate

TABLE 21

Gross Lesions in the proventriculus of SPF white leghorn chickens at 4 days post challenge with USDA/STC IBDV in the presence or absence of REO virus and/or copper sulfate.

| Treatment | Hemorrhage | Papillae | Gizzard |
|---|---|---|---|
| NC | 0.00$^c$ | 0.00$^d$ | 1.00$^{ab}$ |
| NC + CS | 0.00$^c$ | 0.00$^d$ | 1.60$^a$ |
| Reo Only | 0.00$^c$ | 0.21$^{cd}$ | 0.57$^{bc}$ |
| Reo + CS | 0.00$^c$ | 0.00$^d$ | 0.43$^{bc}$ |
| USDA/STC Only | 0.42$^c$ | 0.75 | 0.75$^{bc}$ |
| USDA/STC + CS | 1.64 | 0.27$^{bcd}$ | 0.18 |
| 1/2 USDA/STC + CS | 0.36 | 0.56 | 1.00$^{ab}$ |
| USDA/STC + Reo + CS | 0.14$^c$ | 0.71 | 0.25 |
| USDA/STC + Reo | 1.00 | 0.82 | 0.18 |

*Values in shaded boxes with different superscripts are significantly different from the negative control at the P < 0.05 confidence interval.
NC = Negative Control
CS = Copper Sulfate

TABLE 22

Microscopic lesions in the bursa and proventriculus of SPF white leghorn chickens at 4 and 11 days post challenge with Variant E11084 IBDV in the presence or absence of REO virus and/or copper sulfate.

|  | Bursa | | Proventriculus | |
|---|---|---|---|---|
| Treatment | Day 4 | Day 11 | Day 4 | Day 11 |
| NC | 0/10 | 0/10 | 0/10 | 0/10 |
| NC + CS | 0/10 | 0/10 | 0/10 | 0/10 |
| Reo | 0/10 | 0/10 | 0/10 | 0/10 |
| Reo + CS | 0/10 | 0/10 | 0/10 | 0/10 |
| Var. E | 10/10 | 10/10 | 10/10 | 10/10 |
| Var. E + CS | 10/10 | 10/10 | 10/10 | 10/10 |
| Var. E + CS + Reo | 10/10 | 10/10 | 10/10 | 10/10 |

*Ratios represent the number of samples exhibiting lesions over the total number of samples screened for that challenge group.
NC = Negative Control
CS = Copper Sulfate

TABLE 23

Microscopic lesions in the bursa and proventriculus of SPF white leghorn chickens at 4 and 11 days post challenge with USDA/STC IBDV in the presence or absence of REO virus or copper sulfate.

|  | Bursa | | Proventriculus | |
|---|---|---|---|---|
| Treatment | Day 4 | Day 11 | Day 4 | Day 11 |
| NC | 0/10 | 0/10 | 0/10 | 0/10 |
| NC + CS | 0/10 | 0/10 | 0/10 | 0/10 |
| Reo Only | 0/10 | 0/10 | 0/10 | 0/10 |
| Reo + CS | 0/10 | 0/10 | 0/10 | 0/10 |
| USDA STC Only | 10/10 | 10/10 | 9/10 | 0/10 |
| USDA/STC + CS | 10/10 | 10/10 | 10/10 | 0/10 |
| 1/2 USDA/STC + CS | 10/10 | 8/8 | 9/10 | 0/8 |
| USDA/STC + Reo + CS | 9/9 | 8/8 | 9/9 | 0/8 |
| USDA/STC + Reo | 10/10 | 10/10 | 10/10 | 0/10 |

*Ratios represent the number of samples exhibiting lesions over the total number of samples screened for that challenge group.
NC = Negative Control
CS = Copper Sulfate

TABLE 24

Organ to body weight ratios of SPF white leghorn chickens at 4 and 11 days post challenge with Variant E/1084 IBDV in the presence or absence of REO virus, and/or copper sulfate.

|  | Bursa | | Spleen | | Proventriculus | |
|---|---|---|---|---|---|---|
| Treatment | Day 4 | Day 11 | Day 4 | Day 11 | Day 4 | Day 11 |
| NC | 5.74$^a$ | 6.59$^{ab}$ | 1.63$^c$ | 2.26$^{de}$ | 6.17$^{bcd}$ | 6.06$^d$ |
| NC + CS | 4.85$^{ab}$ | 5.96$^{bc}$ | 1.52$^c$ | 1.85$^{de}$ | 5.86$^{cd}$ | 6.19$^{cd}$ |
| Reo Only | 5.51$^a$ | 5.67$^c$ | 1.75$^c$ | 2.18$^e$ | 5.95$^{cd}$ | 5.92$^d$ |
| Reo + CS | 5.69$^a$ | 7.10$^a$ | 1.96$^c$ | 2.29$^{de}$ | 6.31$^{bcd}$ | 6.54$^{bcd}$ |
| Var E Only | 3.17 | 1.41 | 3.25 | 3.47 | 6.11$^{bcd}$ | 6.63$^{bcd}$ |
| Var E + CS | 3.74 | 1.44 | 3.07 | 3.08$^{ab}$ | 6.44$^{abc}$ | 6.54$^{bcd}$ |
| Var E + Reo + CS | 3.49 | 1.40 | 2.51 | 2.48$^{bcde}$ | 6.40$^{abc}$ | 7.46 |

*Values in shaded boxes with different superscripts are significantly different from the negative control at the P < 0.05 confidence interval.
NC = Negative Control
CS = Copper Sulfate

TABLE 25

Organ to body weight ratios of SPF white leghorn chickens at 4 and 11 days post challenge with USDA/STC IBDV in the presence or absence of REO virus and/or copper sulfate.

|  | Bursa | | Spleen | | Proventriculus | |
|---|---|---|---|---|---|---|
| Treatment | Day 4 | Day 11 | Day 4 | Day 11 | Day 4 | Day 11 |
| NC | 5.74$^a$ | 6.59$^{ab}$ | 1.63$^c$ | 2.26$^{de}$ | 6.17$^{bcd}$ | 6.06$^d$ |
| NC + CS | 4.85$^{ab}$ | 5.96$^{bc}$ | 1.52$^c$ | 1.85$^{de}$ | 5.86$^{cd}$ | 6.19$^{cd}$ |
| Reo Only | 5.51$^a$ | 5.67$^c$ | 1.75$^c$ | 2.18$^e$ | 5.95$^{cd}$ | 5.92$^d$ |
| Reo + CS | 5.69$^a$ | 7.10$^a$ | 1.96$^c$ | 2.29$^{de}$ | 6.31$^{bcd}$ | 6.54$^{bcd}$ |
| USDA/STC Only | 4.33$^{bc}$ | 1.44$^e$ | 3.23$^a$ | 2.86$^{abcd}$ | 7.05$^e$ | 7.44$^e$ |
| USDA/STC + CS | 4.78$^{ab}$ | 1.51$^e$ | 2.81$^b$ | 2.97$^{ab}$ | 6.20$^{bcd}$ | 6.83$^{abc}$ |
| 1/2 USDA/STC + CS | 4.76$^{ab}$ | 1.29$^e$ | 3.23$^a$ | 2.35$^{cde}$ | 6.05$^{bcd}$ | 6.17$^{cd}$ |
| USDA/STC + Reo + CS | 3.06$^e$ | 0.98$^e$ | 3.09$^a$ | 2.42$^{bcde}$ | 6.65$^{ab}$ | 7.10$^e$ |
| USDA/STC + Reo | 3.17$^e$ | 1.23$^e$ | 3.12$^a$ | 2.91$^{abcd}$ | 5.70$^d$ | 6.59$^{bcd}$ |

*Values in shaded boxes with different superscripts are significantly different from the negative control at the P < 0.05 confidence interval.
NC = Negative Control
CS = Copper Sulfate

TABLE 26

TUNEL staining of tissue sections 4 days post challenge with USDA/STC IBDV, Variant E/1084 IBDV, and REO (S-1133) in the presence or absence of copper sulfate feed supplement.

| Experimental Group | Bursa | Proventriculus |
|---|---|---|
| Negative Control | − | − |
| Negative Control + Copper Sulfate | − | − |
| USDA/STC | +++ | ++ |
| Variant E | ++ | + |
| REO | +/31 | − |
| USDA/STC + REO | +++ | ++ |
| Variant E + REO | ++ | + |
| USDA/STC + Copper Sulfate | +++ | +++ |
| Variant E + Copper Sulfate | ++ | ++ |
| REO + Copper Sulfate | − | − |
| USDA/STC + REO + Copper Sulfate | ++++ | +++ |
| Variant E + REO + Copper Sulfate | +++ | ++ |
| ½ USDA/STC + Copper Sulfate | +++ | +++ |

* + indicates the presence of specific fluorescence following TUNEL staining. multiple "+"s indicate visual intensity assessment.

TABLE 27

AC-ELISA analysis of individual tissue homogenates from SPF white leghorn chickens challenged at 28 days post hatch with Variant E/DEL, Variant E-1084, and USDA/STC IBDV at 4 days post challenge.

| Challenge Group | Bursa | Spleen | Proventriculus |
|---|---|---|---|
| Negative Control | 0/10 | 0/10 | 0/10 |
| Variant E/DEL | 10/10 | 0/10 | 3/10 |
| Variant E/1084 | 7/10 | 5/10 | 7/10 |
| USDA/STC | 10/10 | 0/10 | 8/10 |

*Ratios represent the number of samples testing positive over the total number of samples tested for each experimental group.

TABLE 28

AC-ELISA analysis of individual tissue homogenates from SPF white leghorn chickens challenged at 28 days post hatch with Variant E/DEL, Variant E/1084, and USDA/STC IBDV at 11 days post challenge

| Challenge Group | Bursa | Spleen | Proventriculus |
|---|---|---|---|
| Negative Control | 0/10 | 0/10 | 0/10 |
| Variant E/DEL | 0/10 | 0/10 | 0/10 |
| Variant E/1084 | 0/10 | 0/10 | 0/10 |
| USDA/STC | 0/10 | 0/10 | 0/10 |

*Ratios represent the number of samples testing positive over the total number of samples tested for each experimental group.

TABLE 29

Histological lesions in the bursa and proventriculus of SPF white leghorn chickens challenged at 28 days post hatch with Variant E/DEL, Variant E/1084, and USDA/STC IBDV at 4 days post challenge.

| Challenge Group | Bursa | Proventriculus |
|---|---|---|
| Negative Control | 0/10 | 0/10 |
| Variant E/DEL | 10/10 | 4/10 |
| Variant E/1084 | 7/10 | 8/10 |
| USDA/STC | 9/10 | 10/10 |

*Ratios represent the number of tissues positive for the presence of lesions over the total number of tissues screened for each experimental group.

TABLE 30

Histological lesions in the bursa and proventriculus of SPF white leghorn chickens challenged at 28 days post hatch with Variant E/DEL, Variant E/1084, and USDA/STC IBDV at 11 days post challenge.

| Challenge Group | Bursa | Proventriculus |
|---|---|---|
| Negative Control | 0/10 | 0/10 |
| Variant E/DEL | 10/10 | 0/10 |
| Variant E/1084 | 10/10 | 0/10 |
| USDA/STC | 10/10 | 0/10 |

*Ratios represent the number of tissues positive for the presence of lesions over the total number of tissues screened for each experimental group.

TABLE 31

Organ to body weight ratios of broiler chickens challenged at 35 days post hatch with USDA/STC IBDV in the presence or absence of copper sulfate at 4 days post challenge.

| Treatment | Bursa | Spleen | Proventriculus |
|---|---|---|---|
| NC | 2.29$^b$ | 1.81$^b$ | 5.14$^a$ |
| NC + CS | 2.44$^{ab}$ | 1.70$^b$ | 5.15$^a$ |
| USDA/STC | 2.94a | 2.78$^a$ | 5.24$^a$ |
| USDA + CS | 2.37$^b$ | 2.40$^a$ | 5.11 |

*Values in shaded boxes with different superscripts are significantly different from the negative control at P < 0.05 confidence interval.

TABLE 32

Organ to body weight ratios of broiler chickens challenged at 35 days post hatch with USDA/STC IBDV in the presence or absence of copper sulfate at 11 days post challenge.

| Treatment | Bursa | Spleen | Proventriculus |
|---|---|---|---|
| NC | 3.01$^a$ | 2.64$^a$ | 5.03$^a$ |
| NC + CS | 2.86$^a$ | 2.36$^{ab}$ | 4.95$^a$ |
| USDA/STC | 0.90 | 1.89 | 5.30$^a$ |
| USDA + CS | 0.89 | 2.03$^{bc}$ | 5.12$^a$ |

*Values in shaded boxes with different superscripts are significantly different from the negative control at P < 0.05 confidence interval.

TABLE 33

Gross Lesion scores from broiler chickens challenged at 35 days post hatch with USDA/STC IBDV in the presence or absence of copper sulfate at 4 and 11 days post hatch.

| | Papillae | Impaction |
|---|---|---|
| Treatment | Day 4 | Day 11 |
| NC | 0.25$^b$ | 0.39$^b$ |
| NC + CS | 0.57$^b$ | 0.23$^b$ |
| USDA/STC | 1.60 | 0.84 |
| USDA + CS | 0.76$^b$ | 0.08$^b$ |

*Values in shaded boxes with different superscripts are significantly different from the negative control at P < 0.05 confidence interval.

TABLE 34

AC-ELISA analysis of bursal and proventricular homogenates from 35 post hatch broilers at 4 and 11 days post challenge with USDA/STC IBDV in the presence or absence of copper sulfate.

| | Bursa | | Proventriculus | |
|---|---|---|---|---|
| Experimental Group | Day 4 | Day 11 | Day 4 | Day 11 |
| Negative Control | 0/10 | 0/10 | 0/10 | 0/10 |
| Negative Control + CS | 0/10 | 0/10 | 0/10 | 0/10 |
| USDA/STC IBDV | 7/10 | 0/10 | 4/10 | 0/10 |
| USDA/STC IBDV + CS | 6/10 | 0/10 | 5/10 | 0/10 |

TABLE 35

Microscopic lesions in the bursa and proventriculus of broiler chickens challenged at 35 days post hatch with USDA/STC IBDV in the presence or absence of copper sulfate at 4 and 11 days post challenge.

| | Bursa | | Proventriculus | |
|---|---|---|---|---|
| Challenge Group | Day 4 | Day 11 | Day 4 | Day 11 |
| Negative Control | 0/10 | 10/10 | 0/10 | 0/10 |
| Negative Control + CS | 0/10 | 9/10 | 0/10 | 0/10 |
| USDA/STC | 9/10 | 10/10 | 4/10 | 0/10 |
| USDA/STC + CS | 6/10 | 10/10 | 5/10 | 0/10 |

TABLE 36

AC-ELISA analysis of bursal and proventricular homogenates for SPF white leghorn chickens challenged at 28 days post hatch with USDA/STC IBDV and suspect IBDV field isolates at 4 and 11 days post challenge.

| | Bursa | | Proventriculus | |
|---|---|---|---|---|
| Challenge Groups | Day 4 | Day 11 | Day 4 | Day 11 |
| Negative Control | 0/10 | 0/10 | 0/10 | 0/10 |
| USDA/STC | 9/10 | 0/9 | 10/10 | 0/9 |
| RB Texas 3 | 6/11 | 0/10 | 5/11 | 0/10 |
| RB Texas 4 | 7/11 | 0/9 | 2/11 | 0/10 |
| Farm 57-7 | 9/9 | 0/9 | 6/9 | 0/9 |
| W/L #22 | 0/8 | 0/9 | 0/8 | 0/9 |
| W/L #33 | 0/8 | 0/9 | 0/8 | 0/9 |
| W/L #39 | 7/8 | 0/9 | 5/8 | 0/9 |

*Ratios represent the number of tissue homogenates testing positive over the total number of tissue homogenates tested for each challenge group.

TABLE 37

Organ to body weight ratios of SPF white leghorn chickens challenged at 28 days post hatch with USDA/STC IBDV and suspect IBDV field isolates at 4 days post challenge.

| Challenge Groups | Bursa | Spleen | Proventriculus |
|---|---|---|---|
| Negative Control | 5.50$^b$ | 1.86$^c$ | 6.35$^a$ |
| USDA/STC | 4.48$^{bc}$ | 2.05 | 6.58$^a$ |
| RB Texas 3 | 3.63 | 3.04 | 6.86$^a$ |
| RB Texas 4 | 3.68 | 3.81 | 7.15$^a$ |
| Farm 57-7 | 3.84 | 2.76 | 6.27$^a$ |
| W/L #22 | 6.55$^a$ | 1.74$^c$ | 6.01$^a$ |
| W/L #33 | 5.20$^b$ | 1.21$^c$ | 6.68$^a$ |
| W/L #39 | 3.79 | 1.57 | 6.55$^a$ |

*Values in shaded boxes with different superscripts are significantly different from the negative control at P < 0.05 confidence interval.

TABLE 38

Organ to body weight ratios of SPF white leghorn chickens challenged at 28 days post hatch with USDA/STC IBDV and suspect IBDV field isolates at 11 days post challenge.

| Challenge Groups | Bursa | Spleen | Proventriculus |
|---|---|---|---|
| Negative Control | 4.64$^a$ | 2.14$^a$ | 5.71$^a$ |
| USDA/STC | 1.38$^b$ | 2.58$^a$ | 6.41$^a$ |
| RB Texas 3 | 1.28 | 3.42$^a$ | 6.90$^a$ |
| RB Texas 4 | 1.13 | 2.98$^a$ | 7.35$^a$ |
| Farm 57-7 | 1.36 | 2.08$^a$ | 6.30$^a$ |
| W/L #22 | 6.19$^a$ | 1.80$^a$ | 6.21$^a$ |
| W/L #33 | 6.67$^a$ | 1.72$^a$ | 6.26$^a$ |
| W/L #39 | 1.46 | 2.21$^a$ | 6.03$^a$ |

*Values in shaded boxes with different superscripts are significantly different from the negative control at P < 0.05 confidence interval.

The present invention is directed to proventricular origin infectious bural disease viruses and any derivatives of these viruses that might be used as vaccines. This would include any viruses that are modified or attenuated by passage in cultured cells, eggs or any other living system. This would also include any of these viruses that are inactivated for use in a killed vaccine. The present invention is also directed to new species of IBDV.

The present invention is directed to poultry virus isolates or strains believed to be a new strain or strains of infectious bursal disease virus (IBDV) which infects the proventriculus. More particularly, the present invention is directed to one or more newly isolated strains referred to as the Texas RB Strain, Texas RB 3, Texas RB 4, F57-7, HBS, W/L 39, GAR 1, and the like of infectious disease virus which was isolated from broiler chickens. The isolated strains have been adapted to embryonated chicken eggs and have been passed in SPF White Leghorn Chickens 1×. The virus is a proventricular origin infectious bursal disease virus and a candidate for a vaccine for chickens against an enteric form of infectious bursal disease virus. It was noted that a number of IBDV infected broiler chickens suffered from proventriculitis, each having swollen, enlarged proventriculus, with the inner surface having hemorrhage and flattened papillae. The virus strains isolated from the infected proventriculi may be used to produce a modified live vaccine or an inactivated vaccine form for vaccinating for IBDV and/or proventriculitis. Also, it was discovered that a combination of IBDV and the feed additive copper sulfate (CS) increased the mortality rate and that a combination of IBDV, Reovirus and CS further increased the mortality rate.

ARS-94015 is a proventricular tissue homogenate collected from a pool of affected field broiler proventriculi. It will induce a proventriculitis when used to experimentally infect broiler and white leghorn chickens. This material has been subjected to isolation procedures and the resulting product has been partially characterized.

Other proventricular homogenates from affected field broiler proventriculi have been subjected to virus isolation procedures and isolates of infectious bursal virus successfully obtained. These isolates are identified as Texas RB 3, Texas RB 4, F57-7, W/L 39, HBS, and GAR 1.

Proventriculitis, proventricular enlargement and proventricular tearing have been observed for many years in the broiler industry. Research at the University of Arkansas has shown that infectious bursal disease virus can cause proventriculitis and may be a major cause of this condition. Unique infectious bursal disease viruses have been isolated from the proventriculus of affected broilers from the field. These viruses have been shown to infect and induce pathology in the proventriculus of experimentally infected chickens and this pathology has been shown to be exacerbated by copper sulfate and reovirus.

Vaccines can be made from these proventricular orign IBDVs. These vaccines may very well protect vaccinated broilers against proventriculitis, proventricular enlargement, proventricular tearing and other gastrointestinal pathology. The vaccines derived from these unique proventricular origin IBDVs may have great commercial value.

The present invention is directed to IBDVs which are proventricular in origin. The present invention is also directed to derivatives of the proventricular IBDVs which can be made to include attenuated, inactivated, molecular altered or mutated that can or possibly could be used as a vaccine against proventriculitis, proventricular enlargement, proventricular tearing or other abnormalities involving the gastrointestinal tract excluding the bursa of Fabricius which is an organ of immunity that communicates with the popsterior gut.

In regards to method of administration, a vaccine derived from a proventricular origin IBDV of the present invention would be given by standard acceptable methods that are commonly practiced in the poultry industry including being given by aerosol, drinking water, eyedrop, injection (SQ or inovo), feed, etc.

Our research has shown that proventricular origin IBDV and certain challenge strains of IBDV do infect and cause pathology in the proventriculus when given on days 7, 14, 21 and 28 post hatch. IBDV is an RNA virus and as such does not cause intra-nuclear inclusions.

Wideman et al. and Jensen et al. were able to induce proventriculitis by feeding elevated levels of copper sulfate only. Copper sulfate is a known irritant of the gastrointestinal tract and of mucus membranes. Copper sulfate has been known to cause proventricular enlargement for many years. Our work combined IBDV+copper. The levels of copper used in our research induced no lesions in the proventriculus either gross or microscopic. Our research showed that when IBDV and copper was given together there was elevated mortality from this combination. There is a synergistic effect between copper and IBDV. Proventricular origin IBDV is an irritant to the proventriculus and possibly other areas of the gastrointestinal tract. The fact that this synergism exists is an interesting observation. Since copper is widely used in the broiler industry this is another reason for protecting chickens against the gastrointestinal effects of IBDV along with the possible lethal synergistic effect of IBDV and copper together.

The problem with trying to vaccinate against IBDV is vaccine timing. All poultry houses are seeded with IBDVs. As soon as the maternal immunity drops these viruses will induce infection in the chicken and cause serious problems. When infection occurs these viruses damage the intestinal tract and contribute to proventriculitis and the so-called malabsorption/feed passage syndrome.

If the above is true, then we should be able to vaccinate for the condition. The proventricular origin viruses may be a better alternative than what presently exists. By vaccinating the birds at 2–3 weeks post hatch, and again at 4–5 weeks, and then again at 6–7 weeks, we may be able to avoid the problem of the timing of vaccination and the interference that occurs from maternal immunity. It is conceivable that these viruses may also be able to induce local immunity in the face of maternal antibody.

Since about 65–70% of the cost of raising poultry is the poultry feed, a vaccine or method of treatment which reduces or eliminates the clinical manifestation of proventriculitis and/or the so-called malabsorption/feed passage syndrome may be able to reduce the overall cost of raising poultry by, for example, 5% or more.

Conventional poultry vaccines are given to immunosuppression or to boost maternal immunity. In accordance with the present invention, we can vaccinate to protect against the clinical manifestation of proventriculitis by vaccinating the birds one or more times, preferably at least twice, two or more weeks post hatch. Also, it may be necessary to use a relatively "hot" virus in the vaccine to protect against the clinical manifestation of proventriculitis.

Four-week old SPF white leghorn chickens were challenged by eyedrop with ehter USDA/STC or Variant E IBDV. Four days post challenge 10 birds from each group were weighed, bled, euthanized, and necropsied. Tissues were scored for gross lesions, collected, and individually weighed. Samples from the proventriculus, bursa and spleen were placed in 10% buffered formalin, and processed for standard hematoxylin eosin and apoptosis staining. All tissues were paraffin embedded and cut into 5 um sections. Tissue sections for apoptosis staining were placed on poly-L-lysine coated slides, deparaffinized, and dehydrated through graded alcohols. Sections were then stained to determine the presence of apoptotic cells using the Terminal dinucleotidyl d-UTP Nick End Labeling (TUNEL) procedure and counterstained with 4', 6-Diamidine-2'-phenylindole dihydrochloride (DAPI). Slides were viewed and photographed with an Olympus microscope to determine the presence/absence of cells with specific green fluorescence.

Tissues harvested from negative control SPF leghorns demonstrated occasional small areas with apoptotic staining in the proventriculus and bursa. Birds challenged with the Variant E and USDA/STC IBDV demonstrated extensive Apoptotic staining in the proventriculus and bursa at 4 days post challenge. Apoptotic staining in the bursa was evident within infected bursal follicles. Apoptotic cells were present in the glands, lamina propria and extensively in the villi of the proventriculus. No differences were noted between the number of apoptotic cells present in tissues from birds challenged with Variant E IBDV or USDA/STC IBDV.

1. Overview of Research Findings

Infectious Bursal Disease (IBD) virus infection induces gross and histopathologic lesions within the proventriculus at 4 days post challenge in SPF white leghorn chickens. The presence of IBD virus has also been associated with proventriculitis syndrome in commercial broiler chickens.

Pathology in the proventriculus associated with IBD virus infection is transient as demonstrated by the absence of lesions at 11 days post challenge. Current studies involve the determination of the mechanism(s) by which acute IBD virus infection induces lesions in the proventriculus.

Formalin fixed tissue sections from affected proventriculi and bursae were evaluated for the presence of fragmented cellular DNA a common indicator of cellular apoptotic activity. Tissue sections were stained by the terminal deoxynucleotidyl transferase mediated dUTP-biotin nick end labeling (TUNEL) method to visually detect the presence of nuclear fragmentation.

2. Bottom Line

Tissues were harvested from SPF white leghorn chickens challenged with USDA/STC or Variant E IBD viruses 4 days prior. TUNEL staining revealed the presence of DNA fragmentation in bursal and proventricular tissues from challenged birds only.

Staining intensity in bursal sections was highest in the medulla and cortex of the bursal follicles with low levels in the surrounding connective tissue. Proventricular staining was localized within the villi with occasional involvement of the glandular tissue. However, the amount or intensity of fluorescent labeling was not quantitated.

TUNEL staining intensity in the proventriculus and bursa was highly associated with confirmed IBDV histopathogy lesions, suggesting that cellular mechanisms of apoptosis are involved in the induction of lesions associated with IBD virus infection.

Thus, it will be appreciated that as a result of the present invention, poultry viral isolates, vaccines, and method are provided by which the principal objective, among others, is completely fulfilled. It is contemplated and will be apparent to those skilled in the art from the preceeding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

What is claimed is:

1. A poultry virus isolate having the identifying characteristics of an isolate selected from the group of F57-7, Texas RB 3, and Texas RB 4.

2. A poultry vaccine utilizing at least one of the poultry virus isolates of claim 1.

3. A vaccine suitable for immunizing chickens against proventriculitis syndrome comprising an IBD virus having the identifying characteristics of an isolate selected from the group of F57-7, Texas RB 3, and Texas RB 4, and combinations or variants thereof.

4. The vaccine of claim 3 defined further as containing an attenuated, modified, inactivated, or killed form of the isolate.

5. A method of protecting a chicken from clinical signs of proventriculitis syndrome or disease caused by a virus having all of the identifying characteristics of an isolate selected from the group of F57-7, Texas RB 3, and Texas RB 4, comprising administering an effective amount of the vaccine of claim 3 to at least one of an egg or a chicken.

* * * * *